United States Patent
Galipeau et al.

(10) Patent No.: US 10,093,709 B2
(45) Date of Patent: Oct. 9, 2018

(54) GM-CSF AND IL-4 CONJUGATES, COMPOSITIONS, AND METHODS RELATED THERETO

(71) Applicants: Emory University, Atlanta, GA (US); Children's Healthcare of Atlanta, Inc., Atlanta, GA (US)

(72) Inventors: Jacques Galipeau, Atlanta, GA (US); Jiusheng Deng, Snellville, GA (US)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 0 days.

(21) Appl. No.: 15/491,777

(22) Filed: Apr. 19, 2017

(65) Prior Publication Data

US 2017/0226173 A1    Aug. 10, 2017

Related U.S. Application Data

(62) Division of application No. 14/436,491, filed as application No. PCT/US2013/066261 on Oct. 23, 2013, now Pat. No. 9,657,076.

(60) Provisional application No. 61/717,129, filed on Oct. 23, 2012.

(51) Int. Cl.
| | | |
|---|---|---|
| C07K 14/54 | (2006.01) | |
| C07K 14/535 | (2006.01) | |
| A61K 38/19 | (2006.01) | |
| A61K 35/14 | (2015.01) | |
| A61K 38/20 | (2006.01) | |
| A61K 38/00 | (2006.01) | |

(52) U.S. Cl.
CPC .......... *C07K 14/5406* (2013.01); *A61K 35/14* (2013.01); *A61K 38/193* (2013.01); *A61K 38/2026* (2013.01); *C07K 14/535* (2013.01); *A61K 38/00* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,108,910 A | 4/1992 | Curtis | |
| 6,011,002 A | 1/2000 | Pastan | |
| 6,617,135 B1 | 9/2003 | Gillies | |
| 6,838,081 B1 | 1/2005 | Roth | |
| 7,217,421 B1 | 5/2007 | McArthur | |
| 7,323,549 B2 | 1/2008 | Lauder | |
| 7,947,265 B2 | 5/2011 | Galipeau | |
| 8,323,657 B2 | 12/2012 | Nishimura | |
| 2004/0072299 A1 | 4/2004 | Gillies | |
| 2005/0053579 A1 | 3/2005 | Galipeau | |
| 2005/0214762 A1 | 9/2005 | Ross | |

FOREIGN PATENT DOCUMENTS

| | | |
|---|---|---|
| CN | 1258738 A | 7/2000 |
| WO | 1999051257 | 10/1999 |
| WO | 2001010912 | 2/2001 |
| WO | 2009062001 | 5/2009 |
| WO | 2010132867 | 11/2010 |
| WO | 2012031603 | 3/2012 |

OTHER PUBLICATIONS

Hong, Experimental and Molecular Medicine, 2016; vol. 48, pp. 1-8.*
Aliper et al, Cancer Medicine 2014; vol. 3, No. 4, pp. 737-746.*
Li et al, Cellular & Molecular Immunology, 2009; vol. 6, No. 6, pp. 415-422.*
Deng et al. Reprogramming of B cells into regulatory cells with engineered fusokines, Infect Disord Drug Targets. 2012, 12(3): 248-254.
Deng et al. GM-CSF and IL-4 Derived Fusion Cytokine Reprograms Leukemic B-Cells to Anti-CLL Effectors, Blood, 2012, 120:4606.
Deng et al. GM-CSF and IL-4 Derived Fusion Cytokine Triggers Conversion of B-Cells to Tumoricidal Effectors, Blood, 2012, 120:21.
Deng et al. Engineered Fusokine GIFT4 Licenses the Ability of B Cells to Trigger a Tumoricidal T-cell Response, Cancer Res; 2014, 74(15); 4133-44.
Deng et al. B cells for cancer immunotherapy, OncoImmunology, 2014, 3:10, e955702.
Deng et al. GM-CSF and IL-4 Fusion Cytokine Induces B Cell-Dependent Hematopoietic Regeneration, Molecular Therapy vol. 25 No. 2, 2017, 416-426.
Gillies et al. Bi-functional cytokine fusion proteins for gene therapy and antibody-targeted treatment of cancer, Cancer Immunol Immunother (2002) 51: 449-460.
Hikino et al. Granulocyte/Macrophage Colony-stimulating Factor and Interleukin-4-induced Dendritic Cells, Anticancer Research 24: 1609-1616 (2004).
Penafuerte et al. The human ortholog of granulocyte macrophage colony-stimulating factor and interleukin-2 fusion protein induces potent ex vivo natural killer cell activation and maturation, Cancer Res. 2009, 69(23):9020-8.
Rafei et al. A granulocyte-macrophage colony-stimulating factor and interleukin-15 fusokine induces a regulatory B cell population with immune suppressive properties, Nat Med 2009, 15(9):1038-45.

(Continued)

*Primary Examiner* — Bridget E Bunner
*Assistant Examiner* — Fozia Hamud
(74) *Attorney, Agent, or Firm* — Emory Patent Group

(57) ABSTRACT

In certain embodiments, this disclosure relates to conjugates comprising a polypeptide of GM-CSF and a polypeptide IL-4. Typically, the GM-CSF and IL-4 are connected by a linker, e.g., polypeptide. In certain embodiments, the disclosure relates to isolated nucleic acids encoding these polypeptide conjugates, vectors comprising nucleic acid encoding polypeptide conjugates, and protein expression systems comprising these vectors such as infectious viral particles and host cells comprising such nucleic acids.

3 Claims, 21 Drawing Sheets
Specification includes a Sequence Listing.

(56) References Cited

OTHER PUBLICATIONS

Stagg et al. GM-CSF / IL-2 Fusion Transgene is More Potent than GM-CSF and IL-2 in Combination and is Dependent upon CD8 and NK Cells for Antitumor Effect,Molecular Therapy (2004) 9, S133-S133.
Williams et al., Hematopoietic effects of a granulocyte-macrophage colony-stimulating factor/interleukin-3 fusion protein, Cancer,1991, 67(10 Suppl):2705-7.
Williams et al., GMCSF-interleukin fusion cytokines induce novel immune effectors that can serve as biopharmaceuticals for treatment of autoimmunity and cancer. J Intern Med. 2011, 269(1):74-84.
Extended European Search Report for EP Application No. 13849808.4 dated Apr. 18, 2016.
European Communication for EP Application No. 13849808.4 dated Mar. 16, 2017.

\* cited by examiner

GM-CSF  MWLQNLLFLGIVVYSLSAPTRSPITVTRPWKHVEAIKEALNLLDDMPVTLNEEVEVV
SNEFSFKKLTCVQTRLKIFEQGLRGNFTKLKGALNMTASYYQTYCPPTPETDCETQV
TTYADFIDSLKTFLTDIPFECKKPGQKSMGLNPQLVVILLFFLECTRSHIHGCDKNHL
IL-4  REIIGILNEVTGEGTPCTEMDVPNVLTATKNTTESELVCRASKVLRIFYLKHGKTPCLK
KNSSVLMELQRLFRAFRCLDSSISCTMNESKSTSLKDFLESLKSIMQMDYS (282 aa)
SEQ ID NO: 7
FIG. 1A
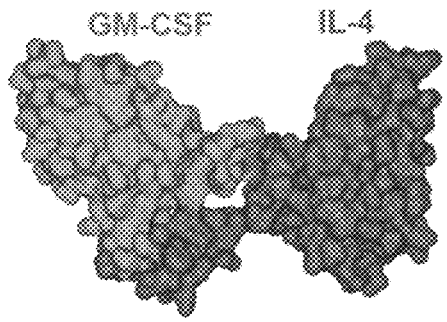
FIG. 1B
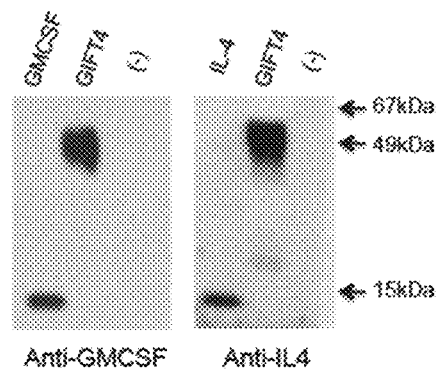
FIG. 1C
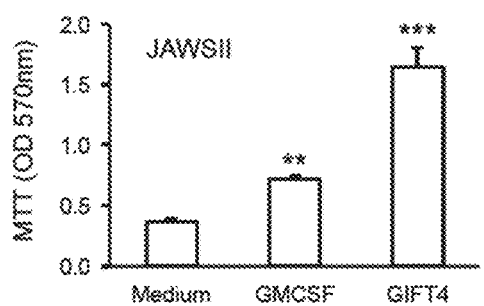
FIG. 1D
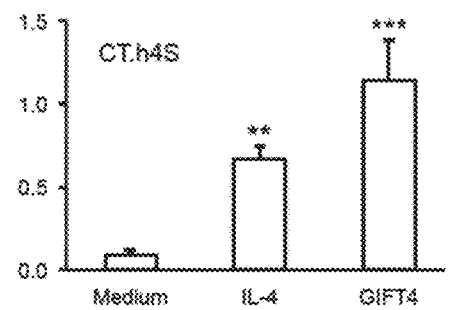
FIG. 1E GM-CSF  MWLQSLLLLGTVACSISAPARSPSPSTQPWEHVNAIQEARRLLNLSRDTAAEMNETVE
        VISEMFDLQEPTCLQTRLELYKQGLRGSLTKLKGPLTMMASHYKQHCPPTPETSCATQT
        ITFESFKENLKDFLLVIPFDCWEPVQESMGLTSQLLPPLFFLLACAGNFVHGHKCDITLQE
IL-4    IIKTLNSLTEQKTLCTELTVTDIFAASKNTTEKETFCRAATVLRQFYSHHEKDTRCLGATA
        QQFHRHKQLIRFLKRLDRNLWGLAGLNSCPVKEANQSTLENFLERLKTIMREKYSKCSS

SEQ ID NO:8

FIG. 11A

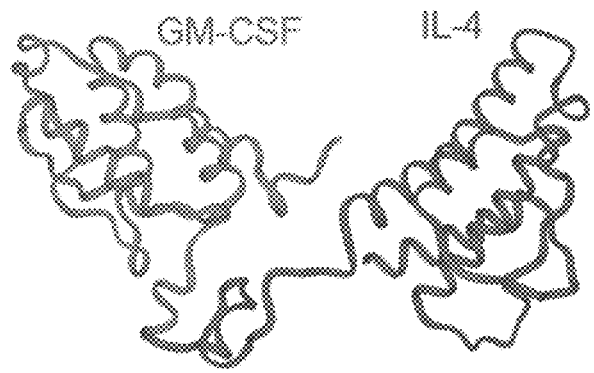

FIG. 11B

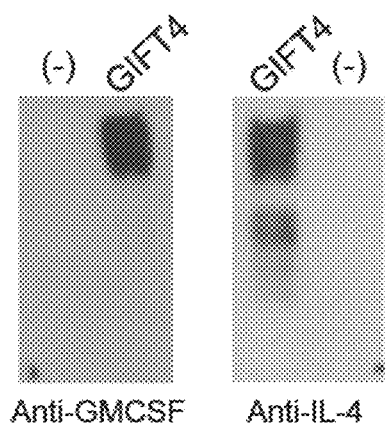

FIG. 11C

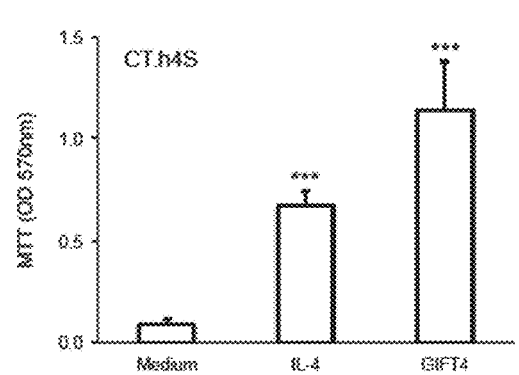

FIG. 11D

SEQUENCE LISTING

```
<160> NUMBER OF SEQ ID NOS: 8

<210> SEQ ID NO 1
<211> LENGTH: 139
<212> TYPE: PRT
<213> ORGANISM: Mus musculus

<400> SEQUENCE: 1

Met Trp Leu Gln Asn Leu Leu Phe Leu Gly Ile Val Val Ser Leu Ser
1               5                   10                  15

Ala Pro Thr Arg Ser Pro Ile Thr Val Thr Arg Pro Trp Lys His Val
            20                  25                  30

Glu Ala Ile Lys Glu Ala Leu Asn Leu Leu Asp Asp Met Pro Val Thr
        35                  40                  45

Asn Glu Glu Val Glu Val Val Ser Asn Glu Phe Ser Phe Lys Lys Leu
    50                  55                  60

Thr Cys Val Gln Thr Arg Leu Lys Ile Phe Glu Gln Gly Leu Arg Gly
65                  70                  75                  80

Asn Phe Thr Lys Leu Lys Gly Ala Leu Asn Met Thr Ala Ser Tyr Tyr
                85                  90                  95

Gln Thr Tyr Cys Pro Pro Thr Pro Glu Thr Asp Cys Glu Thr Gln Val
            100                 105                 110

Thr Thr Tyr Ala Asp Phe Ile Asp Ser Leu Lys Thr Phe Leu Thr Asp
        115                 120                 125

Ile Pro Phe Glu Cys Lys Lys Pro Gly Gln Lys
    130                 135

<210> SEQ ID NO 2
<211> LENGTH: 140
<212> TYPE: PRT
<213> ORGANISM: Mus musculus

<400> SEQUENCE: 2

Met Gly Leu Asn Pro Gln Leu Val Val Ile Leu Leu Phe Phe Leu Glu
1               5                   10                  15

Cys Thr Arg Ser His Ile His Gly Cys Asp Lys Asn His Leu Arg Glu
            20                  25                  30

Ile Ile Gly Ile Leu Asn Glu Val Thr Gly Glu Gly Thr Pro Cys Thr
        35                  40                  45
```

```
Glu Met Asp Val Pro Asn Val Leu Thr Ala Thr Lys Asn Thr Thr Glu
     50                  55                  60

Ser Glu Leu Val Cys Arg Ala Ser Lys Val Leu Arg Ile Phe Tyr Leu
65                  70                  75                  80

Lys His Gly Lys Thr Pro Cys Leu Lys Lys Asn Ser Ser Val Leu Met
                 85                  90                  95

Glu Leu Gln Arg Leu Phe Arg Ala Phe Arg Cys Leu Asp Ser Ser Ile
                100                 105                 110

Ser Cys Thr Met Asn Glu Ser Lys Ser Thr Ser Leu Lys Asp Phe Leu
             115                 120                 125

Glu Ser Leu Lys Ser Ile Met Gln Met Asp Tyr Ser
             130                 135                 140

<210> SEQ ID NO 3
<211> LENGTH: 153
<212> TYPE: PRT
<213> ORGANISM: Homo sapiens

<400> SEQUENCE: 3

Met Gly Leu Thr Ser Gln Leu Leu Pro Pro Leu Phe Phe Leu Leu Ala
1               5                  10                  15

Cys Ala Gly Asn Phe Val His Gly His Lys Cys Asp Ile Thr Leu Gln
             20                  25                  30

Glu Ile Ile Lys Thr Leu Asn Ser Leu Thr Glu Gln Lys Thr Leu Cys
         35                  40                  45

Thr Glu Leu Thr Val Thr Asp Ile Phe Ala Ala Ser Lys Asn Thr Thr
 50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                 85                  90                  95

Phe His Arg His Lys Gln Leu Ile Arg Phe Leu Lys Arg Leu Asp Arg
                100                 105                 110

Asn Leu Trp Gly Leu Ala Gly Leu Asn Ser Cys Pro Val Lys Glu Ala
             115                 120                 125

Asn Gln Ser Thr Leu Glu Asn Phe Leu Glu Arg Leu Lys Thr Ile Met
         130                 135                 140

Arg Glu Lys Tyr Ser Lys Cys Ser Ser
145                 150

<210> SEQ ID NO 4
<211> LENGTH: 137
<212> TYPE: PRT
<213> ORGANISM: Homo sapiens

<400> SEQUENCE: 4

Met Gly Leu Thr Ser Gln Leu Leu Pro Pro Leu Phe Phe Leu Leu Ala
1               5                  10                  15

Cys Ala Gly Asn Phe Val His Gly His Lys Cys Asp Ile Thr Leu Gln
             20                  25                  30

Glu Ile Ile Lys Thr Leu Asn Ser Leu Thr Glu Gln Lys Asn Thr Thr
         35                  40                  45

Glu Lys Glu Thr Phe Cys Arg Ala Ala Thr Val Leu Arg Gln Phe Tyr
 50                  55                  60

Ser His His Glu Lys Asp Thr Arg Cys Leu Gly Ala Thr Ala Gln Gln
65                  70                  75                  80
```

```
Phe His Arg His Lys Gln Leu Ile Arg Phe Leu Lys Arg Leu Asp Arg
                85                  90                  95

Asn Leu Trp Gly Leu Ala Gly Leu Asn Ser Cys Pro Val Lys Glu Ala
            100                 105                 110

Asn Gln Ser Thr Leu Glu Asn Phe Leu Glu Arg Leu Lys Thr Ile Met
        115                 120                 125

Arg Glu Lys Tyr Ser Lys Cys Ser Ser
    130                 135

<210> SEQ ID NO 5
<211> LENGTH: 5
<212> TYPE: PRT
<213> ORGANISM: Artificial sequence
<220> FEATURE:
<223> OTHER INFORMATION: Synthetic

<400> SEQUENCE: 5

Gly Gly Gly Gly Ser
1               5

<210> SEQ ID NO 6
<211> LENGTH: 144
<212> TYPE: PRT
<213> ORGANISM: Homo sapiens

<400> SEQUENCE: 6

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Thr Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 7
<211> LENGTH: 280
<212> TYPE: PRT
<213> ORGANISM: Artificial sequence
<220> FEATURE:
<223> OTHER INFORMATION: Synthetic

<400> SEQUENCE: 7

Met Trp Leu Gln Asn Leu Leu Phe Leu Gly Ile Val Val Ser Leu Ser
1               5                   10                  15

Ala Pro Thr Arg Ser Pro Ile Thr Val Thr Arg Pro Trp Lys His Val
            20                  25                  30

Glu Ala Ile Lys Glu Ala Leu Asn Leu Leu Asp Asp Met Pro Val Thr
        35                  40                  45
```

```
Asn Glu Glu Val Glu Val Ser Asn Glu Phe Ser Phe Lys Lys Leu
    50                  55                  60

Thr Cys Val Gln Thr Arg Leu Lys Ile Phe Glu Gln Gly Leu Arg Gly
65                  70                  75                  80

Asn Phe Thr Lys Leu Lys Gly Ala Leu Asn Met Thr Ala Ser Tyr Tyr
                85                  90                  95

Gln Thr Tyr Cys Pro Pro Thr Pro Glu Thr Asp Cys Glu Thr Gln Val
            100                 105                 110

Thr Thr Tyr Ala Asp Phe Ile Asp Ser Leu Lys Thr Phe Leu Thr Asp
        115                 120                 125

Ile Pro Phe Glu Cys Lys Lys Pro Gly Gln Lys Ser Met Gly Leu Asn
    130                 135                 140

Pro Gln Leu Val Val Ile Leu Leu Phe Phe Leu Glu Cys Thr Arg Ser
145                 150                 155                 160

His Ile His Gly Cys Asp Lys Asn His Leu Arg Glu Ile Ile Gly Ile
                165                 170                 175

Leu Asn Glu Val Thr Gly Glu Gly Thr Pro Cys Thr Glu Met Asp Val
            180                 185                 190

Pro Asn Val Leu Thr Ala Thr Lys Asn Thr Thr Glu Ser Glu Leu Val
        195                 200                 205

Cys Arg Ala Ser Lys Val Leu Arg Ile Phe Tyr Leu Lys His Gly Lys
    210                 215                 220

Thr Pro Cys Leu Lys Lys Asn Ser Ser Val Leu Met Glu Leu Gln Arg
225                 230                 235                 240

Leu Phe Arg Ala Phe Arg Cys Leu Asp Ser Ser Ile Ser Cys Thr Met
                245                 250                 255

Asn Glu Ser Lys Ser Thr Ser Leu Lys Asp Phe Leu Glu Ser Leu Lys
            260                 265                 270

Ser Ile Met Gln Met Asp Tyr Ser
        275                 280

<210> SEQ ID NO 8
<211> LENGTH: 298
<212> TYPE: PRT
<213> ORGANISM: Artificial sequence
<220> FEATURE:
<223> OTHER INFORMATION: Synthetic

<400> SEQUENCE: 8

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Thr Ile Thr Phe Glu Ser Phe Lys Glu Asn Leu Lys
        115                 120                 125
```

-continued

```
Asp Phe Leu Leu Val Ile Pro Phe Asp Cys Trp Glu Pro Val Gln Glu
    130                 135                 140
Ser Met Gly Leu Thr Ser Gln Leu Leu Pro Pro Leu Phe Phe Leu Leu
145                 150                 155                 160
Ala Cys Ala Gly Asn Phe Val His Gly His Lys Cys Asp Ile Thr Leu
            165                 170                 175
Gln Glu Ile Ile Lys Thr Leu Asn Ser Leu Thr Glu Gln Lys Thr Leu
            180                 185                 190
Cys Thr Glu Leu Thr Val Thr Asp Ile Phe Ala Ala Ser Lys Asn Thr
        195                 200                 205
Thr Glu Lys Glu Thr Phe Cys Arg Ala Ala Thr Val Leu Arg Gln Phe
    210                 215                 220
Tyr Ser His His Glu Lys Asp Thr Arg Cys Leu Gly Ala Thr Ala Gln
225                 230                 235                 240
Gln Phe His Arg His Lys Gln Leu Ile Arg Phe Leu Lys Arg Leu Asp
            245                 250                 255
Arg Asn Leu Trp Gly Leu Ala Gly Leu Asn Ser Cys Pro Val Lys Glu
            260                 265                 270
Ala Asn Gln Ser Thr Leu Glu Asn Phe Leu Glu Arg Leu Lys Thr Ile
        275                 280                 285
Met Arg Glu Lys Tyr Ser Lys Cys Ser Ser
    290                 295
```

GM-CSF AND IL-4 CONJUGATES, COMPOSITIONS, AND METHODS RELATED THERETO

CROSS REFERENCE TO RELATED APPLICATIONS

This application is a division of U.S. application Ser. No. 14/436,491 filed Apr. 17, 2015, which is the National Stage of International Application Number PCT/US2013/066261 filed Oct. 23, 2013, which claims the benefit of priority to U.S. Provisional Application No. 61/717,129 filed Oct. 23, 2012. The entirety of each of these applications is hereby incorporated by reference for all purposes.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 12066USDIV_ST25.txt. The text file is 12 KB, was created on Apr. 19, 2017, and is being submitted electronically via EFS-Web.

BACKGROUND

Cancer is thought to occur as a result of an immune system that is not properly removing uncontrolled proliferating cancer cells. Stimulating the immune system to recognize and eliminate cancerous cells has become a promising strategy for therapeutic treatments. Proleukin® (aldesleukin) contains a recombinant human Interleukin 2 (IL-2) thought to boost the immune system against cancer cells and is indicated for the treatment of adults with metastatic renal cell carcinoma (metastatic RCC). Severe adverse events generally accompany this therapy at the recommended dosages. Thus, there is a need to identify improved methods.

The cytokine granulocyte macrophage colony stimulating factor (GM-CSF) enhances the adaptive immune system by enhancing antigen presentation and co-stimulation by dendritic cells (DC). Due to its immune stimulatory functions, GM-CSF has been used to augment host immune systems against cancer and to boost the white blood cell count for patients after chemotherapy. Provenge™ is a FDA-approved autologous cellular cancer immunotherapy treatment. Peripheral blood leukocytes of a subject are harvested via leukapheresis. These enriched monocytes are incubated with prostatic acid phosphatase (PAP) conjugated to granulocyte macrophage colony stimulating factor (PAP-GM-CSF). GM-CSF is thought to direct the target antigen to receptors on DC precursors, which then present PAP on their cell surface in a context sufficient to activate T cells for the cells that express PAP. Activated, PAP presenting DCs are administered to the subject to elicit an immune response retarding cancer growth. This strategy requires isolation and expansion of cells of the subject, and typically treatment does not entirely clear the subject of cancer or tumors. Thus, there is a need to identify improved methods.

Interleukin 4 (IL-4) is a γ-chain cytokine. It serves as a signal to activate and elicit antibody class switching by B lymphocytes and converts naïve helper T lymphocytes to active T lymphocytes and then expand their population. U.S. Pat. No. 6,838,081 reports enhancing the development of antigen presenting cells from precursor cells by administering a combination of IL-4 and GM-CSF. See also U.S. Patent Application 2004/0072299 and Hikino et al., ANTICANCER RESEARCH 24: 1609-1616 (2004).

GIFT fusokines are the fused proteins derived from GM-CSF and common γ chain interleukin fusion transgenes and may either suppress or enhance host immune response. Stagg et al., Molecular Therapy, 2004, 9, S133-S133, disclose a GM-CSF/IL-2 Fusion (GIFT2). See also Penafuete et al., Cancer Res. 2009, 69(23):9020-8; Rafei et al., Nat Med. 2009, 15(9):1038-45; Williams and Park, Cancer, 1991, 67(10 Suppl):2705-7; WO 2005/0053579; WO 2005/026820; WO 2008/0014612; and U.S. Pat. Nos. 7,323,549; 7,217,421; 6,617,135; and 5,108,910.

SUMMARY

In certain embodiments, this disclosure relates to conjugates comprising a polypeptide of GM-CSF and a polypeptide IL-4. Typically, the GM-CSF and IL-4 are connected by a linker, e.g., polypeptide. In certain embodiments, the disclosure relates to isolated nucleic acids encoding these polypeptide conjugates, vectors comprising nucleic acid encoding polypeptide conjugates, and protein expression systems comprising these vectors such as infectious viral particles and host cells comprising such nucleic acids.

In certain embodiments, the disclosure relates to pharmaceutical compositions comprising conjugates and vectors disclosed herein and a pharmaceutically acceptable excipient. In certain embodiments, the disclosure relates to vaccines comprising conjugates and vectors disclosed herein and an antigen and optionally an adjuvant. Typically, the antigen is contained in a live attenuated virus, killed virus, a virus-like particle, virosome, cancerous cell, lipid bilayer structure with a surface antigen, and the antigen is typically a viral protein or glycoprotein, bacteria, or bacterial antigen, or tumor associated antigen. In certain embodiments, the antigen is conjugated to a dendritic cell marker.

In certain embodiments, the disclosure contemplates a method of mixing conjugates herein with B cells under conditions such that activated normal B cells can produce chemokine CCL3 or elevated levels of INF-gamma. In certain embodiments, the B-cells are chronic lymphoid leukemia B-cells. In certain embodiments, the mixing is in vitro or in vivo. In certain embodiments, in vitro activated B cells are administered to a subject, e.g., from which the B cells were originally obtained in an amount to effectively treat or prevent cancer.

In certain embodiments, the disclosure relates to methods of treating or preventing a viral, bacterial, or parasitic infection comprising administering an effective amount of a pharmaceutical composition comprising a conjugate or vector disclosed herein optionally in combination with an antigen and optionally an adjuvant. In certain embodiments, the subject is at risk or, exhibiting symptoms of, or diagnosed with a viral infection, such as a chronic viral infection.

In certain embodiments, the disclosure relates to methods of treating or preventing a viral infection comprising administering an effective amount of a vaccine comprising a conjugate disclosed herein to a subject in need thereof.

In certain embodiments, the subject is diagnosed with influenza A virus including subtype H1N1, influenza B virus, influenza C virus, rotavirus A, rotavirus B, rotavirus C, rotavirus D, rotavirus E, SARS coronavirus, human adenovirus types (HAdV-1 to 55), human papillomavirus (HPV) Types 16, 18, 31, 33, 35, 39, 45, 51, 52, 56, 58, and 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), yellow fever virus, measles virus, mumps virus, respiratory syncytial virus, rinderpest virus, California encephalitis virus, hantavirus, rabies virus, ebola virus, marburg virus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, or Kaposi's sarcoma-associated herpesvirus, hepatitis A, hepatitis B, hepatitis C, hepatitis D, hepatitis E or human immunodeficiency virus (HIV).

In certain embodiments, the disclosure relates to administering a conjugate or vector disclosed herein in combination with another antiviral agent such as abacavir, acyclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, trizivir, tromantadine, truvada, valaciclovir, valganciclovir, vicriviroc, vidarabine, viramidine zalcitabine, zanamivir, and/or zidovudine.

In certain embodiments, the disclosure relates to methods of treating or preventing cancer comprising administering a pharmaceutical composition comprising a conjugate or vector disclosed herein to a subject in need thereof.

In certain embodiments, the disclosure relates to methods of treating or preventing cancer comprising administering autologous blood cells activated with a cancer antigen conjugated to GM-CSF in combination with a conjugate disclosed herein to a subject in need thereof.

In certain embodiments, the disclosure relates to methods of activating peripheral blood cells comprising mixing peripheral blood cells with a conjugate disclosed herein comprising a tumor associated antigen/cancer marker under conditions such that increase expression of CD54 occurs. In certain embodiments, the disclosure relates to product produced by mixing peripheral blood cells and with a conjugate disclosed herein under conditions such that increase expression of CD54 occurs. In certain embodiments, the disclosure relates to methods of treating or preventing cancer comprising administering an effective amount of a product made by mixing peripheral blood cells with a conjugate disclosed herein to subject from whom the peripheral blood cells were obtained.

In certain embodiments, the disclosure relates to methods of producing compositions comprising isolated bone marrow and/or bone marrow stem cells comprising administering conjugates and compositions disclosed herein, e.g., GIFT4, GIFT4 in combination with B cells, or isolated cells activated with GIFT4, optionally in combination with B cells, to a subject. In certain embodiments, the disclosure relates to the treatment or prevention of irradiation-caused bone marrow failure comprising administering conjugates and compositions disclosed herein to a subject in need thereof.

In certain embodiments, the disclosure relates to methods of increasing the production of bone marrow and/or bone marrow stem cells comprising administering an effective amount of a conjugate disclosed herein to subject. In certain embodiments, the disclosure relates to a product made by the process of isolating bone marrow and/or bone marrow stem cells from a subject administered with a conjugate disclosed herein.

In certain embodiments, the disclosure relates to methods of increasing the production of bone marrow stem cells comprising administering an effective amount of a conjugate disclosed herein in combination with B cells to subject that is B cell deficient.

In certain embodiments, the subject is diagnosed with a B-cell immunodeficiency, defects of B-cell development/immunoglobulin production, excessive/uncontrolled B-cell proliferation, leukemia, chronic lymphocytic leukemia, lymphoma, follicular non-hodgkin's lymphoma, diffuse large B cell lymphoma, or lupus.

In certain embodiments, the disclosure relates to a product made by the process of isolating bone marrow and/or bone marrow stem cells from a subject administered with a conjugate disclosed herein in combination with B cells.

In certain embodiments, the disclosure relates to a composition comprising isolated bone marrow cells and/or bone marrow stem cells and a conjugate disclosed herein, e.g., GM-CSF and IL-4 conjugate. In certain embodiments, the bone marrow cells and/or bone marrow stem cells are obtain from a subject that was previously administered the conjugate under conditions such that the bone marrow cells and/or bone marrow stem cells increase proliferation.

In certain embodiments, the disclosure relates to methods of treating or preventing bone marrow failure comprising administering an effective amount of a product made by mixing bone marrow cells with a conjugate disclosed herein to subject. In certain embodiments, the bone marrow failure is caused by irradiation. In certain embodiments, the product made by mixing bone marrow cells with a conjugate disclosed herein is administered in combination with a conjugate disclosed herein to subject. In certain embodiments, the conjugate is GIFT4. In certain embodiments, the bone marrow cells were obtained from the subject.

In certain embodiments, the disclosure relates to methods of treating or preventing cancer comprising administering an effective amount of a product made by mixing bone marrow cells with a conjugate disclosed herein to subject. In certain embodiments, the product made by mixing bone marrow cells with a conjugate disclosed herein is administered in combination with a conjugate disclosed herein to subject. In certain embodiments, the conjugate is GIFT4. In certain embodiments, the bone marrow cells were obtained from the subject.

In some embodiments, the disclosure relates to a method of treating or preventing cancer comprising by administering a pharmaceutical composition comprising conjugates or vector disclosed herein to a subject diagnosed with, exhibiting symptoms of, or at risk of cancer wherein the cancer is a hematological malignancy such as a leukemia or lymphoma, acute lymphoblastic leukemia (ALL), acute myelogenous leukemia (AML), chronic lymphocytic leukemia (CLL), small lymphocytic lymphoma (SLL), chronic myelogenous leukemia, acute monocytic leukemia (AMOL), Hodgkin's lymphomas, and non-Hodgkin's lymphomas such as Burkitt lymphoma, B-cell lymphoma and multiple myeloma. Other contemplated cancers include cervical, ovarian, colon, breast, gastric, lung, skin, ovarian, pancreatic, prostate, head, neck, and renal cancer.

Within any of the cancer management methods disclosed herein, the conjugate or vector may be administered in combination with an anti-cancer agent such as gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vincristine, vinblastine, vindesine, vinorelbine taxol, taxotere, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, bevacizumab, combretastatin, thalidomide, and/or lenalidomide or combinations thereof. In certain embodiments, combination therapies with proleukin (recombinant human IL-2) and or interferon alpha are contemplated.

In certain embodiments, the disclosure relates to gene therapies comprising administering vectors comprising nucleic acid encoding conjugates disclosed herein to a subject in need thereof. In certain embodiments, the nucleic acids are isolated and/or purified from their natural state or translated to a non-naturally occurring form such as cDNA.

In certain embodiments, the disclosure contemplates incorporating conjugates disclosed herein into the surfaces of particles, e.g., cells, liposomes, micelles, vesicles, bilayer structures, virosomes, and virus-like particles. The conjugates may be linked to lipophilic moieties, e.g., fatty acids and GPI. In one example, the disclosure contemplates a GPI anchored conjugate comprising GPI, GM-CSF, IL-4, and optionally an antigen, adjuvant, or other polypeptide. It is contemplated that these particles may contain other surface polypeptides, antigens and co-stimulatory molecules such as B7-1, B7-2, ICAM-1, and/or IL-2. It is contemplated that these particles may be used in all the applications conjugates disclosed herein are mentioned.

Within certain embodiments, any of the conjugates disclosed herein may be further conjugated to an adjuvant, cytokine, co-stimulatory molecule, antigen, protein, or glycoprotein. In certain embodiments, the antigen is a viral protein or a cancer marker.

In certain embodiments, the cancer marker is selected from PAP (prostatic acid phosphatase), prostate-specific antigen (PSA), (PSMA) prostate-specific membrane antigen, early prostate cancer antigen-2 (EPCA-2), AKAP-4 (A kinase [PRKA] anchor protein 4), NGEP (new gene expressed in prostate), PSCA (prostate stem cell antigen), STEAP (six-transmembrane epithelial antigen of the prostate), MUC 1 (mucin 1), HER-2, BCL-2, MAGE antigens such as CT7, MAGE-A3 and MAGE-A4, ERKS, G-protein coupled estrogen receptor 1, CA15-3, CA19-9, CA 72-4, CA-125, carcinoembryonic antigen, CD20, CD31, CD34, PTPRC (CD45), CD99, CD117, melanoma-associated antigen (TA-90), peripheral myelin protein 22 (PMP22), epithelial membrane proteins (EMP-1, -2, and -3), HMB-45 antigen, MART-1 (Melan-A), S100A1, and S100B or fragments or mutated forms thereof.

In certain embodiments, the viral antigen is selected from an influenza virus hemagglutinin and neuraminidase; cytomegalovirus glycoprotein gB, p28, p38, p50, p52, p65, and p150; Borrelia p41; HIV nef, integrase, gag, protease, tat, env, p31, p17, p24, p31, p55, p66, gp32, gp36, gp39, gp41, gp120, and gp160; SIV p55; HBV core, surface antigen, and australian antigen; HCV core nucleocapsid, NS3, NS4, and NS5; Dengue env and NS1; EBV early antigen, p18, p23, gp125, nuclear antigen (EBNA)-1, EBNA-2, EBNA-3A, EBNA-3B, EBNA-3C, EBNA-leader protein (EBNA-LP), latent membrane proteins (LMP)-1, LMP-2A and LMP-2B; and herpes simplex virus gD and gG or fragments or mutated forms thereof.

In certain embodiments, the adjuvant or cytokine is selected from IL-2, IL-12, IL-15, IL-7, IL-18, IL-21, IL-27, IL-31, IFN-alpha, flagellin, unmethylated, CpG oligonucleotide, lipopolysaccharides, lipid A, and heat stable antigen (HSA).

In certain embodiments, the disclosure contemplates administration of pharmaceutical products comprising conjugates disclosed herein by intravenous (IV), subcutaneous (SC), or intraperitoneal (IP) administration.

BRIEF DESCRIPTION OF THE DRAWINGS

FIG. 1A illustrates the GIFT4 protein (SEQ ID NO: 7). Amino acid sequence of murine GIFT4 protein-GM-CSF amino acids (SEQ ID NO:1), the linker S, and IL-4 amino acids (SEQ ID NO: 2).

FIG. 1B shows the predicted three-dimensional structure of GIFT4 protein.

FIG. 1C shows intact GIFT4 protein (50 KDa) expressed by 293T cells, detected by Western blot with both anti-mouse GM-CSF and IL-4 antibodies.

FIG. 1D shows data when GM-CSF-responsive JAWSII cells were treated with GIFT4 or recombinant GM-CSF or IL-4 for 72 hours, medium served as control. Cell growth was analyzed by MTT assay.

FIG. 1E shows data when IL-4-responsive CT.h4S cells were treated.

FIG. 11A illustrates human GIFT4 protein (SEQ ID NO: 8), a polypeptide of GM-CSF, MWLQSLLLLGTV ACSI-SAPARS PSPSTQPWEHVNAI QEARRLLN LSRD-TAAEMN ETVEVISE MFDLQEPTC LQTRLELYKQGL RGSLTKLKGPLTMMASH YKQHCPPTPETSCATQ TIT-FESF KENLKDFLL VIPFDCWEPVQE (SEQ ID NO: 6), an S linker and, human isoform 1 of IL-4 (SEQ ID NO: 3).

FIG. 11B shows a 3D structure of human GIFT4 protein.

FIG. 11C shows data when GIFT4 protein expressed by genetic-modified 293T-GIFT4 cells was detected by Western blot.

FIG. 11D shows GIFT4 has strong biological signaling activities of IL-4 signaling and induces proliferation of IL-4-responder CT.h4S cells.

DETAILED DESCRIPTION

Figure 2A:
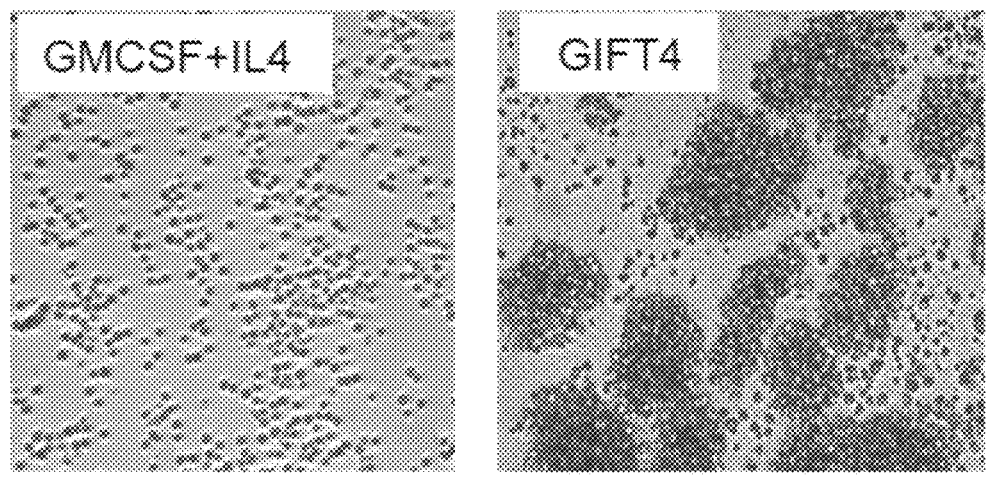
FIG. 2A shows data on the phenotype of GIFT4-treated B cells. Induction of B cell proliferation by GIFT4 stimulation. The cells were cultured for 4 days. Combined use of recombinant GM-CSF and IL-4 served as control.

Common γ chain interleukin cytokines include IL-2, IL-4, IL-7, IL-9, IL-15 and IL-21, and have important roles in the activation and differentiation of lymphocytes. IL-2 has strong immune modulatory properties on T cells, and had been approved by FDA as the first interleukin immunotherapeutic agent to use to treat patients with advanced kidney cancer and metastatic melanoma. Unfortunately, IL-2 immunotherapy even combined with various chemotherapy drugs has not shown significant improvement of survival time in cancer patients. In addition, IL-2 has frequent, often serious and sometimes fatal side effects due to capillary leakage.

GIFT2 shows anti-tumor activities via induction of tumor-killer NK cells. GIFT2 affects tumoricidal dendritic cells. In contrast, GIFT15 (derived from GM-CSF and IL-15) has immune suppressive function to abrogate inflammatory response in multiple sclerosis. Here, a fusokine derive from GM-CSF and IL-4 (GIFT4) is show to be a cancer immunotherapeutic agent. Functionally different from GM-CSF and IL-4 that induces monocytes to differentiate into dendritic cells in vitro, GIFT4 directly elicits adaptive B-cell immune response and consequent T cell immunity.

GM-CSF-IL-4 Fusokine (GIFT4)

FIG. 1 provides for an embodiment of this disclosure comprising a GM-CSF sequence and a murine IL-4 sequence and FIG. 11 provides s human sequence. In certain embodiments, the disclosure contemplates a fusokine with a recombinant human form such as isoform 1 which is amino acids sequence MGLTSQLLPP LFFLLACAGN FVHGH-KCDIT LQEIIKTLNS LTEQKTLCTE LTVTDIFAAS KNTTEKETFC RAATVLRQFY SHHEKDTRCL GATAQQFHRH KQLIRFLKRL DRNLWGLAGL NSCPVKEANQ STLENFLERL KTIMREKYSK CSS (SEQ ID NO: 3) or isoform 2 which is amino acid sequence MGLTSQLLPP LFFLLACAGN FVHGHKCDIT LQEIIK-TLNS LTEQKNTTEK ETFCRAATVL RQFYSHHEKD TRCLGATAQQ FHRHKQLIRF LKRLDRNLWG LAGLNSCPVK EANQSTLENFLERLKTIMRE KYSKCSS (SEQ ID NO: 4). Isoform 2 lacks an in-frame exon in the 5' region, compared to variant 1, resulting an isoform (2) that lacks an internal region, as compared to isoform 1.

The present disclosure encompasses fusion proteins involving full-length pre-processed forms, as well as mature processed forms, fragments thereof and variants of each or both of the GM-CSF and IL-4 entities with linker amino acids, including allelic as well as non-naturally occurring variants. In addition to naturally-occurring allelic variants of the GM-CSF and IL-4 entities that may exist in the population, the skilled artisan will further appreciate that changes (i.e. one or more deletions, additions and/or substitutions of one or more amino acid) can be introduced by mutation using classic or recombinant techniques to effect random or targeted mutagenesis. A suitable variant in use in the present disclosure typically has an amino acid sequence having a high degree of homology with the amino acid sequence of the corresponding native cytokine. In one embodiment, the amino acid sequence of the variant cytokine in use in the fusion protein of the disclosure is at least 70%, at least about 75%, at least about 80%, at least about 90%, typically at least about 95%, more typically at least about 97% and even more typically at least about 99% identical to the corresponding native sequence, e.g., SEQ ID NO: 3 or 4. In certain embodiments, such native sequence is of human GM-CSF and/or human IL-4.

Percent identities between amino acid or nucleic acid sequences can be determined using standard methods known to those of skill in the art. For instance for determining the percentage of homology between two amino acid sequences, the sequences are aligned for optimal comparison purposes. The amino acid residues at corresponding amino acid positions are then compared. Gaps can be introduced in one or both amino acid sequence(s) for optimal alignment and non-homologous sequences can be disregarded for comparison purposes. When a position in the first sequence is occupied by the same amino acid residue as the corresponding position in the second sequence, then the sequences are identical at that position. The percent identity between the two sequences is a function of the number of identical positions shared by the sequences, taking into account the number of gaps which need to be introduced for optimal alignment and the length of each gap. The comparison of sequences and determination of percent identity and similarity between two sequences can be accomplished using a mathematical algorithm (e.g. Computational Molecular Biology, 1988, Ed Lesk A M, Oxford University Press, New York; Biocomputing: Informatics and Genome Projects, 1993, Ed Smith D. W., Academic Press, New York; Computer Analysis of Sequence Data, 1994, Eds Griffin A. M. and Griffin H. G., Human Press, New Jersey; Sequence Analysis Primer, 1991, Eds Griskov M. and Devereux J., Stockton Press, New York). Moreover, various computer programs are available to determine percentage identities between amino acid sequences and between nucleic acid sequences, such as GCG™ program (available from Genetics Computer Group, Madison, Wis.), DNAsis™ program (available from Hitachi Software, San Bruno, Calif.) or the MacVector™ program (available from the Eastman Kodak Company, New Haven, Conn.).

Suitable variants of GM-CSF and IL-4 entities for use in the present disclosure are biologically active and retain at least one of the activities described herein in connection with the corresponding polypeptide. Typically, the therapeutic effect (e.g. anti-tumor activity, by-pass of tumor-induced immune energy) is preserved, although a given function of the polypeptide(s) may be positively or negatively affected to some degree, e.g. with variants exhibiting reduced cytotoxicity or enhanced biological activity. Amino acids that are essential for a given function can be identified by methods known in the art, such as by site-directed mutagenesis. Amino acids that are critical for binding a partner/substrate (e.g. a receptor) can also be determined by structural analysis such as crystallization, nuclear magnetic resonance and/or photoaffinity labeling. The resulting variant can be tested for biological activity in assays such as those described above.

For example, in one class of functional variants, one or more amino acid residues are conservatively substituted. A "conservative amino acid substitution" is one in which the amino acid residue in the native polypeptide is replaced with an amino acid residue having a similar side chain. Families of amino acid residues having similar side chains have been defined in the art. Typically, substitutions are regarded as conservative when the replacement, one for another, is among the aliphatic amino acids Ala, Val, Leu, and Ile; the hydroxyl residues Ser and Thr; the acidic residues Asp and Glu; the amide residues Asn and Gln; the basic residues Lys and Arg; or the aromatic residues Phe and Tyr. Alternatively, in another embodiment, mutations can be introduced randomly along all or part of a cytokine coding sequence, such as by saturation mutagenesis, and the resultant mutant can be screened for its biological activity as described herein to identify mutants that retain at least therapeutic activity.

Although the GM-CSF and IL-4 entities can be directly fused in the fusion protein of the disclosure, it is however typical to use a linker for joining GM-CSF and IL-4. The purpose of the linker is to allow the correct formation, folding and/or functioning of each of the GM-CSF and IL-4 entities. It should be sufficiently flexible and sufficiently long to achieve that purpose. Typically, the coding sequence of the linker may be chosen such that it encourages translational pausing and therefore independent folding of the GM-CSF and IL-4 entities. A person skilled in the art will be able to design suitable linkers in accordance with the disclosure. The present disclosure is, however, not limited by the form, size or number of linker sequences employed. Multiple copies of the linker sequence of choice may be inserted between GM-CSF and IL-4. The only requirement for the linker sequence is that it functionally does not adversely interfere with the folding and/or functioning of the individual entities of the fusion protein. For example, a suitable linker is 1 to 5 or 5 to 50 amino acid long and may comprise amino acids such as glycine, serine, threonine, asparagine, alanine and proline (see for example Wiederrecht et al., 1988, Cell 54, 841; Dekker et al., 1993, Nature 362, 852; Sturm et al., 1988, Genes and Dev. 2, 1582; Aumailly et al., 1990 FEBS Lett. 262, 82). Repeats comprising serine and glycine residues are typical in the context of the disclosure. Specific examples of suitable linkers consists of two or three or more (e.g. up to eight or more) copies of the sequence Gly-Gly-Gly-Gly-Ser (GGGGS) (SEQ ID NO: 5). It will be evident that the disclosure is not limited to the use of these particular linkers.

The disclosure further includes fusion proteins which comprise, or alternatively consist essentially of, or alternatively consist of an amino acid sequence which is at least 70%, 75%, 80%, 90%, 95%, 97%, 99% homologous or even better 100% homologous (identical) to all or part of any of the amino acid sequences recited in SEQ ID NO: 1-6.

In the context of the present disclosure, a protein "consists of" an amino acid sequence when the protein does not contain any amino acids but the recited amino acid sequence. A protein "consists essentially of" an amino acid sequence when such an amino acid sequence is present together with only a few additional amino acid residues, typically from about 1 to about 50 or so additional residues. A protein "comprises" an amino acid sequence when the amino acid sequence is at least part of the final (i.e. mature) amino acid sequence of the protein. Such a protein can have a few up to several hundred additional amino acids residues. Such additional amino acid residues can be naturally associated with each or both entities contained in the fusion or heterologous amino acid/peptide sequences (heterologous with respect to the respective entities). Such additional amino acid residues may play a role in processing of the fusion protein from a precursor to a mature form, may facilitate protein trafficking, prolong or shorten protein half-life or facilitate manipulation of the fusion protein for assay or production, among other things. Typically, the fusion proteins of the disclosure comprise a signal peptide at the $NH_2$-terminus in order to promote secretion in the host cell or organism. For example, the endogenous signal peptide (i.e. naturally present in the cytokine present at the $NH_2$ terminus of said fusion) can be used or alternatively a suitable heterologous (with respect to the cytokine in question) signal peptide sequence can be added to the cytokine entity present at the $NH_2$ terminus of the fusion or inserted in replacement of the endogenous one.

In the context of the disclosure, the fusion proteins of the disclosure can comprise cytokine entities of any origin, i.e. any human or animal source (including canine, avian, bovine, murine, ovine, feline, porcine, etc). Although "chimeric" fusion proteins are also encompassed by the disclosure (e.g. one cytokine entity of human origin and the other of an animal source), it is typical that each entity be of the same origin (e.g. both from humans).

The fusion proteins of the present disclosure can be produced by standard techniques. Polypeptide and DNA sequences for each of the cytokines involved in the fusion protein of the present disclosure are published in the art, as are methods for obtaining expression thereof through recombinant or chemical synthetic techniques. In another embodiment, a fusion-encoding DNA sequence can be synthesized by conventional techniques including automated DNA synthesizers. Then, the DNA sequence encoding the fusion protein may be constructed in a vector and operably linked to a regulatory region capable of controlling expression of the fusion protein in a host cell or organism. Techniques for cloning DNA sequences for instance in viral vectors or plasmids are known to those of skill in the art (Sambrook et al, 2001, "Molecular Cloning. A Laboratory Manual", Laboratory Press, Cold Spring Harbor N.Y.). The fusion protein of the disclosure can be purified from cells that have been transformed to express it.

The present disclosure also provides a nucleic acid molecule encoding the fusion protein of the disclosure. Within the context of the present disclosure, the term "nucleic acid" and "polynucleotide" are used interchangeably and define a polymer of nucleotides of any length, either deoxyribonucleotide (DNA) molecules (e.g., cDNA or genomic DNA) and ribonucleotide (RNA) molecules (e.g., mRNA) and analogs of the DNA or RNA generated using nucleotide analogs (see U.S. Pat. No. 5,525,711 and U.S. Pat. No. 4,711,955 as examples of nucleotide analogs). If present, modifications to the nucleotide structure may be imparted before or after assembly of the polymer. The sequence of nucleotides may also be interrupted by non-nucleotide elements. The nucleic acid molecule may be further modified after polymerization, such as by conjugation with a labeling component. The nucleic acid, especially DNA, can be double-stranded or single-stranded, but typically is double-stranded DNA. Single-stranded nucleic acids can be the coding strand (sense strand) or the non-coding strand (anti-sense strand).

The nucleic acid molecules of the disclosure include, but are not limited to, the sequence encoding the fusion protein alone, but may comprise additional non-coding sequences, for example introns and non-coding 5' and 3' sequences that play a role in transcription, mRNA processing (including splicing and polyadenylation signals), ribosome binding and mRNA stability. For example, the nucleic acid molecule of the disclosure can contain less than about 5 kb, 4 kb, 3 kb, 2 kb, 1 kb, 0.5 kb or 0.1 kb of nucleotide sequences which naturally flank (i.e. sequences located at the 5' and 3' ends) or are present within the genomic DNA encoding GM-CSF and IL-4 entities.

According to a typical embodiment, the present disclosure provides nucleic acid molecules which comprise, or alternatively consist essentially of, or alternatively consist of a nucleotide sequence encoding all or part of an amino acid sequence encoding a fusion protein which is at least about 70%, at least about 75%, at least about 80%, at least about 90%, at least about 95%, typically at least about 97%, more typically at least about 99% homologous or even more typically 100% homologous to any of the amino acid sequences shown in SEQ ID NO: 1-6.

In another embodiment, a nucleic acid molecule of the disclosure comprises a nucleic acid molecule which is a complement of all or part of a nucleotide sequence encoding the fusion protein shown in any of SEQ ID NO: 1-6. A nucleic acid molecule which is complementary to the nucleotide sequence of the present disclosure is one which is sufficiently complementary such that it can hybridize to the fusion-encoding nucleotide sequence under stringent conditions, thereby forming a stable duplex. Such stringent conditions are known to those skilled in the art. A typical, non-limiting example of stringent hybridization conditions are hybridization in 6 times sodium chloride/sodium citrate (SSC) at about 45 C, followed by one or more washes in 0.2 times SSC, 0.1% SDS at 50-65 C. In one embodiment, the disclosure pertains to antisense nucleic acid to the nucleic acid molecules of the disclosure. The antisense nucleic acid can be complementary to an entire coding strand, or to only a portion thereof.

In still another embodiment, the disclosure encompasses variants of the above-described nucleic acid molecules of the disclosure e.g., that encode variants of the fusion proteins that are described above. The variation(s) encompassed by the present disclosure can be created by introducing one or more nucleotide substitutions, additions and/or deletions into the nucleotide sequence by standard techniques, such as site-directed mutagenesis and PCR-mediated mutagenesis. Following mutagenesis, the variant nucleic acid molecule can be expressed recombinantly as described herein and the activity of the resulting protein can be determined using, for example, assays described herein. Alternatively, the nucleic acid molecule of the disclosure can be altered to provide preferential codon usage for a specific host cell (for example *E. coli*; Wada et al., 1992, Nucleic Acids Res. 20, 2111-2118). The disclosure further encompasses nucleic acid molecules that differ due to the degeneracy of the genetic code and thus encode the same fusion protein as any of those shown in SEQ ID NO: 1-6.

Another embodiment of the disclosure pertains to fragments of the nucleic acid molecule of the disclosure, e.g. restriction endonuclease and PCR-generated fragments. Such fragments can be used as probes, primers or fragments encoding an immunogenic portion of the fusion protein.

The nucleic acid molecules of the present disclosure can be generated using the sequence information provided herein. The nucleic acid encoding each of the GM-CSF and IL-4 entities can be cloned or amplified using cDNA or, alternatively, genomic DNA, as a template and appropriate probes or oligonucleotide primers according to standard molecular biology techniques (e.g., as described in Sambrook, et al. "Molecular Cloning: A Laboratory Manual", Cold Spring Harbor Laboratory Press, Cold Spring Harbor, N.Y., 2001) or standard PCR amplification techniques based on sequence data accessible in the art (such as those provided above in connection with the fusion proteins of the disclosure or those provided in the Examples part). Fusing of the GM-CSF sequence to the IL-4 sequence may be accomplished as described in the Experimental below or by conventional techniques. For example, the GM-CSF and IL-4 encoding sequences can be ligated together in-frame either directly or through a sequence encoding a peptide linker. The GM-CSF-encoding sequence can also be inserted directly into a vector which contains the IL-4-encoding sequence, or vice versa. Alternatively, PCR amplification of the GM-CSF and IL-4-encoding sequences can be carried out using primers which give rise to complementary overhangs which can subsequently be annealed and re-amplified to generate a fusion gene sequence.

GM-CSF and IL-4 Fusion Cytokine Triggers Conversion of B-Cells to Tumoricidal Effectors Studies herein indicate that the GIFT4 fusokine has the powerful capability to convert naive B-cells to tumoricidal effectors. Given its potential impact on host B cell immune functions, fusokine GIFT4 offers a strategy for immunotherapy against a wide variety of cancers, e.g., using a B cell-based cancer immunotherapy.

In certain embodiments the disclosure contemplates the fusokine GIFT4 (derive from GM-CSF and IL-4) use as a cancer immunotherapeutic agent. Functionally different from GM-CSF and IL-4 that induces monocytes to differentiate into dendritic cells in vitro, GIFT4 directly elicits adaptive B-cell immune response and consequent T cell immunity. See Gluckman et al., Cytokines, cellular & molecular therapy, 1997, 3:187-196. GIFT4 fusokine is a potent activator to trigger robust B cell immunity against tumor. Uniquely, GIFT4-B cells secrete an array of innate cytokines such as IL-1β, IL-6, IL-12, VEGF, GM-CSF and chemokine CCL3, but not IL-10 and IFN-γ. The pro-Th1 cytokines IL-12, IL-1β and IL-6 can promote IFN-γ production by T cells and enhance host anti-tumor immunity. As a parental molecule of GIFT4, IL-4 stimulation only induces strong phosphorylation of STST6 in B cells, with little or weak phosphorylation of other STATs. However, GIFT4 protein shows gain-of-function to trigger hyper-phosphorylation of STAT1, STAT3, STAT5 and STAT6 upon ligation with B cells, the former two STATs are the major downstream signaling pathways for other IL-2 common γ chain family members including IL-2, IL-7, IL-9, IL-15 and IL-21. Phosphorylation of STAT3 is related to the production of IL-1β and IL-6. There is no report that STAT phosphorylation results in CCL3 secretion by normal B cells; however, BCR stimulation activates leukemic B cells to produce chemokine CCL3. See Miyauchi et al., Cancer science, 2011, 102:1236-1241. Although GIFT4 protein possesses the functional activities of both GM-CSF and IL-4 components, how phosphorylation of STATs leads to the secretion of GM-CSF and CCL3 by GIFT4-B cells remains unclear.

GIFT4-B cells have a unique phenotype expressing surface markers B220, CD19, CD40, CD80, CD86, and IgM, but not CD23. GIFT4-B cells secrete high amount of GM-CSF. Unlike IRA-B cells that secrete high amounts of GM-CSF (See Rauch et al., Science, 2012, 335:597-601), GIFT4-B cells are $CD80^+CD86^+$ that are typical markers for antigen-presenting cells. The phenotype of GIFT4-B cells is also different from B1 cells and B2 cells, of which B1 cells are $B220^{low}$, and B2 cells are $CD23^+$. Unlike IRA B cells, GIFT4-B cells also secrete IL-1β, IL-5, IL-6, IL-12, VEFG and massive CCL3, but not IL-3 that is uniquely produced by IRA B cells. To our knowledge, it is the first report that activated normal B cells can produce chemokine CCL3. Therefore, GIFT4-B cells have distinct cytokine-secreting profile that can enhance IFN-γ-mediated T cell antitumor immunity, but sharing some common surface markers with IRA-B cells. Strikingly, GIFT4-B cells have the plasticity to isotype switch from IgM to IgG upon BCR cross-linking; similar to IL-4 and anti-mouse IgM-treated B cells. Thus, GIFT4-B cells could function as both innate effectors and adaptive responders against a variety of cancers, and possible infectious pathogens.

GIFT4 fusokine triggers previously un-described B cell-dependent anti-tumor immunity in a murine model of melanoma. B cells comprise heterogeneous subpopulations of B-lymphocytes with two sides of immune activities either enhancing or suppressing host immunity via B cell cytokine secretion, antibody production, and cellular interaction. Early investigation showed that B cells suppress host immune response against tumors by inhibition of T cell tumorcidial activities via IL-10 mediated pathway. However, new emerging evidences suggest that B cells play important protective roles in anti-tumor immunity. Studies disclosed herein demonstrated that GIFT4 induce B cell-initiated anti-melanoma immune response.

Administration of GIFT4 protein in vivo results in the expansion of a global of B cells including GM-CSF-secreting IRA-like B cells without expansion IL-10-producing regulatory B cells, since GIFT4-B cells do not secretes IL-10. GM-CSF has been shown to increase the proliferation of antigen-activated cytotoxic T cells; chemokine CCL3 is important for recruiting $CCR5^+$ T cells in anti-tumor immunity, suggesting that GM-CSF and CCL3-producing GIFT4-B cells have potent efficacy to promote T cell immunity against tumors. In addition, VEGF-producing B cells facilitate dendritic cells migration in vivo. Co-culture of GIFT4-B cells with T cells markedly increase IFN-γ production by T cells further verifies that GIFT4-B cells actively participate in cellular immunity by augmenting the magnitude of $IFN-γ^+$ T cell response. The robust growth of B16F0 melanoma tumors in B-cell deficient mice that possess normal T cell function confirms that GIFT4-triggered anti-tumor immunity is B cell-dependent. The fact that B cells can act as real antigen-presenting cells to directly license cytotoxic T cells and establish long-lasting antitumor immunity strongly indicates that GIFT4-B cells function like dendritic cells to elicit T-cell immunity against tumors.

Antigen-specific antibody production is an important protective arm of B effector cells against infectious pathogens and cancers. IL-4 has been shown to participate in genera-tion and expansion of memory B cells upon antigen-BCR ligation; however IL-4 stimulation could not increase the number of plasma cells. See Choe et al., Journal of immunology, 1997, 159:3757-3766. TLR ligands CpG oligodeoxynucleotides and LPS can activate memory B cells and differentiate into plasma cells in vitro, but lose the capability in vivo. Dramatic expansion of antigen-specific plasma cells and augmentation of antigen-specific antibody production in vivo by GIFT4 stimulation indicates that GIFT4 protein is a potent stimulator for B cell anti-tumor humoral response. In melanoma mouse model, immunization of GIFT4-secreting B16F0 cells leads to tumor-specific antibody secretion in immunized mice suggests that GIFT4 is a powerful adjuvant for induction of anti-melanoma specific antibodies. The complete inhibition of melanoma tumor growth in B16F0-GIFT4 cell-immunized B6 mice indicates that GIFT4 elicits acquired anti-tumor B cell immunity. Fc-receptor substantially contributes to the action of cytotoxic antibodies against tumors through antibody-dependent cell-mediated cytotoxicity pathway (ADCC). Data that mice lack of Fcγ receptor could not prevent GIFT4-secreting B16F0 tumor growth further highlights the participation of ADCC in GIFT4-triggered B-cell anti-melanoma immunity. In a pre-established melanoma model, adoptive transfer of tumor-primed B cells remarkably inhibited melanoma growth in B cell deficient mice further confirms the anti-melanoma effect of GIFT4 is dependent on the adoptive B-cell activity.

Pharmaceutical Compositions

As used herein the language "pharmaceutically acceptable excipient" is intended to include any and all carriers, solvents, diluents, excipients, adjuvants, dispersion media, coatings, antibacterial and antifungal agents, and absorption delaying agents, and the like, compatible with pharmaceutical administration.

Suitably, the pharmaceutical composition of the disclosure comprises a carrier and/or diluent appropriate for its delivering by injection to a human or animal organism. Such carrier and/or diluent is non-toxic at the dosage and concentration employed. It is selected from those usually employed to formulate compositions for parental administration in either unit dosage or multi-dose form or for direct infusion by continuous or periodic infusion. It is typically isotonic, hypotonic or weakly hypertonic and has a relatively low ionic strength, such as provided by sugars, polyalcohols and isotonic saline solutions. Representative examples include sterile water, physiological saline (e.g. sodium chloride), bacteriostatic water, Ringer's solution, glucose or saccharose solutions, Hank's solution, and other aqueous physiologically balanced salt solutions (see for example the most current edition of Remington: The Science and Practice of Pharmacy, A. Gennaro, Lippincott, Williams & Wilkins). The pH of the composition of the disclosure is suitably adjusted and buffered in order to be appropriate for use in humans or animals, typically at a physiological or slightly basic pH (between about pH 8 to about pH 9, with a special preference for pH 8.5). Suitable buffers include phosphate buffer (e.g. PBS), bicarbonate buffer and/or Tris buffer. A typical composition is formulated in 1M saccharose, 150 mM NaCl, 1 mM MgCl2, 54 mg/1 Tween 80, 10 mM Tris pH 8.5. Another typical composition is formulated in 10 mg/ml mannitol, 1 mg/ml HSA, 20 mM Tris, pH 7.2, and 150 mM NaCl.

The composition of the disclosure can be in various forms, e.g. in solid (e.g. powder, lyophilized form), or liquid (e.g. aqueous). In the case of solid compositions, the typical methods of preparation are vacuum drying and freeze-drying which yields a powder of the active agent plus any additional desired ingredient from a previously sterile-filtered solution thereof. Such solutions can, if desired, be stored in a sterile ampoule ready for reconstitution by the addition of sterile water for ready injection.

Nebulized or aerosolized formulations also form part of this disclosure. Methods of intranasal administration are well known in the art, including the administration of a droplet, spray, or dry powdered form of the composition into the nasopharynx of the individual to be treated from a pressured container or dispenser which contains a suitable propellant, e.g., a gas such as carbon dioxide, or a nebulizer (see for example WO 95/11664). Enteric formulations such as gastroresistant capsules and granules for oral administration, suppositories for rectal or vaginal administration also form part of this disclosure. For non-parental administration, the compositions can also include absorption enhancers which increase the pore size of the mucosal membrane. Such absorption enhancers include sodium deoxycholate, sodium glycocholate, dimethyl-beta-cyclodextrin, lauroyl-1-lysophosphatidylcholine and other substances having structural similarities to the phospholipid domains of the mucosal membrane.

The composition can also contain other pharmaceutically acceptable excipients for providing desirable pharmaceutical or pharmacodynamic properties, including for example modifying or maintaining the pH, osmolarity, viscosity, clarity, color, sterility, stability, rate of dissolution of the formulation, modifying or maintaining release or absorption into an the human or animal organism. For example, polymers such as polyethylene glycol may be used to obtain desirable properties of solubility, stability, half-life and other pharmaceutically advantageous properties (Davis et al., 1978, Enzyme Eng. 4, 169-173; Burnham et al., 1994, Am. J. Hosp. Pharm. 51, 210-218). Representative examples of stabilizing components include polysorbate 80, L-arginine, polyvinylpyrrolidone, trehalose, and combinations thereof. Other stabilizing components especially suitable in plasmid-based compositions include hyaluronidase (which is thought to destabilize the extra cellular matrix of the host cells as described in WO 98/53853), chloroquine, protic compounds such as propylene glycol, polyethylene glycol, glycerol, ethanol, 1-methyl L-2-pyrrolidone or derivatives thereof, aprotic compounds such as dimethylsulfoxide (DMSO), diethylsulfoxide, di-n-propylsulfoxide, dimethylsulfone, sulfolane, dimethyl-formamide, dimethylacetamide, tetramethylurea, acetonitrile (see EP 890 362), nuclease inhibitors such as actin G (WO 99/56784) and cationic salts such as magnesium ($Mg^{2+}$) (EP 998 945) and lithium ($Li^+$) (WO 01/47563) and any of their derivatives. The amount of cationic salt in the composition of the disclosure typically ranges from about 0.1 mM to about 100 mM, and still more typically from about 0.1 mM to about 10 mM. Viscosity enhancing agents include sodium carboxymethylcellulose, sorbitol, and dextran. The composition can also contain substances known in the art to promote penetration or transport across the blood barrier or membrane of a particular organ (e.g. antibody to transferrin receptor; Friden et al., 1993, Science 259, 373-377). A gel complex of poly-lysine and lactose (Midoux et al., 1993, Nucleic Acid Res. 21, 871-878) or poloxamer 407 (Pastore, 1994, Circulation 90, 1-517) can be used to facilitate administration in arterial cells.

The composition of the disclosure may also comprise one or more adjuvant(s) suitable for systemic or mucosal application in humans. Representative examples of useful adjuvants include without limitation alum, mineral oil emulsion such as Freunds complete and incomplete, lipopolysaccharide or a derivative thereof (Ribi et al., 1986, Immunology and Immunopharmacology of Bacterial Endotoxins, Plenum Publ. Corp., NY, p407-419), saponins such as QS21 (Sumino et al., 1998, J. Virol. 72, 4931-4939; WO 98/56415), Escin, Digitonin, *Gypsophila* or *Chenopodium quinoa* saponins and CpG oligodeoxynucleotides. Alternatively the composition of the disclosure may be formulated with conventional vaccine vehicles composed of chitosan or other polycationic polymers, polylactide and polylactide-coglycolide particles, poly-N-acetyl glucosamine-based polymer matrix, particles composed of polysaccharides or chemically modified polysaccharides, and lipid-based particles, etc. The composition may also be formulated in the presence of cholesterol to form particulate structures such as liposomes.

The composition may be administered to patients in an amount effective, especially to enhance an immune response in an animal or human organism. As used herein, the term "effective amount" refers to an amount sufficient to realize a desired biological effect. For example, an effective amount for enhancing an immune response could be that amount necessary to cause activation of the immune system, for instance resulting in the development of an anti-tumor response in a cancerous patient (e.g. size reduction or regression of the tumor into which the composition has been injected and/or distant tumors). The appropriate dosage may vary depending upon known factors such as the pharmacodynamic characteristics of the particular active agent, age, health, and weight of the host organism; the condition(s) to be treated, nature and extent of symptoms, kind of concurrent treatment, frequency of treatment, the need for prevention or therapy and/or the effect desired. The dosage will also be calculated dependent upon the particular route of administration selected. Further refinement of the calculations necessary to determine the appropriate dosage for treatment is routinely made by a practitioner, in the light of the relevant circumstances. The titer may be determined by conventional techniques. A composition based on vector plasmids may be formulated in the form of doses of between 1 μg to 100 mg, advantageously between 10 μg and 10 mg and typically between 100 μg and 1 mg. A composition based on proteins may be formulated in the form of doses of between 10 ng to 100 mg. A typical dose is from about 1 μg to about 10 mg of the therapeutic protein per kg body weight. The administration may take place in a single dose or a dose repeated one or several times after a certain time interval. In one typical embodiment, the composition of the present disclosure is administered by injection using conventional syringes and needles, or devices designed for ballistic delivery of solid compositions (WO 99/27961), or needleless pressure liquid jet device (U.S. Pat. No. 4,596, 556; U.S. Pat. No. 5,993,412).

The composition of the disclosure can be enclosed in ampoules, disposable syringes or multiple dose vials made of glass or plastic. In all cases, the composition must be sterile and should be fluid to the extent that easy syringability exists. It must be stable under the conditions of manufacture and storage and must be preserved against the contaminating action of microorganisms such as bacteria and fungi. Sterile injectable solutions can be prepared by incorporating the active agent (e.g., a fusion protein or infectious particles) in the required amount with one or a combination of ingredients enumerated above, followed by filtered sterilization.

Methods of Use

The pharmaceutical composition of the disclosure may be employed in methods for treating or preventing a variety of diseases and pathologic conditions, including genetic diseases, congenital diseases and acquired diseases such as infectious diseases (e.g. viral and/or bacterial infections), cancer, immune deficiency diseases, and autoimmune diseases. Accordingly, the present disclosure also encompasses the use of the fusion protein, vector, infectious viral particle, host cell or composition of the disclosure for the preparation of a drug intended for treating or preventing such diseases, and especially cancer or an infectious disease.

The composition of the present disclosure is particularly intended for the preventive or curative treatment of disorders, conditions or diseases associated with cancer. The term "cancer" encompasses any cancerous conditions including diffuse or localized tumors, metastasis, cancerous polyps and preneoplastic lesions (e.g. dysplasies) as well as diseases which result from unwanted cell proliferation. A variety of tumors may be selected for treatment in accordance with the methods described herein. In general, solid tumors are typical. Cancers which are contemplated in the context of the disclosure include without limitation glioblastoma, sarcoma, melanomas, mastocytoma, carcinomas as well as breast cancer, prostate cancer, testicular cancer, ovarian cancer, endometrial cancer, cervical cancer (in particular, those induced by a papilloma virus), lung cancer (e.g. lung carcinomas including large cell, small cell, squamous and adeno-carcinomas), renal cancer, bladder cancer, liver cancer, colon cancer, anal cancer, pancreatic cancer, stomach cancer, gastrointestinal cancer, cancer of the oral cavity, larynx cancer, brain and CNS cancer, skin cancer (e.g. melanoma and non-melanoma), blood cancer (lymphomas, leukemia, especially if they have developed in solid mass), bone cancer, retinoblastoma and thyroid cancer. In one typical embodiment of the use of the disclosure, the composition is administered into or in close proximity to a solid tumor.

In certain embodiments, the disclosure contemplates uses of conjugates disclosed herein in autologous immune enhancement therapy (AIET). AIET is a treatment method in which immune or cancer cells, e.g., lymphokine-activated killer (LAK) cells, natural killer (NK) cells, cytotoxic T lymphocytes (CTLs), dendritic cells (DCs), are taken out from the body of a subject which are cultured and processed to activate them until their resistance to cancer is strengthened and then the cells are put back in the body. The cells, antibodies, and organs of the immune system work to protect and defend the body against the tumor cells. In certain embodiments, the disclosure contemplates mixing harvested cells with conjugates of GM-CSF and IL-4 to activate them. In certain embodiments, the disclosure contemplates administering conjugates of GM-CSF and IL-4 when the cells are administered back to the subject.

In certain embodiments, the disclosure contemplates the administration of sipuleucel-T (PROVENGE) in combination with a conjugate of GM-CSF and IL-4. PROVENGE consists of autologous peripheral blood mononuclear cells, including antigen presenting cells (APCs), that have been activated during a culture period with a recombinant human protein, PAP-GM-CSF, consisting of prostatic acid phosphatase (PAP), an antigen expressed in prostate cancer tissue, linked to GM-CSF. In certain embodiments, the disclosure relates to a conjugate comprising PAP, GM-CSF, and IL-4, and uses in activating antigen presenting cells in peripheral blood mononuclear cells. The peripheral blood mononuclear cells of the subject may be obtained via a standard leukapheresis procedure prior to infusion. During culture, the recombinant antigen can bind to and be processed by antigen presenting cells (APCs). The recombinant antigen is believed to direct the immune response to PAP. The infused product is believed to contain antigen presenting cells, dendritic cells, T cells, B cells, natural killer (NK) cells, and other cells. Typically each dose contains more than 50 million autologous $CD54^+$ cells activated with PAP-GM-CSF or PAP-GM-CSF-IL-4. The potency is typically evaluated by measuring the increased expression of the CD54 molecule, also known as ICAM-1, on the surface of APCs after culture with PAP-GM-CSF or PAP-CM-CSF-IL-4. CD54 is a cell surface molecule that plays a role in the immunologic interactions between APCs and T cells, and is considered a marker of immune cell activation.

In certain embodiments, the disclosure contemplates methods for treating cancer comprising administering any GM-CSF and IL-4 conjugate disclosed herein as an immune adjuvant in combination with a vector that encodes a tumor associated antigen/cancer marker, such as PSA, PAP, and optionally encoding other co-stimulatory molecules selected from, B7-1, B7-2, ICAM-1, GM-CSF, leukocyte function-associated antigen-3 (LFA-3). Other embodiments contemplated for the treatment of cancer include administering an effective amount of a vector that encodes a GM-CSF and IL-4 conjugate disclosed herein and optionally further encodes a tumor associated antigen/cancer marker and optionally encodes other co-stimulatory molecules to a subject. PROSTVAC is a recombinant vector encoding costimulatory molecules, as well as PSA as a vaccine target. Plasmid DNA is incorporated into either vaccinia or fowlpox viruses by means of a packing cell line. Patients are treated with a vaccinia prime followed by a series of fowlpox-based boosts.

In certain embodiments, the disclosure relates to methods of treating cancer comprising administering a GM-CSF and IL-4 conjugate in combination with an anti-CTLA-4 antibody. Anti-CTLA-4 antibody is contemplated to be administered in combination with any of the methods disclosed herein. It is believed that it binds to CTLA-4 surface glycoprotein on T-cell surface, minimizing immune autoregulation and potentially enhancing antitumor activity. Interactions between B7 molecules on antigen-presenting cells and CTLA-4 on tumor-specific T cells are inhibitory. Thus, CTLA-4 engagement negatively regulates the proliferation and function of such T cells. Under certain conditions, blocking CTLA-4 with a monoclonal antibody (ipilimumab or tremilimumab) restores T-cell function.

Other embodiments contemplated for the treatment of cancer include methods that utilize the extraction of cancer cells from a subject and incorporate glycosyl-phosphatidylinositol (GPI)-anchored co-stimulatory molecules such as B7-1 and B7-2 into tumor cell membranes optionally with a conjugate GM-CSF and IL-4 anchored GPI, and administering the modified cells to the subject in combination with a conjugate of GM-CSF and IL-7 to elicit an immune response. See e.g., McHugh et al., Cancer Res., 1999, 59(10):2433-7; Poloso et al., Mol Immunol., 2002, 38(11): 803-16; and Nagarajan & Selvaraj, Cancer Res., 2002, 62(10):2869-74.

Other pathologic diseases and conditions are also contemplated in the context of the disclosure, especially infectious diseases associated with an infection by a pathogen such as fungi, bacteria, protozoa and viruses. Representative examples of viral pathogens include without limitation human immunodeficiency virus (e.g. HIV-1 or HIV-2), human herpes viruses (e.g. HSV1 or HSV2), cytomegalovirus, Rotavirus, Epstein Barr virus (EBV), hepatitis virus (e.g. hepatitis B virus, hepatitis A virus, hepatitis C virus and hepatitis E virus), varicella-zoster virus (VZV), paramyxoviruses, coronaviruses; respiratory syncytial virus, parainfluenza virus, measles virus, mumps virus, flaviviruses (e.g. Yellow Fever Virus, Dengue Virus, Tick-borne encephalitis virus, Japanese Encephalitis Virus), influenza virus, and typically human papilloma viruses (e.g. HPV-6, 11, 16, 18, 31. 33). Representative examples of bacterial pathogens include Neisseria (e.g. *N. gonorrhea* and *N. meningitidis*); Bordetella (e.g. *B. pertussis, B. parapertussis* and *B. bronchiseptica*), Mycobacteria (e.g. *M. tuberculosis, M. bovis, M. leprae, M. avium, M. paratuberculosis, M. smegmatis*); Legionella (e.g. *L. pneumophila*); Escherichia (e.g. enterotoxic *E. coli*, enterohemorragic *E. coli*, enteropathogenic *E. coli*); Vibrio (e.g. *V. cholera*); Shigella (e.g. *S. sonnei, S. dysenteriae, S. flexnerii*); Salmonella (e.g. *S. typhi, S. paratyphi, S. choleraesuis, S. enteritidis*); Listeria (e.g. *L. monocytogenes*); Helicobacter (e.g. *H. pylori*); Pseudomonas (e.g. *P. aeruginosa*); Staphylococcus (e.g. *S. aureus, S. epidermidis*); Enterococcus (e.g. *E. faecalis, E. faecium*), Clostridium (e.g. *C. tetani, C. botulinum, C. difficile*); Bacillus (e.g. *B. anthracis*); Corynebacterium (e.g. *C. diphtheriae*), and Chlamydia (e.g. *C. trachomatis, C. pneumoniae, C. psittaci*). Representative examples of parasite pathogens include Plasmodium (e.g. *P. falciparum*), Toxoplasma (e.g. *T. gondii*) Leshmania (e.g. *L. major*), Pneumocystis (e.g. *P. carinii*), Trichomonas (e.g. *T. vaginalis*), Schisostoma (e.g. *S. mansoni*). Representative examples of fungi include Candida (e.g. *C. albicans*) and Aspergillus.

Examples of autoimmune diseases include, but are not limited to, multiple sclerosis (MS), scleroderma, rheumatoid arthritis, autoimmune hepatitis, diabetes mellitus, ulcerative colitis, Myasthenia gravis, systemic lupus erythematosus, Graves' disease, idiopathic thrombocytopenia purpura, hemolytic anemia, multiple myositis/dermatomyositis, Hashimoto's disease, autoimmune hypocytosis, Sjogren's syndrome, angitis syndrome and drug-induced autoimmune diseases (e.g., drug-induced lupus).

Moreover, as mentioned above, the fusion protein, nucleic acid molecule, vector, infectious particle, host cell and/or composition of the present disclosure can be used as an adjuvant to enhance the immune response of an animal or human organism to a particular antigen. This particular use of the present disclosure may be made in combination with one or more transgenes or transgene products as defined above, e.g. for purposes of immunotherapy. Typically, the active agent (e.g. fusion protein, infectious particle or pharmaceutical composition of the disclosure) is administered in combination with one or more transgenes or transgene products. Accordingly, there is typically also provided a composition comprising in combination a transgene product (e.g. a viral antigen or a suicide gene product) and a fusion protein as well as a composition comprising vector(s) or viral particles encoding a transgene product and a fusion protein. The transgene and the fusion-encoding nucleic acid sequences may be expressed from the same vector or from separate vectors which may have the same origin (e.g. adenoviral vectors) or a different origin (e.g. a MVA vector encoding the particular antigen and an adenoviral vector encoding the fusion protein). The fusion protein and the transgene product (or their respective encoding vectors) can be introduced into the host cell or organism either concomitantly or sequentially either via the mucosal and/or systemic route.

Combination Therapies

The cancer treatments disclosed herein can be applied as a sole therapy or can involve, conventional surgery or radiotherapy, hormonal therapy, or chemotherapy. Such chemotherapy can include one or more of the following categories of anti-tumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulfan and nitrosoureas); antimetabolites (for example antifolates such as fluoropyrimidines like 5-fluorouracil and gemcitabine, tegafur, raltitrexed, methotrexate, cytosine arabinoside and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin); and proteosome inhibitors (for example bortezomib [Velcade®]); and the agent anegrilide [Agrylin®]; and the agent alpha-interferon (ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-Her2 antibody trastuzumab and the anti-epidermal growth factor receptor (EGFR) antibody, cetuximab), farnesyl transferase inhibitors, tyrosine kinase inhibitors and serine/threonine kinase inhibitors, for example inhibitors of the epidermal growth factor family for example EGFR family tyrosine kinase inhibitors such as: N-(3-chloro-4-fluorophenyl)-7-methoxy-6-(3-morpholinopropoxy)quinazolin-4-amine (gefitinib), N-(3-ethynylphenyl)-6,7-bis(2-methoxyethoxy)quinazolin-4-amine (erlotinib), and 6-acrylamido-N-(3-chloro-4-fluorophenyl)-7-(3-morpholinopropoxy)quinazolin-4-amine (CI 1033), for example inhibitors of the platelet-derived growth factor family and for example inhibitors of the hepatocyte growth factor family, for example inhibitors of phosphotidylinositol 3-kinase (PI3K) and for example inhibitors of mitogen activated protein kinase kinase (MEK1/2) and for example inhibitors of protein kinase B (PKB/Akt), for example inhibitors of Src tyrosine kinase family and/or Abelson (Abl) tyrosine kinase family such as dasatinib (BMS-354825) and imatinib mesylate (Gleevec™); and any agents that modify STAT signalling;

(v) antiangiogenic agents such as those which inhibit the effects of vascular endothelial growth factor, (for example the anti-vascular endothelial cell growth factor antibody bevacizumab [Avastin™]) and compounds that work by other mechanisms (for example linomide, inhibitors of integrin ocvβ3 function and angiostatin);

(vi) vascular damaging agents such as Combretastatin A4;

(vii) antisense therapies, for example those which are directed to the targets listed above, such as an anti-RAS antisense; and (viii) immunotherapy approaches, including for example ex-vivo and in-vivo approaches to increase the immunogenicity of subject tumour cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumour cell lines and approaches using anti-idiotypic antibodies, and approaches using the immunomodulatory drugs thalidomide and lenalidomide [Revlimid®].

The combination therapy also contemplates use of the disclosed pharmaceutical compositions with radiation therapy or surgery, as an alternative, or a supplement, to a second therapeutic or chemotherapeutic agent.

A typical chronic lymphocytic leukemia (CLL) chemotherapeutic plan includes combination chemotherapy with chlorambucil or cyclophosphamide, plus a corticosteroid such as prednisone or prednisolone. The use of a corticosteroid has the additional benefit of suppressing some related autoimmune diseases, such as immunohemolytic anemia or immune-mediated thrombocytopenia. In resistant cases, single-agent treatments with nucleoside drugs such as fludarabine, pentostatin, or cladribine may be successful. Patients may consider allogeneic or autologous bone marrow transplantation. In certain embodiments, the disclosure contemplates combination treatments using conjugates disclosed herein in combination with chloroambucil, cyclophosphamide, prednisone, prednisolone, fludarabine, pentostatin, and/or cladribine or combinations thereof.

Treatment of acute lymphoblastic leukemia typically includes chemotherapy to bring about bone marrow remission. Typical regiments include prednisone, vincristine, and an anthracycline drug, L-asparaginase or cyclophosphamide. Other options include tprednisone, L-asparaginase, and vincristine. Consolidation therapy or intensification therapy to eliminate any remaining leukemia may include antimetabolite drugs such as methotrexate and 6-mercaptopurine (6-MP). In certain embodiments, the disclosure contemplates combination treatments using conjugates disclosed herein in combination with COP, CHOP, R-CHOP, imatinib, alemtuzumab, vincristine, L-asparaginase or cyclophosphamide, methotrexate and/or 6-mercaptopurine (6-MP). COP refers to a chemotherapy regimen used in the treatment of lymphoma of cyclophosphamide, vincristine, and prednisone or prednisolone and optionally hydroxydaunorubicin (CHOP) and optionally rituximab (R-CHOP).

In some embodiments, the disclosure relates to treating a viral infection by administering a GM-CSF and IL-4 conjugate in combination with a second antiviral agent. In further embodiments, a GM-CSF and IL-4 conjugate is administered in combination with one or more of the following agents: abacavir, acyclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir (Tamiflu), peginterferon alfa-2a, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, trizivir, tromantadine, truvada, valaciclovir (Valtrex), valganciclovir, vicriviroc, vidarabine, viramidine zalcitabine, zanamivir (Relenza), and/or zidovudine (AZT).

Antiviral agents include, but are not limited to, protease inhibitors (PIs), integrase inhibitors, entry inhibitors (fusion inhibitors), maturation inhibitors, and reverse transcriptase inhibitors (anti-retrovirals). Combinations of antiviral agents create multiple obstacles to viral replication, i.e., to keep the number of offspring low and reduce the possibility of a superior mutation. If a mutation that conveys resistance to one of the agents being taken arises, the other agents continue to suppress reproduction of that mutation. For example, a single anti-retroviral agent has not been demonstrated to suppress an HIV infection for long. These agents are typically taken in combinations in order to have a lasting effect. As a result, the standard of care is to use combinations of anti-retrovirals.

Reverse transcribing viruses replicate using reverse transcription, i.e., the formation of DNA from an RNA template. Retroviruses often integrate the DNA produced by reverse transcription into the host genome. They are susceptible to antiviral drugs that inhibit the reverse transcriptase enzyme. In certain embodiments the disclosure relates to methods of treating viral infections by administering a GM-CSF and IL-4 conjugate, and a retroviral agent such as nucleoside and nucleotide reverse transcriptase inhibitors (NRTI) and/or a non-nucleoside reverse transcriptase inhibitors (NNRTI). Examples of nucleoside reverse transcriptase inhibitors include zidovudine, didanosine, zalcitabine, stavudine, lamivudine, abacavir, emtricitabine, entecavir, apricitabine. Examples of nucleotide reverse transcriptase inhibitors include tenofovir and adefovir. Examples of non-nucleoside reverse transcriptase inhibitors include efavirenz, nevirapine, delavirdine, and etravirine.

In certain embodiments, the disclosure relates to methods of treating a viral infection by administering a GM-CSF and IL-4 conjugate optionally with an antigen in combination with an antiviral drug, e.g., 2',3'-dideoxyinosine and a cytostatic agent, e.g., hydroxyurea.

Human immunoglobulin G (IgG) antibodies are believed to have opsonizing and neutralizing effects against certain viruses. IgG is sometimes administered to a subject diagnosed with immune thrombocytopenic purpura (ITP) secondary to a viral infection since certain viruses such as, HIV and hepatitis, cause ITP. In certain embodiments, the disclosure relates to methods of treating or preventing viral infections comprising administering a GM-CSF and IL-4 conjugate in combination with an immunoglobulin to a subject. IgG is typically manufactured from large pools of human plasma that are screened to reduce the risk of undesired virus transmission. The Fc and Fab functions of the IgG molecule are usually retained. Therapeutic IgGs include Privigen, Hizentra, and WinRho. WinRho is an immunoglobulin (IgG) fraction containing antibodies to the Rho(D) antigen (D antigen). The antibodies have been shown to increase platelet counts in Rho(D) positive subjects with ITP. The mechanism is thought to be due to the formation of anti-Rho(D) (anti-D)-coated RBC complexes resulting in Fc receptor blockade, thus sparing antibody-coated platelets.

In some embodiments, the disclosure relates to treating a bacterial infection by administering a GM-CSF and IL-4 conjugate in combination with an antibiotic drug. In further embodiments, the subject is co-administered with an antibiotic selected from the group comprising of Sulfonamides, Diaminopyrimidines, Quinolones, Beta-lactam antibiotics, Cephalosporins, Tetracyclines, Notribenzene derivatives, Aminoglycosides, Macrolide antibiotics, Polypeptide antibiotics, Nitrofuran derivatives, Nitroimidazoles, Nicotinin acid derivatives, Polyene antibiotics, Imidazole derivatives or Glycopeptide, Cyclic lipopeptides, Glycylcyclines and Oxazolidinones. In further embodiments, these antibiotics include but are not limited to Sulphadiazine, Sulfones—[Dapsone (DDS) and Paraaminosalicyclic (PAS)], Sulfanilamide, Sulfamethizole, Sulfamethoxazole, Sulfapyridine, Trimethoprim, Pyrimethamine, Nalidixic acids, Norfloxacin, Ciproflaxin, Cinoxacin, Enoxacin, Gatifloxacin, Gemifloxacin, Grepafloxacin, Levofloxacin, Lomefloxacin, Moxifloxacin, Ofloxacin, Pefloxacin, Sparfloxacin, Trovafloxacin, Penicillins (Amoxicillin, Ampicillin, Azlocillin, Carbenicillin, Cloxacillin, Dicloxacillin, Flucloxacillin, Hetacillin, Oxacillin, Mezlocillin, Penicillin G, Penicillin V, Piperacillin), Cephalosporins (Cefacetrile, Cefadroxil, Cefalexin, Cefaloglycin, Cefalonium, Cefaloridin, Cefalotin, Cefapirin, Cefatrizine, Cefazaflur, Cefazedone, Cefazolin, Cefradine, Cefroxadine, Ceftezole, Cefaclor, Cefonicid, Ceforanide, Cefprozil, Cefuroxime, Cefuzonam, Cefmetazole, Cefoteta, Cefoxitin, Cefcapene, Cefdaloxime, Cefdinir, Cefditoren, Cefetamet, Cefixime, Cefmenoxime, Cefodizime, Cefoperazone, Cefotaxime, Cefotiam, Cefpimizole, Cefpiramide, Cefpodoxime, Cefteram, Ceftibuten, Ceftiofur, Ceftiolen, Ceftizoxime, Ceftriaxone, Cefoperazone, Ceftazidime, Cefepime), Moxolactam, Carbapenems (Imipenem, Ertapenem, Meropenem), Monobactams (Aztreonam), Oxytetracycline, Chlortetracycline, Clomocycline, Demeclocycline, Tetracycline, Doxycycline, Lymecycline, Meclocycline, Methacycline, Minocycline, Rolitetracycline, Chloramphenicol, Amikacin, Gentamicin, Framycetin, Kanamycin, Neomicin, Neomycin, Netilmicin, Streptomycin, Tobramycin, Azithromycin, Clarithromycin, Dirithromycin, Erythromycin, Roxithromycin, Telithromycin, Polymyxin-B, Colistin, Bacitracin, Tyrothricin Notrifurantoin, Furazolidone, Metronidazole, Tinidazole, Isoniazid, Pyrazinamide, Ethionamide, Nystatin, Amphotericin-B, Hamycin, Miconazole, Clotrimazole, Ketoconazole, Fluconazole, Rifampacin, Lincomycin, Clindamycin, Spectinomycin, Chloramphenicol, Clindamycin, Colistin, Fosfomycin, Loracarbef, Metronidazole, Nitrofurantoin, Polymyxin B, Polymyxin B Sulfate, Procain, Spectinomycin, Tinidazole, Trimethoprim, Ramoplanin, Teicoplanin, Vancomycin, Trimethoprim, Sulfamethoxazole, and/or Nitrofurantoin.

Vectors

The term "vector" as used herein refers to both expression and non-expression vectors and includes viral as well as non-viral vectors, including autonomous self-replicating circular plasmids. Where a recombinant microorganism or cell culture is described as hosting an "expression vector," this includes both extra-chromosomal circular DNA and DNA that has been incorporated into the host chromosome(s). Typical vectors of the disclosure are expression vectors. An expression vector contains multiple genetic elements positionally and sequentially oriented, i.e., operatively linked with other necessary elements such that nucleic acid molecule in the vector encoding the fusion proteins of the disclosure can be transcribed, and when necessary, translated in the host cells.

Any type of vector can be used in the context of the present disclosure, whether of plasmid or viral origin, whether it is an integrating or non-integrating vector. Such vectors are commercially available or described in the literature. Contemplated in the context of the disclosure are vectors for use in gene therapy (i.e. which are capable of delivering the nucleic acid molecule to a target cell) as well as expression vectors for use in recombinant techniques (i.e. which are capable for example of expressing the nucleic acid molecule of the disclosure in cultured host cells).

The vectors of the disclosure can function in prokaryotic or eukaryotic cells or in both (shuttle vectors). Suitable vectors include without limitation vectors derived from bacterial plasmids, bacteriophages, yeast episomes, artificial chromosomes, such as BAC, PAC, YAC, or MAC, and vectors derived from viruses such as baculoviruses, papovaviruses (e.g. SV40), herpes viruses, adenoviruses, adenovirus-associated viruses (AAV), poxviruses, foamy viruses, and retroviruses. Vectors may also be derived from combinations of these sources such as those derived from plasmid and bacteriophage genetic elements, e.g. cosmids and phagemids. Viral vectors can be replication-competent, conditionally replicative or replication-defective. In the case in which viral replication is defective, replication will occur in host cells providing functions that complement the defects.

Examples of suitable plasmids include but are not limited to those derived from pBR322 (Gibco BRL), pUC (Gibco BRL), pBluescript (Stratagene), p Poly (Lathe et al., 1987, Gene 57, 193-201), pTrc (Amann et al., 1988, Gene 69, 301-315) and pET 11d (Studier et al., 1990, Gene Expression Technology: Methods in Enzymology 185, 60-89). It is well known that the four of the plasmid can affect the expression efficiency, and it is typical that a large fraction of the vector be in supercoiled form. Examples of vectors for expression in yeast (e.g. *S. cerevisiae*) include pYepSec1 (Baldari et al., 1987, EMBO J. 6, 229-234), pMFa (Kujan et al., 1982, Cell 30, 933-943), pJRY88 (Schultz et al., 1987, Gene 54, 113-123), and pYES2 (Invitrogen Corporation, San Diego, Calif.). The vectors of the disclosure can also be derived from baculoviruses to be expressed in cultured insect cells (e.g. Sf 9 cells).

According to a typical embodiment of the disclosure, the nucleic acid molecules described herein are expressed by using mammalian expression vectors. Examples of mammalian expression vectors include pREP4, pCEP4 (Invitrogene), pCI (Promega), pCDM8 (Seed, 1987, Nature 329, 840) and pMT2PC (Kaufman et al., 1987, EMBO J. 6, 187-195). The expression vectors listed herein are provided by way of example only of some well-known vectors available to those of ordinary skill in the art. The person of ordinary skill in the art would be aware of other vectors suitable for maintenance, propagation or expression of the nucleic acid molecules described herein.

Moreover, the vector of the present disclosure may also comprise a marker gene in order to select or to identify the transfected cells (e.g. by complementation of a cell auxotrophy or by antibiotic resistance), stabilizing elements (e.g. cer sequence; Summers and Sherrat, 1984, Cell 36, 1097-1103), integrative elements (e.g. LTR viral sequences and transposons) as well as elements providing a self-replicating function and enabling the vector to be stably maintained in cells, independently of the copy number of the vector in the cell. Markers include tetracycline or ampicillin-resistance genes for prokaryotic host cells and dihydrofolate reductase or neomycin resistance for eukaryotic host cells. However, any marker that provides selection for a phenotypic trait will be effective. The self-replicating function may be provided by using a viral origin of replication and providing one or more viral replication factors that are required for replication mediated by that particular viral origin (WO 95/32299). Origins of replication and any replication factors may be obtained from a variety of viruses, including Epstein-Barr virus (EBV), human and bovine papilloma viruses and papovavirus BK.

Typical vectors of the present disclosure are viral vectors and especially adenoviral vectors, which have a number of well-documented advantages as vectors for gene therapy. The adenoviral genome consists of a linear double-stranded DNA molecule of approximately 36 kb carrying more than about thirty genes necessary to complete the viral cycle. The early genes are divided into 4 regions (E1 to E4) that are essential for viral replication (Pettersson and Roberts, 1986, In Cancer Cells (Vol 4): DNA Tumor Viruses, Botchan and Glodzicker Sharp Eds pp 37-47, Cold Spring Harbor Laboratory, Cold Spring Harbor, N.Y.; Halbert et al., 1985, J. Virol. 56, 250-257) with the exception of the E3 region, which is believed dispensable for viral replication based on the observation that naturally-occurring mutants or hybrid viruses deleted within the E3 region still replicate like wild-type viruses in cultured cells (Kelly and Lewis, 1973, J. Virol. 12, 643-652). The E1 gene products encode proteins responsible for the regulation of transcription of the viral genome. The E2 gene products are required for initiation and chain elongation in viral DNA synthesis. The proteins encoded by the E3 prevent cytolysis by cytotoxic T cells and tumor necrosis factor (Wold and Gooding, 1991, Virology 184, 1-8). The proteins encoded by the E4 region are involved in DNA replication, late gene expression and splicing and host cell shut off (Halbert et al., 1985, J. Virol. 56, 250-257). The late genes (L1 to L5) encode in their majority the structural proteins constituting the viral capsid. They overlap at least in part with the early transcription units and are transcribed from a unique promoter (MLP for Major Late Promoter). In addition, the adenoviral genome carries at both extremities cis-acting 5' and 3' ITRs (Inverted Terminal Repeat) and the encapsidation region, both essential for DNA replication. The ITRs harbor origins of DNA replication whereas the encapsidation region is required for the packaging of adenoviral DNA into infectious particles.

The adenoviral vectors for use in accordance with the present disclosure, typically infects mammalian cells. It can be derived from any human or animal source, in particular canine (e.g. CAV-1 or CAV-2; Genbank ref CAV1GENOM and CAV77082 respectively), avian (Genbank ref AAVEDS-DNA), bovine (such as BAV3; Seshidhar Reddy et al., 1998, J. Virol. 72, 1394-1402), murine (Genbank ref ADRMUS-MAV1), ovine, feline, porcine or simian adenovirus or alternatively from a hybrid thereof. Any serotype can be employed from the adenovirus serotypes 1 through 51. For instance, an adenovirus can be of subgroup A (e.g. serotypes 12, 18, and 31), subgroup B (e.g. serotypes 3, 7, 11, 14, 16, 21, 34, and 35), subgroup C (e.g. serotypes 1, 2, 5, and 6), subgroup D (e.g. serotypes 8, 9, 10, 13, 15, 17, 19, 20, 22-30, 32, 33, 36-39, and 42-47), subgroup E (serotype 4), subgroup F (serotypes 40 and 41), or any other adenoviral serotype. However, the human adenoviruses of the B or C sub-group are typical and especially adenoviruses 2 (Ad2), 5 (Ad5) and 35 (Ad35). Generally speaking, adenoviral stocks that can be employed as a source of the cited adenovirus are currently available from the American Type Culture Collection (ATCC, Rockville, Md.), or from any other source. Moreover, such adenoviruses have been the subject of numerous publications describing their sequence, organization and biology, allowing the artisan to apply them. Adenoviral vectors, methods of producing adenoviral vectors, and methods of using adenoviral vectors are disclosed, for example in U.S. Pat. No. 6,133,028, U.S. Pat. No. 6,040,174, U.S. Pat. No. 6,110,735, U.S. Pat. No. 6,399,587, WO 00/50573 and EP 1016711 for group C adenoviral vectors and for example in U.S. Pat. No. 6,492,169 and WO 02/40665 for non-group C adenoviral vectors.

In certain embodiments, the adenoviral vector of the present disclosure is replication-competent. The term "replication-competent" as used herein refers to an adenoviral vector capable of replicating in a host cell in the absence of any trans-complementation. In the context of the present disclosure, this term also encompasses replication-selective or conditionally-replicative adenoviral vectors which are engineered to replicate better or selectively in cancer or hyperproliferative host cells. Examples of such replication-competent adenoviral vectors are well known in the art and readily available to those skill in the art (see, for example, Hernandez-Alcoceba et al., 2000, Human Gene Ther. 11, 2009-2024; Nemunaitis et al., 2001, Gene Ther. 8, 746-759; Alemany et al., 2000, Nature Biotechnology 18, 723-727).

Replication-competent adenoviral vectors according to the disclosure can be a wild-type adenovirus genome or can be derived therefrom by introducing modifications into the viral genome, e.g., for the purpose of generating a conditionally-replicative adenoviral vector. Such modification(s) include the deletion, insertion and/or mutation of one or more nucleotide(s) in the coding sequences and/or the regulatory sequences. Typical modifications are those that render said replication-competent adenoviral vector dependent on cellular activities specifically present in a tumor or cancerous cell. In this regard, viral gene(s) that become dispensable in tumor cells, such as the genes responsible for activating the cell cycle through p53 or Rb binding, can be completely or partially deleted or mutated. By way of illustration, such conditionally-replicative adenoviral vectors can be engineered by the complete deletion of the adenoviral MB gene encoding the 55 kDa protein or the complete deletion of the MB region to abrogate p53 binding (see for example U.S. Pat. No. 5,801,029 and U.S. Pat. No. 5,846,945). This prevents the virus from inactivating tumor suppression in normal cells, which means that the virus cannot replicate. However, the virus will replicate and lyse cells that have shut off p53 or Rb expression through oncogenic transformation. As another example, the complete deletion of the E1A region makes the adenoviral vector dependent on intrinsic or IL-6-induced E1A-like activities. Optionally, an inactivating mutation may also be introduced in the E1A region to abrogate binding to the Rb. Rb defective mutation/deletion is typically introduced within the E1A CR1 and/or CR2 domain (see for example WO00/24408). In a second strategy optionally or in combination to the first approach, native viral promoters controlling transcription of the viral genes can be replaced with tissue or tumor-specific promoters. By way of illustration, regulation of the E1A and/or the E1B genes can be placed under the control of a tumor-specific promoter such as the PSA, the kallikrein, the probasin, the AFP, the a-fetoprotein or the telomerase reverse transcriptase (TERT) promoter (see for example U.S. Pat. No. 5,998,205, WO 99/25860, U.S. Pat. No. 5,698,443 and WO 00/46355) or a cell-cycle specific promoter such as E2F-1 promoter (WO00/15820 and WO01/36650). Typical in this context is the exemplary vector designated ONYX-411 which combines a Rb defective deletion of 8 amino acid residues within the MA CR2 domain and the use of E2F-1 promoter to control expression of both the E1A and E4 viral genes.

In certain embodiments, the adenoviral vector of the disclosure is replication-defective. Replication-defective adenoviral vectors are known in the art and can be defined as being deficient in one or more regions of the adenoviral genome that are essential to the viral replication (e.g., E1, E2 or E4 or combination thereof), and thus unable to propagate in the absence of trans-complementation (e.g., provided by either complementing cells or a helper virus). The replication-defective phenotype is obtained by introducing modifications in the viral genome to abrogate the function of one or more viral gene(s) essential to the viral replication. Typical replication-defective vectors are E1-deleted, and thus defective in E1 function. Such E1-deleted adenoviral vectors include those described in U.S. Pat. No. 6,063,622; U.S. Pat. No. 6,093,567; WO 94/28152; WO 98/55639 and EP 974 668 (the disclosures of all of these publications are hereby incorporated herein by reference). A typical E1 deletion covers approximately the nucleotides (nt) 459 to 3328 or 459 to 3510, by reference to the sequence of the human adenovirus type 5 (disclosed in the Genbank under the accession number M 73260 and in Chroboczek et al., 1992, Virol. 186, 280-285).

Furthermore, the adenoviral backbone of the vector may comprise modifications (e.g. deletions, insertions or mutations) in additional viral region(s), to abolish the residual synthesis of the viral antigens and/or to improve long-term expression of the nucleic acid molecules in the transduced cells (see for example WO 94/28152; Lusky et al., 1998, J. Virol 72, 2022-2032; Yeh et al., 1997, FASEB J. 11, 615-623). In this context, the present disclosure contemplates the use of adenoviral vectors lacking E1, or E1 and E2, or E1 and E3, or E1 and E4, or E1 and E2 and E3, or E1 and E2 and E4, or E1 and E3 and E4, or E1 and E2 and E3 and E4 functions. An adenoviral vector defective for E2 function may be deleted of all or part of the E2 region (typically within the E2A or alternatively within the E2B or within both the E2A and the E2B regions) or comprises one or more mutations, such as the thermosensitive mutation of the DBP (DNA Binding Protein) encoding gene (Ensinger et al., J. Virol. 10 (1972), 328-339). The adenoviral vector may also be deleted of all or part of the E4 region (see, for example, EP 974 668 and WO 00/12741). An exemplary E4 deletion covers approximately the nucleotides from position 32994 to position 34998, by reference to the sequence of the human adenovirus type 5. In addition, deletions within the non-essential E3 region (e.g. from Ad5 position 28597 to position 30469) may increase the cloning capacity, but it may be advantageous to retain the E3 sequences coding for gp19k, 14.7K and/or RID allowing to escape the host immune system (Gooding et al., 1990, Critical Review of Immunology 10, 53-71) and inflammatory reactions (EP 00 440 267.3). It is also conceivable to employ a minimal (or gutless) adenoviral vector which lacks all functional genes including early (E1, E2, E3 and E4) and late genes (L1, L2, L3, L4 and L5) with the exception of cis-acting sequences (see for example Kovesdi et al., 1997, Current Opinion in Biotechnology 8, 583-589; Yeh and Perricaudet, 1997, FASEB 11, 615-623; WO 94/12649; and WO 94/28152). The replication-deficient adenoviral vector may be readily engineered by one skilled in the art, taking into consideration the required minimum sequences, and is not limited to these exemplary embodiments.

The nucleic acid molecule of the present disclosure can be inserted in any location of the adenoviral genome, with the exception of the cis-acting sequences. Typically, it is inserted in replacement of a deleted region (E1, E3 and/or E4), with a special preference for the deleted E1 region. In addition, the expression cassette may be positioned in sense or antisense orientation relative to the natural transcriptional direction of the region in question.

A retroviral vector is also suitable in the context of the present disclosure. Retroviruses are a class of integrative viruses which replicate using a virus-encoded reverse transcriptase, to replicate the viral RNA genome into double stranded DNA which is integrated into chromosomal DNA of the infected cells. The numerous vectors described in the literature may be used within the framework of the present disclosure and especially those derived from murine leukemia viruses, especially Moloney (Gilboa et al., 1988, Adv. Exp. Med. Biol. 241, 29) or Friend's FB29 strains (WO 95/01447). Generally, a retroviral vector is deleted of all or part of the viral genes gag, pol and env and retains 5' and 3' LTRs and an encapsidation sequence. These elements may be modified to increase expression level or stability of the retroviral vector. Such modifications include the replacement of the retroviral encapsidation sequence by one of a retrotransposon such as VL30 (U.S. Pat. No. 5,747,323). The nucleic acid molecule of the disclosure can be inserted downstream of the encapsidation sequence, typically in opposite direction relative to the retroviral genome.

A poxviral vector is also suitable in the context of the present disclosure. Poxviruses are a group of complex enveloped viruses that distinguish from the above-mentioned viruses by their large DNA genome and their cytoplasmic site of replication. The genome of several members of poxyiridae has been mapped and sequenced. It is a double-stranded DNA of approximately 200 kb coding for about 200 proteins of which approximately 100 are involved in virus assembly. In the context of the present disclosure, a poxyiral vector may be obtained from any member of the poxyiridae, in particular canarypox, fowlpox and vaccinia virus, the latter being typical. Suitable vaccinia viruses include without limitation the Copenhagen strain (Goebel et al., 1990, Virol. 179, 247-266 and 517-563; Johnson et al., 1993, Virol. 196, 381-401), the Wyeth strain and the modified Ankara (MVA) strain (Antoine et al., 1998, Virol. 244, 365-396). The general conditions for constructing poxvirus comprising a nucleic acid molecule are well known in the art (see for example EP 83 286; EP 206 920 for Copenhagen vaccinia viruses and Mayr et al., 1975, Infection 3, 6-14; Sutter and Moss, 1992, Proc. Natl. Acad. Sci. USA 89, 10847-10851, U.S. Pat. No. 6,440,422 for MVA viruses). The nucleic acid molecule of the present disclosure is typically inserted within the poxyiral genome in a non-essential locus, such as non-coding intergenic regions or any gene for which inactivation or deletion does not significantly impair viral growth and replication. Thymidine kinase gene is particularly appropriate for insertion in Copenhagen vaccinia viruses (Hruby et al., 1983, Proc. Natl. Acad. Sci. USA 80, 3411-3415; Weir et al., 1983, J. Virol. 46, 530-537). As far as MVA is concerned, insertion of the nucleic acid molecule can be performed in any of the excisions I to VII, and typically in excision H or III (Meyer et al., 1991, J. Gen. Virol. 72, 1031-1038; Sutter et al., 1994, Vaccine 12, 1032-1040) or in D4R locus. For fowlpox virus, although insertion within the thymidine kinase gene may be considered, the nucleic acid molecule is typically introduced into a non-coding intergenic region (see for example EP 314 569 and U.S. Pat. No. 5,180,675). One may also envisage insertion in an essential viral locus provided that the defective function be supplied in trans, via a helper virus or by expression in the producer cell line. Suitable poxyiral vectors can be readily generated from wild type poxviruses available in recognized collections such as ATCC (fowlpox ATCC VR-251, monkey pox ATCC VR-267, swine pox ATCC VR-363, canarypox ATCC VR-111, cowpox ATCC VR-302) or ICTV (Canberra, Australia) (Copenhagen virus code 58.1.1.0.001; GenBank accession number M35027).

In certain embodiments, the vectors of the disclosure comprise the nucleic acid molecule of the disclosure in a form suitable for its expression in a host cell or organism, which means that the nucleic acid molecule is placed under the control of one or more regulatory sequences, selected on the basis of the vector type and/or host cell, which is operatively linked to the nucleic acid molecule to be expressed. As used herein, the term "regulatory sequence" refers to any sequence that allows, contributes or modulates the functional regulation of the nucleic acid molecule, including replication, duplication, transcription, splicing, translation, stability and/or transport of the nucleic acid or one of its derivative (i.e. mRNA) into the host cell or organism. In the context of the disclosure, this term encompasses promoters, enhancers and other expression control elements (e.g., polyadenylation signals and elements that affect mRNA stability). "Operably linked" is intended to mean that the nucleic acid molecule of interest is linked to the regulatory sequence(s) in a manner which allows for expression of the nucleic acid molecule (e.g., in a host cell or organism). It will be appreciated by those skilled in the art that the design of the expression vector can depend on such factors as the choice of the host cell to be transformed, the level of expression of protein desired, etc.

Regulatory sequences include promoters which direct constitutive expression of a nucleic acid molecule in many types of host cell and those which direct expression of the nucleotide sequence only in certain host cells (e.g., tissue-specific regulatory sequences) or in response to specific events or exogenous factors (e.g. by temperature, nutrient additive, hormone or other ligand).

Suitable regulatory sequences useful in the context of the present disclosure include, but are not limited to, the left promoter from bacteriophage lambda, the lac, TRP, and TAC promoters from *E. coli*, the early and late promoters from SV40, the cytomegalovirus (CMV) immediate early promoter or enhancer (Boshart et al., 1985, Cell 41, 521-530), the adenovirus early and late promoters, the phosphoglycero kinase (PGK) promoter (Hitzeman et al., 1983, Science 219, 620-625; Adra et al., 1987, Gene 60, 65-74), the thymidine kinase (TK) promoter of herpes simplex virus (HSV)-1 and retroviral long-terminal repeats (e.g. MoMuLV and Rous sarcoma virus (RSV) LTRs). Suitable promoters useful to drive expression of the nucleic acid molecule of the disclosure in a poxyiral vector include the 7.5K, H5R, TK, p28, p11 or K1L promoters of vaccinia virus. Alternatively, one may use a synthetic promoter such as those described in Chakrabarti et al. (1997, Biotechniques 23, 1094-1097), Hammond et al. (1997, J. Virological Methods 66, 135-138) and Kumar and Boyle (1990, Virology 179, 151-158) as well as chimeric promoters between early and late poxyiral promoters.

Inducible promoters are regulated by exogenously supplied compounds, and include, without limitation, the zinc-inducible metallothionein (MT) promoter (Mc Ivor et al., 1987, Mol. Cell. Biol. 7, 838-848), the dexamethasone (Dex)-inducible mouse mammary tumor virus (MMTV) promoter, the T7 polymerase promoter system (WO 98/10088), the ecdysone insect promoter (No et al., 1996, Proc. Natl. Acad. Sci. USA 93, 3346-3351), the tetracycline-repressible promoter (Gossen et al., 1992, Proc. Natl. Acad. Sci. USA 89, 5547-5551), the tetracycline-inducible promoter (Kim et al., 1995, J. Virol. 69, 2565-2573), the RU486-inducible promoter (Wang et al., 1997, Nat. Biotech. 15, 239-243 and Wang et al., 1997, Gene Ther. 4, 432-441) and the rapamycin-inducible promoter (Magari et al., 1997, J. Clin. Invest. 100, 2865-2872).

The regulatory sequences in use in the context of the present disclosure can also be tissue-specific to drive expression of the nucleic acid molecule in the tissues where therapeutic benefit is desired. Exemplary liver-specific regulatory sequences include but are not limited to those of HMG-CoA reductase (Luskey, 1987, Mol. Cell. Biol. 7, 1881-1893); sterol regulatory element 1 (SRE-1; Smith et al., 1990, J. Biol. Chem. 265, 2306-2310); albumin (Pinkert et al., 1987, Genes Dev. 1, 268-277); phosphoenol pyruvate carboxy kinase (PEPCK) (Eisenberger et al., 1992, Mol. Cell. Biol. 12, 1396-1403); human C-reactive protein (CRP) (Li et al., 1990, J. Biol. Chem. 265, 4136-4142); human glucokinase (Tanizawa et al., 1992, Mol. Endocrinology. 6, 1070-1081); cholesterol 7-alpha hydroylase (CYP-7) (Lee et al., 1994, J. Biol. Chem. 269, 14681-14689); alpha-1 anti-trypsin (Ciliberto et al., 1985, Cell 41, 531-540); insulin-like growth factor binding protein (IGFBP-1) (Babajko et al., 1993, Biochem Biophys. Res. Comm. 196, 480-486); human transferrin (Mendelzon et al., 1990, Nucl. Acids Res. 18, 5717-5721); collagen type I (Houglum et al., 1994, J. Clin. Invest. 94, 808-814) and FIX (U.S. Pat. No. 5,814,716) genes. Exemplary prostate-specific regulatory sequences include but are not limited to those of the prostatic acid phosphatase (PAP) (Balms et al., 1994, Biochim. Biophys. Acta. 1217, 188-194); prostatic secretory protein 94 (PSP 94) (Nolet et al., 1991, Biochim. Biophys. Acta 1089, 247-249); prostate specific antigen complex (Kasper et al., 1993, J. Steroid Biochem. Mol. Biol. 47, 127-135); human glandular kallikrein (hgt-1) (Lilja et al., 1993, World J. Urology 11, 188-191) genes. Exemplary pancreas-specific regulatory sequences include but are not limited to those of pancreatitis associated protein promoter (Dusetti et al., 1993, J. Biol. Chem. 268, 14470-14475); elastase 1 transcriptional enhancer (Kruse et al., 1993, Genes and Development 7, 774-786); pancreas specific amylase and elastase enhancer/promoter (Wu et al., 1991, Mol. Cell. Biol. 11, 4423-4430; Keller et al., 1990, Genes & Dev. 4, 1316-1321); pancreatic cholesterol esterase gene promoter (Fontaine et al., 1991, Biochemistry 30, 7008-7014) and the insulin gene promoter (Edlund et al., 1985, Science 230, 912-916). Exemplary neuron-specific regulatory sequences include but are not limited to neuron-specific enolase (NSE) (Forss-Petter et al., 1990, Neuron 5, 187-197) and the neurofilament (Byrne and Ruddle, 1989, Proc. Natl. Acad. Sci. USA 86, 5473-5477) gene promoters. Exemplary regulatory sequences for expression in the brain include but are not limited to the neurofilament heavy chain (NF-H) promoter (Schwartz et al., 1994, J. Biol. Chem. 269, 13444-13450). Exemplary lymphoid-specific regulatory sequences include but are not limited to the human CGL1/granzyme B promoter (Hanson et al., 1991, J. Biol. Chem. 266, 24433-24438); terminal deoxy transferase (TdT), lymphocyte specific tyrosine protein kinase (p561ck) promoters (Lo et al., 1991, Mol. Cell. Biol. 11, 5229-5243); the human CD2 promoter/enhancer (Lake et al., 1990, EMBO J. 9, 3129-3136), the human NK and T cell specific activation (NKG5) (Houchins et al., 1993, Immunogenetics 37, 102-107), T cell receptor (Winoto and Baltimore, 1989, EMBO J. 8, 729-733) and immunoglobulin (Banerji et al., 1983, Cell 33, 729-740; Queen and Baltimore, 1983, Cell 33, 741-748) promoters. Exemplary colon-specific regulatory sequences include but are not limited to pp 60c-src tyrosine kinase (Talamonti et al., 1993, J. Clin. Invest 91, 53-60); organ-specific neoantigens (OSNs), mw 40 kDa (p40) (Ilantzis et al., 1993, Microbiol. Immunol. 37, 119-128); and colon specific antigen-P promoter (Sharkey et al., 1994, Cancer 73, 864-877) promoters. Exemplary regulatory sequences for expression in mammary gland and breast cells include but are not limited to the human alpha-lactalbumin (Thean et al., 1990, British J. Cancer. 61, 773-775) and milk whey (U.S.

Pat. No. 4,873,316) promoters. Exemplary muscle-specific regulatory sequences include but are not limited to SM22 (WO 98/15575; WO 97/35974), the desmin (WO 96/26284), mitochondrial creatine kinase (MCK) promoters, and the chimeric promoter disclosed in EP 1310561. Exemplary lung-specific regulatory sequences include but are not limited to the CFTR and surfactant promoters.

Additional promoters suitable for use in this disclosure can be taken from genes that are preferentially expressed in proliferative tumor cells. Such genes can be identified for example by display and comparative genomic hybridization (see for example U.S. Pat. Nos. 5,759,776 and 5,776,683). Exemplary tumor specific promoters include but are not limited to the promoters of the MUC-1 gene overexpressed in breast and prostate cancers (Chen et al., 1995, J. Clin. Invest. 96, 2775-2782), of the Carcinoma Embryonic Antigen (CEA)-encoding gene overexpressed in colon cancers (Schrewe et al., 1990, Mol. Cell. Biol. 10, 2738-2748), of the ERB-2 encoding gene overexpressed in breast and pancreas cancers (Harris et al., 1994, Gene Therapy 1, 170-175), of the alpha-foetoprotein gene overexpressed in liver cancers (Kanai et al., 1997, Cancer Res. 57, 461-465), of the telomerase reverse transcriptase (TERT) (WO99/27113, WO 02/053760 and Horikawa et al., 1999, Cancer Res. 59, 826), hypoxia-responsive element (HRE), autocrine motility factor receptor, L plasmin and hexokinase II.

Those skilled in the art will appreciate that the regulatory elements controlling the expression of the nucleic acid molecule of the disclosure may further comprise additional elements for proper initiation, regulation and/or termination of transcription and translation into the host cell or organism. Such additional elements include but are not limited to non-coding exon/intron sequences, transport sequences, secretion signal sequences, nuclear localization signal sequences, IRES, polyA transcription termination sequences, tripartite leader sequences, sequences involved in replication or integration. Illustrative examples of introns suitable in the context of the disclosure include those isolated from the genes encoding alpha or beta globin (i.e. the second intron of the rabbit beta globin gene; Green et al., 1988, Nucleic Acids Res. 16, 369; Karasuyama et al., 1988, Eur. J. Immunol. 18, 97-104), ovalbumin, apolipoprotein, immunoglobulin, factor IX, and factor VIII, the SV40 16S/19S intron (Okayma and Berg, 1983, Mol. Cell. Biol. 3, 280-289) as well as synthetic introns such as the intron present in the pCI vector (Promega Corp, pCI mammalian expression vector E1731) made of the human beta globin donor fused to the mouse immunoglobin. Where secretion of the fusion protein is desired, appropriate secretion signals are incorporated into the vector. The signal sequence can be endogenous to the fusion protein or heterologous to both entities involved in the fusion protein. The person of ordinary skill in the art would be aware of the numerous regulatory sequences that are useful in expression vectors.

In addition, the vector of the disclosure can further comprise one or more transgenes (i.e. a gene of interest to be expressed together with the nucleic acid molecule of the disclosure in a host cell or organism). Desirably, the expression of the transgene has a therapeutic or protective activity to the disease or illness condition for which the vector of the present disclosure is being given. Suitable transgenes include without limitation genes encoding (i) tumor proliferation inhibitors and/or (ii) at least one specific antigen against which an immune response is desired. In a typical form of the present disclosure, the transgene product and the fusion protein act synergistically in the induction of immune responses or in providing a therapeutic (e.g. antitumoral) benefit. Accordingly, such combinations are not only suitable for immunoprophylaxis of diseases, but surprisingly also for immunotherapy of diseases such as viral, bacterial or parasitic infections, and also chronic disorders such as cancers.

Tumor proliferation inhibitors act by directly inhibiting cell growth, or killing the tumor cells. Representative examples of tumor proliferation inhibitors include toxins and suicide genes. Representative examples of toxins include without limitation ricin (Lamb et al., 1985, Eur. J. Biochem. 148, 265-270), diphtheria toxin (Tweten et al., 1985, J. Biol. Chem. 260, 10392-10394), cholera toxin (Mekalanos et al., 1983, Nature 306, 551-557; Sanchez and Holmgren, 1989, Proc. Natl. Acad. Sci. USA 86, 481-485), gelonin (Stirpe et al., 1980, J. Biol. Chem. 255, 6947-6953), antiviral protein (Barbieri et al., 1982, Biochem. J. 203, 55-59; Irvin et al., 1980, Arch. Biochem. Biophys. 200, 418-425), tritin, Shigella toxin (Calderwood et al., 1987, Proc. Natl. Acad. Sci. USA 84, 4364-4368; Jackson et al., 1987, Microb. Path. 2, 147-153) and *Pseudomonas* exotoxin A (Carroll and Collier, 1987, J. Biol. Chem. 262, 8707-8711).

Specific antigens are typically those susceptible to confer an immune response, specific and/or nonspecific, antibody and/or cell-mediated, against a given pathogen (virus, bacterium, fungus or parasite) or against a non-self antigen (e.g. a tumor-associated antigen). Typically, the selected antigen comprises an epitope that binds to, and is presented onto the cell surface by MHC class I proteins. Representative examples of specific antigens include without limitation: antigen(s) of the Hepatitis B surface antigen are well known in the art and include, inter alia, those PreS1, Pars2 S antigens set forth described in European Patent applications EP 414 374; EP 304 578, and EP 198 474. Antigens of the Hepatitis C virus including any immunogenic antigen or fragment thereof selected from the group consisting of the Core (C), the envelope glycoprotein E1, E2, the non-structural polypeptide NS2, NS3, NS4 (NS4a and/or NS4b), NS5 (NS5a and/or NS5b) or any combination thereof (e.g. NS3 and NS4, NS3 and NS4 and NS5b) Antigen(s) of the HIV-1 virus, especially gp120 and gp160 (as described WO 87/06260). Antigen(s) derived from the Human Papilloma Virus (HPV) considered to be associated with genital warts (HPV 6 or HPV 11 and others), and cervical cancer (HPV16, HPV18, HPV 31, HPV-33 and others). Contemplated HPV antigens are selected among the group consisting of E5, E6, E7, L1, and L2 either individually or in combination (see for example WO 94/00152, WO 94/20137, WO 93/02184, WO 90/10459, and WO 92/16636). Contemplated in the context of the disclosure are membrane anchored forms of non-oncogenic variants of the early HPV-16 E6 and/or E7 antigens (as described in WO 99/03885) that are particularly suitable to achieve an anti-tumoral effect against an HPV-associated cancer. Antigens from parasites that cause malaria. For example, typical antigens from *Plasmodia falciparum* include RTS (WO 93/10152), and TRAP (WO 90/01496). Other plasmodia antigens that are likely candidates are *P. falciparum*. MSP1, AMA1, MSP3, EBA, GLURP, RAPT, RAP2, Sequestrin, PfEMP1, Pf332, LSA1, LSA3, STARP, SALSA, PfEXP1, Pfs25, Pfs28, PFS27125, Pfs16, Pfs48/45, Pfs230 and their analogues in other *Plasmodium* species.

Other suitable antigens include tumour-associated antigens such as those associated with prostrate, breast, colorectal, lung, pancreatic, renal, liver, bladder, sarcoma or melanoma cancers. Exemplary antigens include MAGE 1, 3 and MAGE 4 or other MAGE antigens (WO 99/40188), PRAME, BAGE, Lage (also known as NY Eos 1) SAGE and HAGE (WO 99/53061) or GAGE (Robbins and Kawakami, 1996. Current Opinions in Immunol. 8, pps 628-636). Other suitable tumor-associated antigens include those known as prostase, including Prostate specific antigen (PSA), PAP, PSCA, PSMA. Prostase nucleotide sequence and deduced polypeptide sequence and homologs are disclosed in Ferguson, et al. (1999, Proc. Natl. Acad. Sci. USA. 96, 3114-3119) and WO 98/12302 WO 98/20117 and WO 00/04149. Other suitable tumour-associated antigens include those associated with breast cancer, such as BRCA-1, BRCA-2 and MUC-1 (see for example WO 92/07000).

The transgene in use in the present disclosure is placed under the control of appropriate regulatory elements to permit its expression in the selected host cell or organism in either a constitutive or inducible fashion. The choice of such regulatory elements is within the reach of the skilled artisan. It is typically selected from the group consisting of constitutive, inducible, tumor-specific and tissue-specific promoters as described above in connection with the expression of the fusion protein of the present disclosure. In one example, the transgene is placed under control of the CMV promoter to ensure high level expression.

The transgene in use in the present disclosure can be inserted in any location of the vector. According to one alternative, it is placed typically not in close proximity of the nucleic acid molecule of the disclosure. According to another alternative it can be placed in antisense orientation with respect to the nucleic acid molecule, in order to avoid transcriptional interference between the two expression cassettes. For example, in an adenoviral genome, the transgene can be inserted in a different deleted region with respect to the nucleic acid molecule of the disclosure (E1, E3 and/or E4) or in the same deleted region as said nucleic acid molecule but in antisense orientation to one another.

Introducing the nucleic acid molecule of the disclosure into a vector backbone can proceed by any genetic engineering strategy appropriate in the art for any kind of vectors such as by methods described in Sambrook et al. (2001, Molecular Cloning—A Laboratory Manual, Cold Spring Harbor Laboratory). Typically, for the introduction of the nucleic acid molecule into an adenoviral vector, a bacterial plasmid comprising the fusion-encoding nucleic acid molecule is engineered to replace an adenoviral gene required for replication or assembly (e.g. E1) with the substitute nucleic acid molecule. The plasmid is then used as a shuttle vector, and combined with a second plasmid containing the complementary portion of the adenovirus genome, permitting homologous recombination to occur by virtue of overlapping adenovirus sequences in the two plasmids. The recombination can be done directly in a suitable mammalian host (such as 293 as described in Graham and Prevect, 1991, Methods in Molecular Biology, Vol 7"Gene Transfer and Expression Protocols"; Ed E. J. Murray, The Human Press Inc, Clinton, N.J.), or else in yeast YAC clones or E. coli (as described in WO 96/17070). The completed adenovirus genome is subsequently transfected into mammalian host cells for replication and viral encapsidation.

The present disclosure also encompasses vectors of the disclosure or particles thereof that have been modified to allow preferential targeting of a particular target cell. A characteristic feature of targeted vectors/particles of the disclosure (of both viral and non-viral origins, such as and lipid-complexed vectors) is the presence at their surface of a targeting moiety capable of recognizing and binding to a cellular and surface-exposed component. Such targeting moieties include without limitation chemical conjugates, lipids, glycolipids, hormones, sugars, polymers (e.g. PEG, polylysine, PEI and the like), peptides, polypeptides (for example JTS1 as described in WO 94/40958), oligonucleotides, vitamins, antigens, lectins, antibodies and fragments thereof. They are typically capable of recognizing and binding to cell-specific markers, tissue-specific markers, cellular receptors, viral antigens, antigenic epitopes or tumor-associated markers. In this regard, cell targeting of adenoviruses can be carried out by genetic modification of the viral gene encoding the capsid polypeptide present on the surface of the virus (e.g. fiber, penton and/or pIX). Examples of such modifications are described in literature (for example in Wickam et al., 1997, J. Viral. 71, 8221-8229; Amberg et al., 1997, Virol. 227, 239-244; Michael et al., 1995, Gene Therapy 2, 660-668; WO 94/10323, EP 02 360204 and WO 02/96939). To illustrate, inserting a sequence coding for EGF within the sequence encoding the adenoviral fiber will allow to target EGF receptor expressing cells. The modification of poxyiral tropism can also be achieved as described in EP 1 146 125. Other methods for cell specific targeting can be achieved by the chemical conjugation of targeting moieties at the surface of a viral particle.

In certain embodiments, the present disclosure relates to infectious viral particles comprising the above-described nucleic acid molecules or vectors of the present disclosure.

The disclosure also relates to a process for producing an infectious viral particle, comprising the steps of: (a) introducing the viral vector of the disclosure into a suitable cell line, (b) culturing said cell line under suitable conditions so as to allow the production of said infectious viral particle, and (c) recovering the produced infectious viral particle from the culture of said cell line, and (d) optionally purifying said recovered infectious viral particle.

The vector containing the nucleic acid molecule of the disclosure can be introduced into an appropriate cell line for propagation or expression using well-known techniques readily available to the person of ordinary skill in the art. These include, but are not limited to, microinjection of minute amounts of DNA into the nucleus of a cell (Capechi et al., 1980, Cell 22, 479-488), CaPO.sub.4-mediated transfection (Chen and Okayama, 1987, Mol. Cell Biol. 7, 2745-2752), DEAE-dextran-mediated transfection, electroporation (Chu et al., 1987, Nucleic Acid Res. 15, 1311-1326), lipofection/liposome fusion (Feigner et al., 1987, Proc. Natl. Acad. Sci. USA 84, 7413-7417), particle bombardment (Yang et al., 1990, Proc. Natl. Acad. Sci. USA 87, 9568-9572), gene guns, transduction, infection (e.g. with an infective viral particle), and other techniques such as those found in Sambrook, et al. (Molecular Cloning: A Laboratory Manual, Cold Spring Harbor Laboratory, Cold Spring Harbor Laboratory Press, Cold Spring Harbor, N.Y., 2001).

When the vector of the disclosure is defective, the infectious particles are usually produced in a complementation cell line or via the use of a helper virus, which supplies in trans the non-functional viral genes. For example, suitable cell lines for complementing adenoviral vectors include the 293 cells (Graham et al., 1997, J. Gen. Virol. 36, 59-72) as well as the PER-C6 cells (Fallaux et al., 1998, Human Gene Ther. 9, 1909-1917) commonly used to complement the E1 function. Other cell lines have been engineered to complement doubly defective adenoviral vectors (Yeh et al., 1996, J. Virol. 70, 559-565; Krougliak and Graham, 1995, Human Gene Ther. 6, 1575-1586; Wang et al., 1995, Gene Ther. 2, 775-783; Lusky et al., 1998, J. Virol. 72, 2022-2033; WO94/28152 and WO97/04119). The infectious viral particles may be recovered from the culture supernatant but also from the cells after lysis and optionally are further purified according to standard techniques (chromatography, ultracentrifugation in a cesium chloride gradient as described for example in WO 96/27677, WO 98/00524, WO 98/22588, WO 98/26048, WO 00/40702, EP 1016700 and WO 00/50573).

The disclosure also relates to host cells which comprise the nucleic acid molecules, vectors or infectious viral particles of the disclosure described herein. For the purpose of the disclosure, the term "host cell" should be understood broadly without any limitation concerning particular organization in tissue, organ, or isolated cells. Such cells may be of a unique type of cells or a group of different types of cells and encompass cultured cell lines, primary cells and proliferative cells.

Host cells therefore include prokaryotic cells, lower eukaryotic cells such as yeast, and other eukaryotic cells such as insect cells, plant and higher eukaryotic cells, such as vertebrate cells and, with a special preference, mammalian (e.g. human or non-human) cells. Suitable mammalian cells include but are not limited to hematopoietic cells (totipotent, stem cells, leukocytes, lymphocytes, monocytes, macrophages, APC, dendritic cells, non-human cells and the like), pulmonary cells, tracheal cells, hepatic cells, epithelial cells, endothelial cells, muscle cells (e.g. skeletal muscle, cardiac muscle or smooth muscle) or fibroblasts. Typical host cells include *Escherichia coli, Bacillus, Listeria, Saccharomyces*, BHK (baby hamster kidney) cells, MDCK cells (Madin-Darby canine kidney cell line), CRFK cells (Crandell feline kidney cell line), CV-1 cells (African monkey kidney cell line), COS (e.g., COS-7) cells, chinese hamster ovary (CHO) cells, mouse NIH/3T3 cells, HeLa cells and Vero cells. Host cells also encompass complementing cells capable of complementing at least one defective function of a replication-defective vector of the disclosure (e.g. adenoviral vector) such as those cited above.

The host cell of the disclosure can contain more than one nucleic acid molecule, vector or infectious viral particle of the disclosure. Further it can additionally comprise a vector encoding a transgene, e.g. a transgene as described above. When more than one nucleic acid molecule, vector or infectious viral particle is introduced into a cell, the nucleic acid molecules, vectors or infectious viral particles can be introduced independently or co-introduced.

Moreover, according to a specific embodiment, the host cell of the disclosure can be further encapsulated. Cell encapsulation technology has been previously described (Tresco et al., 1992, ASAJO J. 38, 17-23; Aebischer et al., 1996, Human Gene Ther. 7, 851-860). According to said specific embodiment, transfected or infected eukaryotic host cells are encapsulated with compounds which form a microporous membrane and said encapsulated cells can further be implanted in vivo. Capsules containing the cells of interest may be prepared employing hollow microporous membranes (e.g. Akzo Nobel Faser A G, Wuppertal, Germany; Deglon et al. 1996, Human Gene Ther. 7, 2135-2146) having a molecular weight cutoff appropriate to permit the free passage of proteins and nutrients between the capsule interior and exterior, while preventing the contact of transplanted cells with host cells.

Still a further aspect of the present disclosure is a method for recombinantly producing the fusion protein, employing the vectors, infectious viral particles and/or host cells of the disclosure. The method for producing the fusion protein comprises introducing a vector or an infectious viral particle of the disclosure into a suitable host cell to produce a transfected or infected host cell, culturing in-vitro said transfected or infected host cell under conditions suitable for growth of the host cell, and thereafter recovering said fusion protein from said culture, and optionally, purifying said recovered fusion protein. It is expected that those skilled in the art are knowledgeable in the numerous expression systems available for expression of the fusion proteins of the disclosure in appropriate host cells.

The host cell of the disclosure is typically produced by transfecting/infecting a host cell with one or more recombinant molecules, (e.g. a vector of the disclosure) comprising one or more nucleic acid molecules of the present disclosure. Recombinant DNA technologies can be used to improve expression of the nucleic acid molecule in the host cell by manipulating, for example, the number of copies of the nucleic acid molecule within a host cell, the efficiency with which the nucleic acid molecule is transcribed, the efficiency with which the resultant transcripts are translated, the efficiency of post-translational modifications and the use of appropriate selection. Recombinant techniques useful for increasing the expression of nucleic acid molecules of the present disclosure include, but are not limited to, the use of high-copy number vectors, addition of vector stability sequences, substitution or modification of one or more transcriptional regulatory sequences (e.g., promoters, operators, enhancers), substitution or modification of translational regulatory sequences (e.g., ribosome binding sites, Shine-Dalgarno sequences), modification of nucleic acid molecule of the present disclosure to correspond to the codon usage of the host cell, and deletion of sequences that destabilize transcripts.

Host cells of the present disclosure can be cultured in conventional fermentation bioreactors, flasks, and petri plates. Culturing can be carried out at a temperature, pH and oxygen content appropriate for a given host cell. No attempts to describe in detail the various methods known for the expression of proteins in prokaryote and eukaryote cells will be made here. In one embodiment, the vector is a plasmid carrying the fusion-encoding nucleic acid molecule in operative association with appropriate regulatory elements. Typical host cells in use in the method of the disclosure are mammalian cell lines, yeast cells and bacterial cells.

Where the fusion protein is not secreted outside the producing cell or where it is not secreted completely, it can be recovered from the cell by standard disruption procedures, including freeze thaw, sonication, mechanical disruption, use of lysing agents and the like. If secreted, it can be recovered directly from the culture medium. The fusion protein can then be recovered and purified by well-known purification methods including ammonium sulfate precipitation, acid extraction, gel electrophoresis, reverse phase chromatography, size exclusion chromatography, ion exchange chromatography, affinity chromatography, phosphocellulose chromatography, hydrophobic-interaction chromatography, hydroxylapatite chromatography, lectin chromatography, or high performance liquid chromatography. The conditions and technology used to purify a particular fusion protein of the disclosure will depend on the synthesis method and on factors such as net charge, molecular weight, hydrophobicity, hydrophilicity and will be apparent to those having skill in the art. It is also understood that depending upon the host cell used for the recombinant production of the fusion proteins described herein, the fusion proteins can have various glycosylation patterns, or may be non-glycosylated (e.g. when produced in bacteria). In addition, the fusion protein may include an initial methionine in some cases as a result of a host-mediated process.

The fusion protein of the disclosure can be "purified" to the extent that it is substantially free of cellular material. The level of purification will be based on the intended use. The critical feature is that the preparation allows for the desired function of the fusion protein, even if in the presence of considerable amounts of other components. In some uses, "substantially free of cellular material" includes preparations of the fusion protein having less than about 30% (by dry weight) other proteins (i.e., contaminating proteins), typically less than about 20% other proteins, more typically less than about 10% other proteins, or even more typically less than about 5% other proteins. When the fusion protein is recombinantly produced, it can also be substantially free of culture medium, i.e., culture medium represents less than about 20% of the volume of the protein preparation.

Terms

As used herein, the term "conjugate" refers to molecular entities joined by covalent bonds or other arrangement that provides substantially irreversible binding under physiological conditions. For example, two proteins, isolated and/or purified polypeptide sequence, may be conjugated together by a linker polymer, e.g., amino acid, polypeptide sequence, ethylene glycol polymer. Two proteins may be conjugated together by linking one protein to a ligand and linking the second protein to a receptor, e.g., streptavidin and biotin or an antibody and an epitope.

As used herein, the term "combination with" when used to describe administration with an additional treatment means that the agent may be administered prior to, together with, or after the additional treatment, or a combination thereof.

As used herein, "subject" refers to any animal, typically a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

As used herein, "amino acid sequence" refers to an amino acid sequence of a protein molecule. An "amino acid sequence" can be deduced from the nucleic acid sequence encoding the protein. However, terms such as "polypeptide" or "protein" are not meant to limit the amino acid sequence to the deduced amino acid sequence, but include non-naturally occurring amino acids, post-translational modifications of the deduced amino acid sequences, such as amino acid deletions, additions, and modifications such as glycolsylations and addition of lipid moieties.

The term "a nucleic acid sequence encoding" a specified polypeptide refers to a nucleic acid sequence comprising the coding region of a gene or in other words the nucleic acid sequence which encodes a gene product. The coding region may be present in a cDNA, genomic DNA or RNA form. When present in a DNA form, the oligonucleotide, polynucleotide, or nucleic acid may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present disclosure may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

A "virus-like particle" refers to a particle comprising virion proteins but is substantially free of viral genetic material, e.g., viral RNA. Virus-like particles may contain viral proteins from different viruses. See e.g., Guo et al., Enhancement of mucosal immune responses by chimeric influenza HA/SHIV virus-like particles, Virology, 2003, 313(2):502-13. Virus-like particles may contain lipid membranes and may be constructed to express a variety of antigens on their particle surface ether by expression in viral vectors use to create the particles or by mixing the virus-like particle with an antigen or other polypeptide conjugated to a glycosylphosphatidyl-inositol anchor. See e.g. Skountzou et al., J. Virol. 81(3):1083-94; Derdak et al., PNAS, 2006, 103(35) 13144-13149; Poloso et al., Molecular Immunology, 2001, 38:803-816.

As used herein, the article "a" or "an" is intended to refer to one or more unless the context suggests otherwise.

Experimental

GIFT4 Gene and Protein.

The genes (cDNA) of murine IL-4 and GM-CSF were purchased from Invivogen (San-Diego, Calif.), and cloned into the bicistronic AP2 retrovector in a frame allowing the expression of both the chimeric transgenes and GIFT4 fusion proteins. One amino acid (Serine, S) serves as the bridge linker between the GM-CSF and IL-4 protein sequences. To build the three-dimensional structure of murine GIFT4 protein, the crystal structures of human GM-CSF and IL-4 were used as the templates for homology modeling on the software PROSPECT v2 (Oak Ridge National Laboratory, Oak Ridge, Tenn.). The GIFT4-encoding retroviral plasmid was introduced into the 293-GP2 packaging cells (Clontech, Mountain View, Calif.) following the manufacturer's instructions. The concentrated retroparticles encoding GIFT4 or GM-CSF or IL-4 genes were used to genetically modify 293T cells or B16F10 melanoma cells. 293T-GIFT4 cells or B16F0-GIFT4 cells were pooled together from positive single cell clone selections in the wells of a 96-well plate, confirmed by GIFT4 protein expression detected by ELISA.

GIFT4 Triggers B Cell Expansion.

In order to test the immune stimulatory function of GIFT4 fusokine, murine GIFT4 cDNA from parental GM-CSF and IL-4 cDNAs was cloned into an AP2 retrovirus vector, then transfected into 293T cells. The translated GIFT4 protein sequence is consistent of a single polypeptide chain of 282 amino acids (FIG. 1A) with a predicted 3D structure (FIG. 1B). AP2-GIFT4 vector-transfected 293T cells stably express abundant GIFT4 protein with a about 50 kDa of molecular weight (FIG. 1C). GIFT4 fusion protein has strong bioactivities to induce proliferation of GM-CSF-responder JAWSII cells (FIG. 1D) and IL-4-dependent CT.h4S cells (FIG. 1E).

Figure 2B:
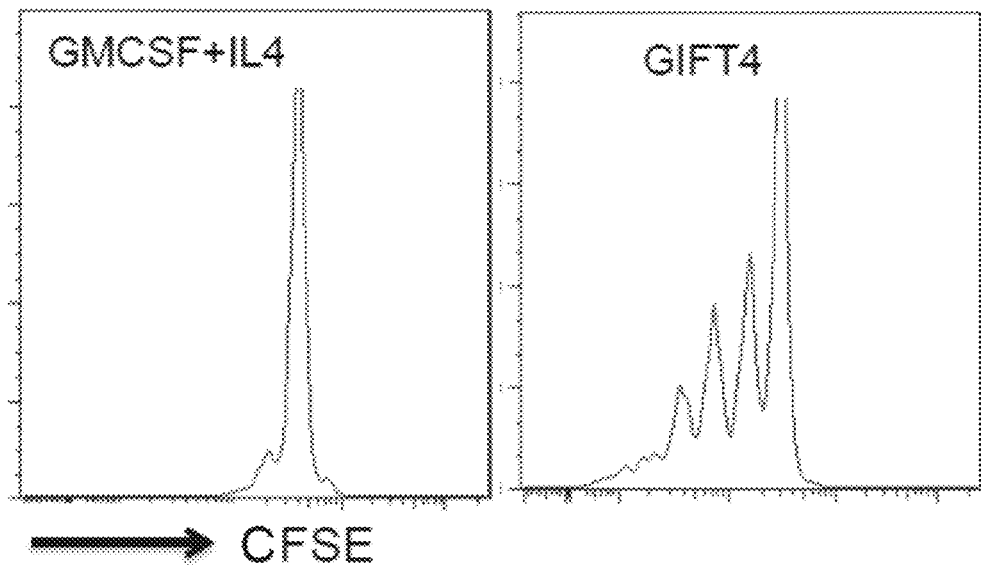
FIG. 2B shows data where cells were labeled with CFSE dye. Cells division cycles were presented as individual peaks.
Figure 2C:
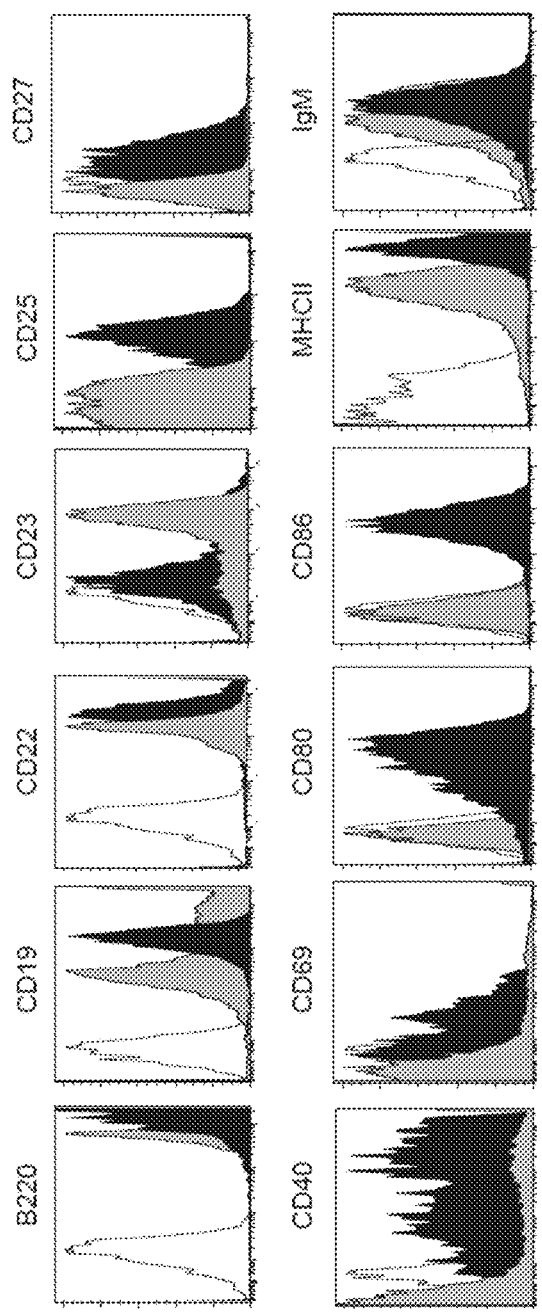
FIG. 2C shows sata on surface markers of GIFT4-treated B cells (black color filled) compared to untreated B cells (gray color filled) or antibody isotype control (black line).
Figure 2D:
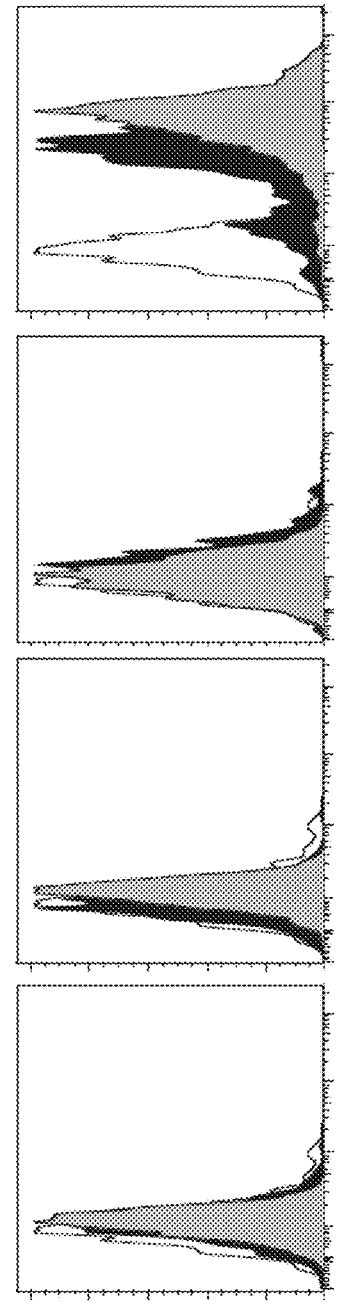
FIG. 2D shows data indicating down-regulation of co-stimulatory molecules CD80 and CD86, and immunoglobulin switch from IgM to IgG in B cells after BCR cross-linking with anti-mouse IgM antibodies in presence of GIFT4 (black color filled). Combined recombinant GM-CSF and IL-4 (gray color filled) served as control. Black line only is the antibody isotype control.
Figure 9A:
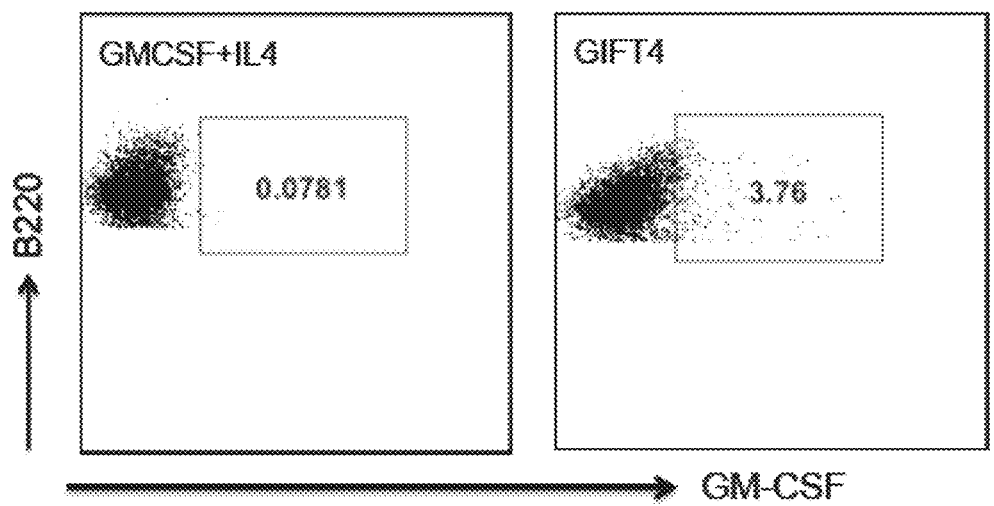
FIG. 9A shows data on GIFT4-triggered expansion of GM-CSF+ IRA-like cells in vivo. Purified splenic B cells from mice treated with GIFT4 or combined use of GM-CSF and IL-4 were subject to intracellular staining of GM-CSF, followed by FACS.
Figure 9B:
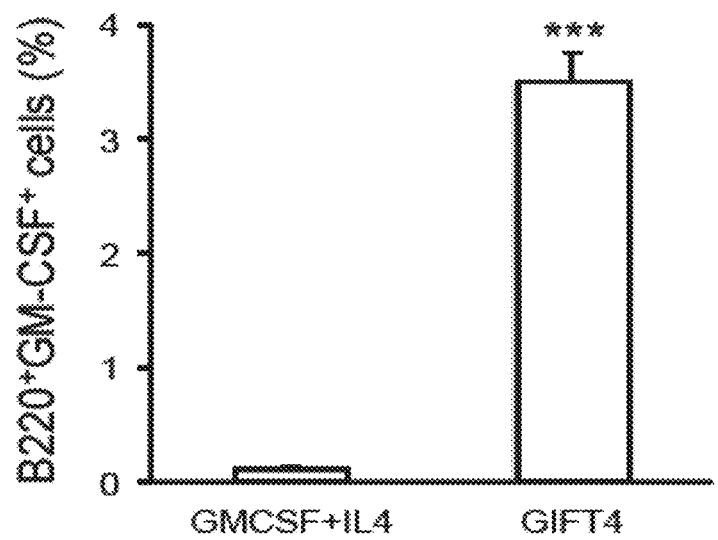
FIG. 9B shows the calculated percentage of GM-CSF-producing B cells was calculated. Data were represented from two independent experiments.

To examine the immune function of GIFT4 protein, splenocytes were isolate from C57BL/6J (B6) mice, and stimulate the cells with GIFT4 protein in comparison with combined use of its parental molecules GM-CSF and IL-4 in vitro. GIFT4 triggers the expansion of splenocytes (FIG. 9A), unexpectedly in the B-cell compartment (FIG. 9B). Consistently, GIFT4 induce the proliferation of purified B cells (FIG. 2A-B). To define the phenotype of GIFT4-treated splenic B cells (GIFT4-B cells), we profiled GIFT4-B cells with a panel of surface markers. FACS analyses demonstrated that GIFT4-B cells express B220, CD19, CD22, CD25, CD40, MHCI/II, IgM, CD80 and CD86 (FIG. 2C); the latter two are the common markers for antigen-presenting cells. BCR cross-linking with anti-murine IgM further confirmed that GIFT4-B cells have the plasticity to switch the isotype of immunoglobulin expression on the cells from IgM to IgG (FIG. 2D), with down-regulation of CD80 and CD86.

GIFT4 Triggers Anti-Tumor Immunity.

Figure 3A:
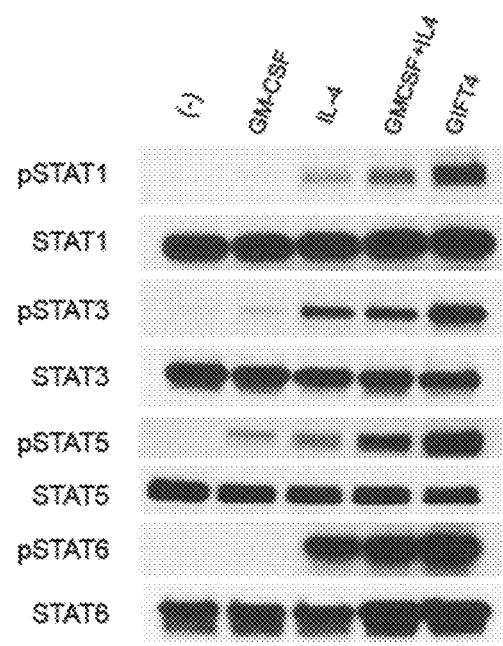
FIG. 3A shows data on the secretome of GIFT4-activated B cells. Phosphorylation of STAT1, STAT3, STAT5 and STAT6 activated by GIFT4 stimulation (20 minutes), detected by Western blot.
Figure 3B:
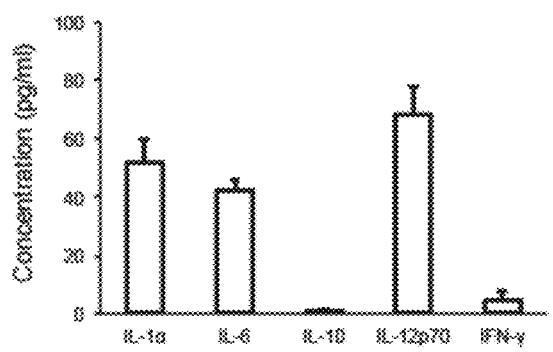
FIG. 3B shows data on the secretion of cytokines and chemokines by GIFT4-treated B cells; cytokine concentration was analyzed by luminex assay.
Figure 3C:
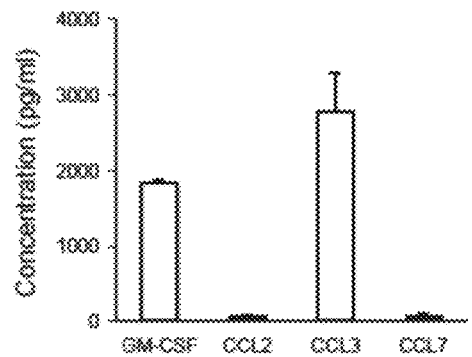
FIG. 3C shows data on the secretion of cytokines and chemokines by GIFT4-treated B cells; cytokine concentration was analyzed by luminex assay.
Figure 3D:
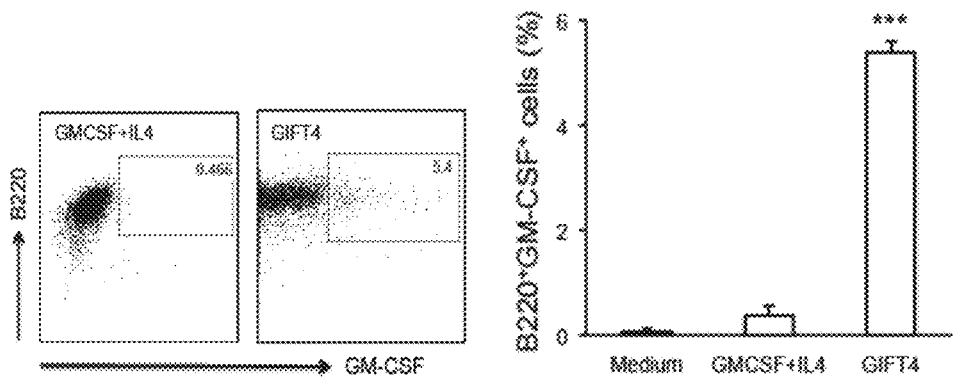
FIG. 3D shows induction of GM-CSF+ innate response activator (IRA, #42) B-cells profiled by FACS.
Figure 3E:
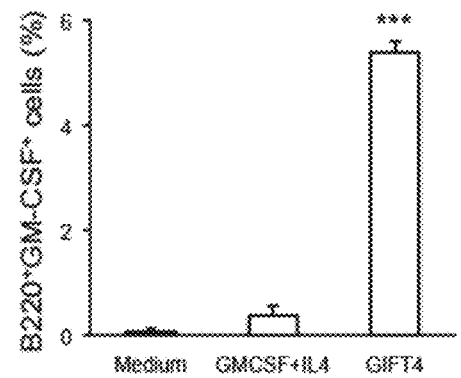
FIG. 3E shows calculated percentage of GM-CSF-producing B cells. Data were represented from three independent experiments.
Figure 4A:
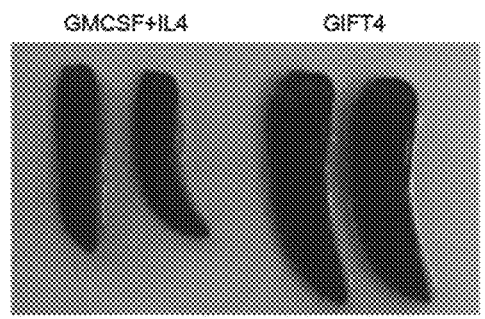
FIG. 4A shows data on the suppression of melanoma tumor growth in vivo by GIFT4. Splenomegaly in C57BL/6J mice treated with GIFT4. Administration of recombinant GM-CSF and IL-4 served as control.
Figure 4B:
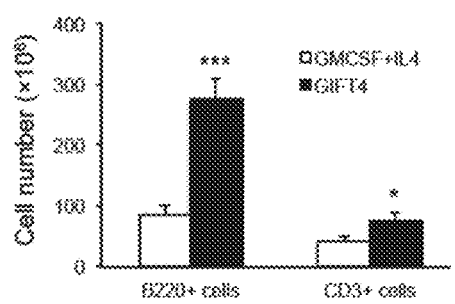
FIG. 4B shows data when splenocytes per spleen were isolated and counted. B cells and T cells were profiled by FACS analysis. Total splenic B cells or T cells were calculated.
Figure 10:
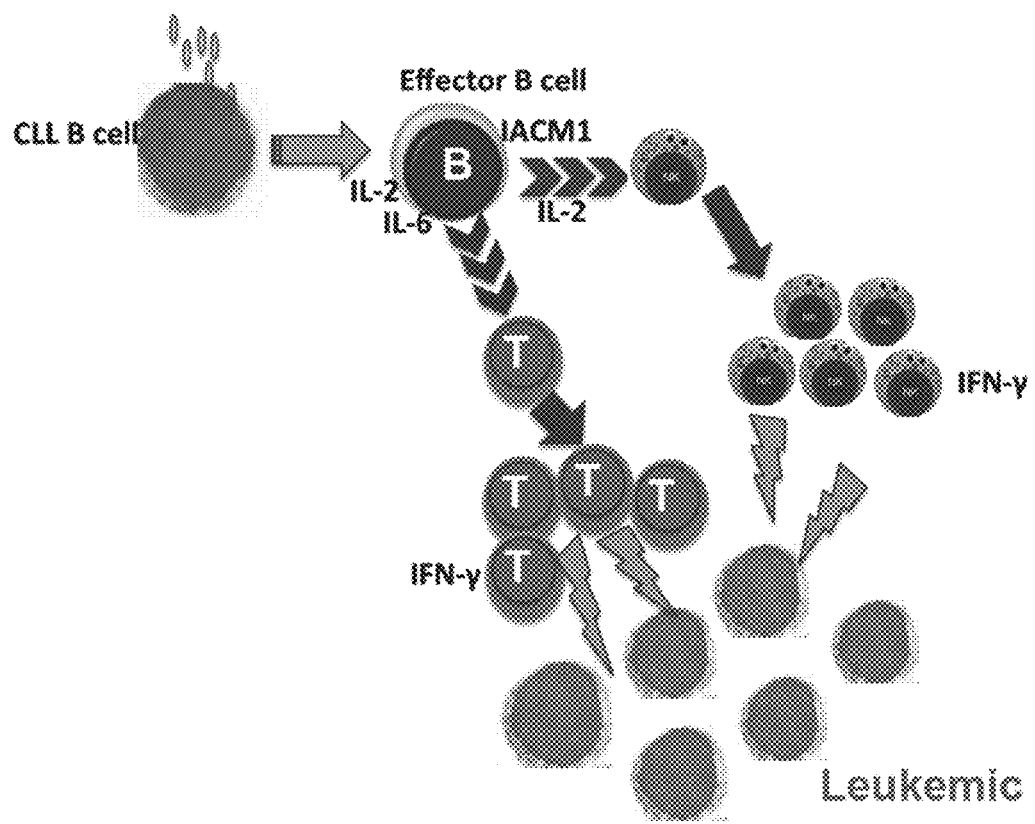
FIG. 10 illustrates a proposed model of GIFT4 immune functions on CLL cells. GIFT4 has potent anti-CLL immune function by reprograming leukemic B cells into anti-CLL effectors and helpers, which drive the expansion of IFN-γ, NK, and T cells, as well as NKT cells.

Cytokine secretion by B cells plays important roles in both innate and adaptive immunities against infectious pathogens and tumors. IL-4 is a γ chain family member that induces the phosphorylation of STAT6. To test the capacity of GIFT4 on STAT signaling, purified murine B cells were stimulated with GIFT4 protein, compared to the stimulation of individual or combined recombinant GM-SCF and IL-4. GIFT4 possesses gain-of-function on the phosphorylation of STAT1, STAT3, STAT5 and STAT6 (FIG. 3A). To check cytokine production by GIFT4-B cells, the culture supernatant of purified splenic B cell stimulated with GIFT4 protein was subject to cytokine luminex analyses. The prolife of secretome revealed that GIFT4-B cells produce IL-1β, IL-6, IL-12 (FIG. 3B), IL-5, VEGF, and massive amount of GM-CSF and the chemokine CCL3 (FIG. 3C), with undetectable IL-10 and little IFN-γ (FIG. 3B), as well as other lower level of cytokines. Intracellular cytokine staining further confirmed the secretion of GM-CSF by GIFT4-B cells (FIG. 3D), which is more than ten folds higher in comparison with the one in control treatment with combined use of recombinant GM-CSF and IL-4 (FIG. 3E). To test the effect of GIFT4 protein on GM-CSF-producing B cells in vivo, GIFT4 protein was administrated into B5 mice by intravenous injection. After one week of GIFT4 treatment, the mice developed splenomegaly (FIG. 4A); mice treated with combined GM-CSF and IL-4 showed normal size of spleens (FIG. 4A) as untreated mice (not shown). Profiling B220+ cells and CD3+ cells in the spleens from those mice by FACS demonstrated that there was robust expansion of splenic B cells in GIFT4-treated mice, compared with the mice treated with GM-CSF and IL-4 (FIG. 4B); there was also slight T cell proliferation in GIFT4-treated mice. Intracellular staining further confirmed the induction of GM-CSF-secreting splenic B cells by GIFT4 treatment. The percentage of GM-CSF+ B cells in GIFT4-treated mice is more than 30 folds higher than the one in mice treated with GM-CSF and IL-4 (FIG. 10B), the latter is similar to normal untreated mice.

Figure 4C:
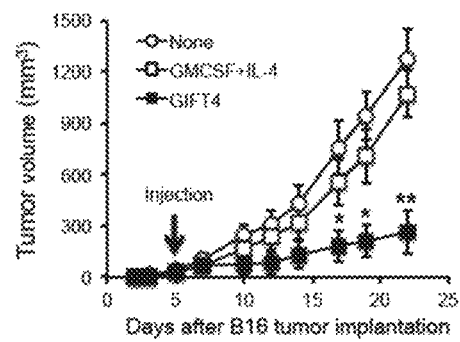
FIG. 4C shows data when B16F0 melanoma cells were subcutaneously implanted into C57BL/6J mice. On day 5, the mice were treated with GIFT4 protein by intravenous injection; mice administrated with GM-CSF plus IL-4 or untreated mice served as control.

GM-CSF is contemplated as a cytokine adjuvant for tumor vaccine. GIFT4-B cells secrete IL12, IL-6 and IL-1β, which could enhance Th1 T cell response and the production of IFN-γ that is an essential anti-tumor cytokines. Therefore, GIFT4 protein could elicit anti-tumor immunity in vivo. To test, melanoma mouse model was established by subcutaneous implantation of B16F0 melanoma cells into B6 mice. Five days after tumor implant, there were visible tumors developed in the mice. Those mice were treated with GIFT4 protein or combined GM-CSF and IL-4, or PBS as untreated control. Two weeks later, the mice in control group or combined cytokine treatment developed massive melanoma tumors (FIG. 4C); in contrast, GIFT4 treatment significantly suppressed tumor growth (FIG. 4C).

Figure 4D:
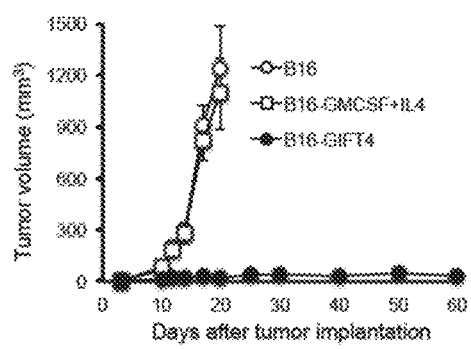
FIG. 4D shows data when GIFT4-expressing B 16F0 melanoma cells were subcutaneously implanted in B6 mice. Mixture of B16F0-GMCSF plus B16F0-IL-4 melanoma cells or wild type B16F0 cells served as control cells. Tumor size was measured. Five mice are in each group of treatment; data are represented from three independent experiments.

To further test the anti-tumor function of GIFT4 protein, genetically modified B16F0 melanoma cell line stably expressing GIFT4 protein (B16F0-GIFT4 cells) or individual GM-CSF or IL-4 cytokine were generated. The tumor cells were injected subcutaneously into syngeneic B6 mice. Twenty days later, mice implanted with wild type B16F0 cells or with mixed B16F0-GMCSF and B 16F0-IL4 cells (B16F0-GMCSF+IL4) developed substantial melanoma tumors (FIG. 4D); however, tumor growth was dramatically inhibited in mice implanted with B 16F0-GIFT4 cells, indicating GIFT4 expression significantly suppressed melanoma tumor growth (FIG. 4D).

GIFT4-Elicited Anti-Tumor Immunity is B-Cell Dependent.

Figure 5A:
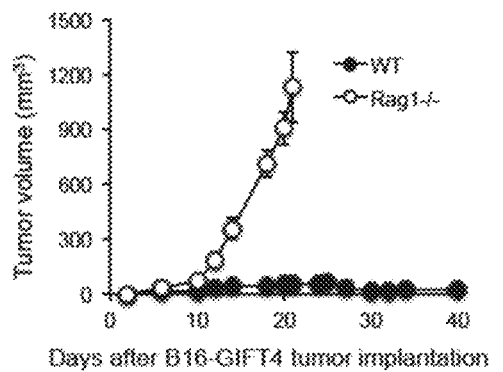
FIG. 5A shows data on the B-cell dependent tumorcidal activity elicited by GIFT4. B16F0-GIFT4 melanoma cells were subcutaneously implanted into Rag1 knockout, B-cell deficient (μMT), or wild type B6 mice. Rapid growth of melanoma tumors observed in absence of adaptive immunity.
Figure 5B:
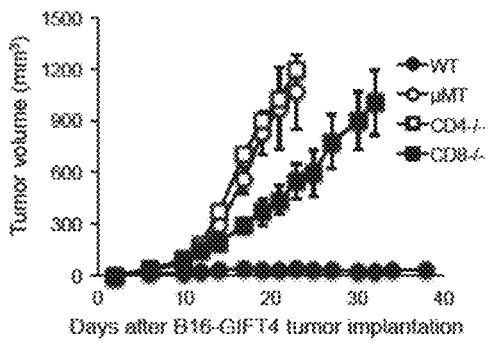
FIG. 5B shows data for CD4 or CD8 T cell-deficient mice.
Figure 5C:
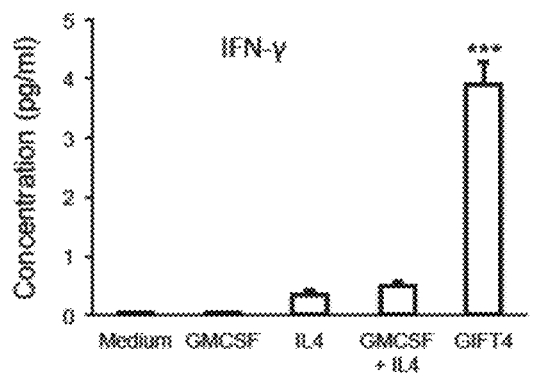
FIG. 5C shows data when T cells were co-cultured with B cells stimulated with GIFT4, individual or combined cytokines. IFN-γ production in the culture supernatant was measured with ELISA kit.
Figure 5D:
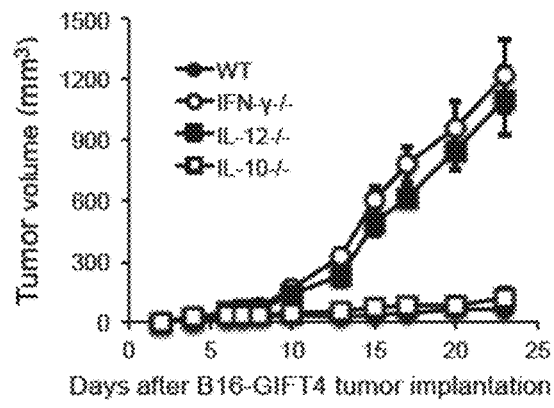
FIG. 5D shows data when B16F0-GIFT4 tumor cells were subcutaneously injected into IFN-γ−/−, IL-10−/−, IL-12−/− or wild type mice. Five mice are in each group; data are represented from three independent experiments.

Anti-tumor immunity consistent of two arms of innate and adaptive immune compartments. To check whether GIFT4 protein targets on the adaptive arm, B16F0-GIFT4 cells were implanted in Rag1$^{-/-}$ mice that lack functional B cells and T cells. Melanoma tumor grew quickly in Rag1$^{-/-}$ mice (FIG. 5A). T cells play roles in anti-tumor immunity. Growth of B16F0-GIFT4 tumors in CD4 T cell or CD8 T cell deficient mice was observed (FIG. 5B). To further test whether B cells play a pivotal role in GIFT4-triggered anti-tumor response, B16F0-GIFT4 cells were implanted into B cell deficient μMT mice. Consistent with the immune function of GIFT4 protein on B cells in vitro and in vivo, μMT mice that exclusively lack functional B cells developed large size of melanoma tumors (FIG. 5B). GIFT4-B cells secretes IL-12, IL-6 and IL-1β which can enhance IFN-γ production by T cells. To test whether GIFT4-B cells could interact T cells and promote anti-tumor immunity the hypothesis, T cells were co-cultured with purified B cells stimulated with GIFT4 protein, or individual GM-CSF or IL-4, or combined recombinant cytokines. Quantification of IFN-γ secretion in the culture supernatant by ELISA showed that GIFT4 stimulation robustly increased IFN-γ production by T cells (FIG. 5C), while control treatments with individual recombinant cytokine GM-CSF, IL-4 or combined use had no significant effect on T cell IFN-γ production. Using gene knockout mice, it was confirmed that mice deficient with IL-12 or IFN-γ, but not IL-10, could not suppress melanoma tumor growth (FIG. 5D).

Tumor-Specific Antibody is Important for GIFT4-Triggered Anti-Tumor Immunity.

Figure 6A:
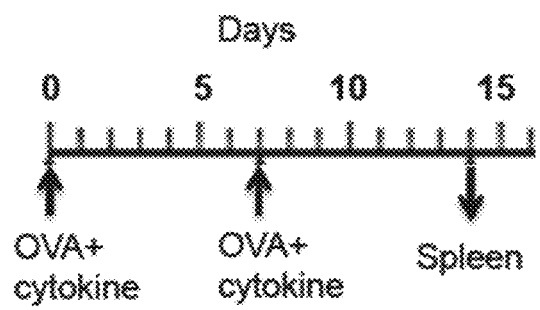
FIG. 6A shows data on the antigen-melanoma specific antibody production enhanced by GIFT4. Time schedule of OVA administration in C57BL/6J mice. OVA were injected into mice supplemented with GIFT4 protein or combined recombinant GM-CSF and IL-4. Mice without cytokine treatment served as blank control.
Figure 6B:
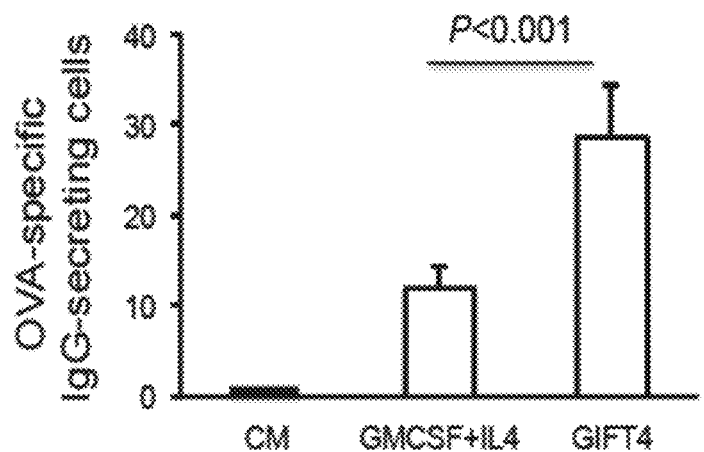
FIG. 6B shows data when spleens were harvested from the mice, and B cells were purified from splenocytes. OVA-specific IgG-secreting cells per 50,000 B cells were determined by ELISpot assay.
Figure 6C:
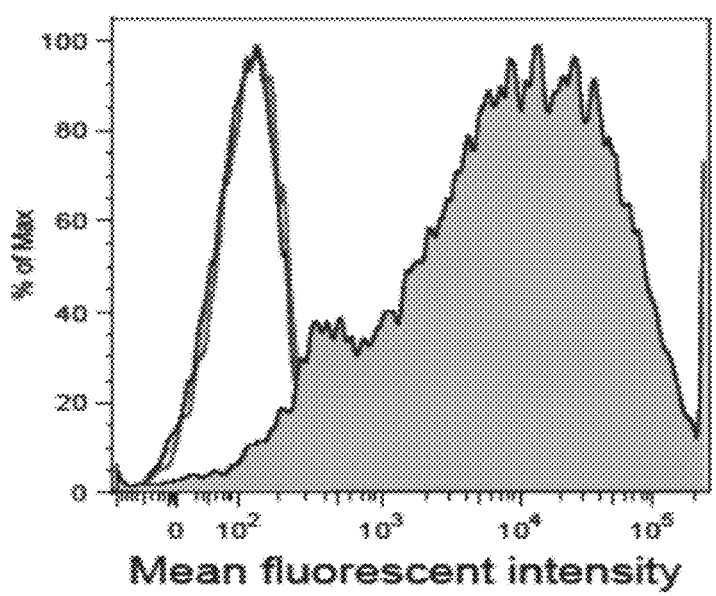
FIG. 6C shows data when C57BL/6J mice (gray color filled) or B-cell deficient mice (unfilled gray line) were immunized with B16F0-GIFT4 cells. PBS-treated mice served as controls (unfilled black line). Sera from the mice were used as primary antibody for FACS analysis with B16F0 melanoma cells followed by incubation of PE-conjugated anti-mouse IgG secondary antibodies.
Figure 6D:
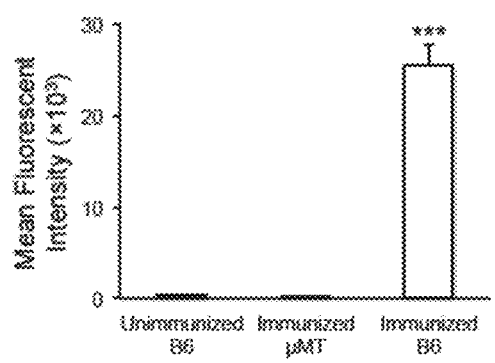
FIG. 6D shows data for mean fluorescent intensity of B 16F0 melanoma cells treated with serum from mice in each group. Five mice are in each group; data are represented from three independent experiments.
Figure 6E:
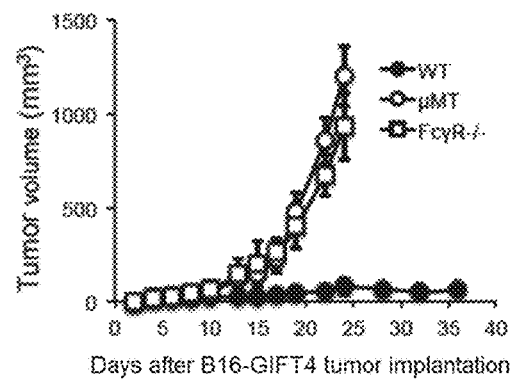
FIG. 6E shows data when FcγR−/−, B-cell deficient μMT or wild type C57BL/6J mice were implanted with B16F0-GIFT4 melanoma cells. Tumor growth was monitored and measured. Five mice are in each group; data are represented from three independent experiments.
Figure 7A:
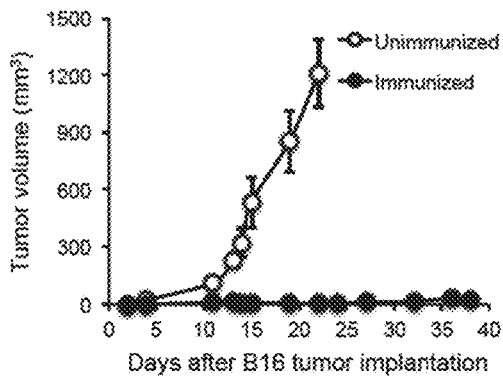
FIG. 7A shows data on the inhibition of melanoma tumor growth by adoptive-transferred B cells. Immunized mice or unimmunized control C57BL/6J mice were challenged with B16F0 melanoma cells on day 30, and tumor growth was monitored and measured.
Figure 7B:
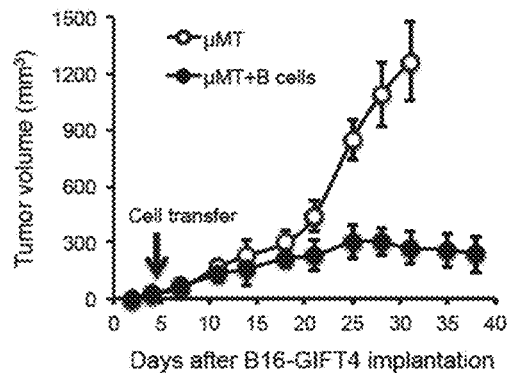
FIG. 7B shows data when μMT mice implanted with B16F0-GIFT4 tumor cells were adaptively transferred with B cells isolated from immunized C57BL/6J mice. Mice without B cell transfer served as control. Five mice are in each group of treatment; data are represented from three independent experiments.
Figure 8A:
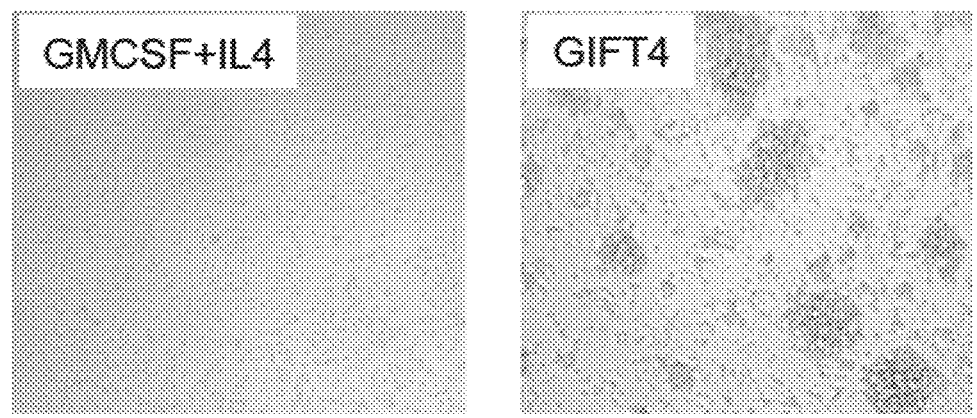
FIG. 8A shows data on the induction of splenic cell proliferation by GIFT4 stimulation. Splenocytes isolated from C57BL/6J mice were treated with GIFT4 or combined recombinant GM-CSF and IL-4 for 5 days. Expansion of splenocytes aggregated as clusters.
Figure 8B:
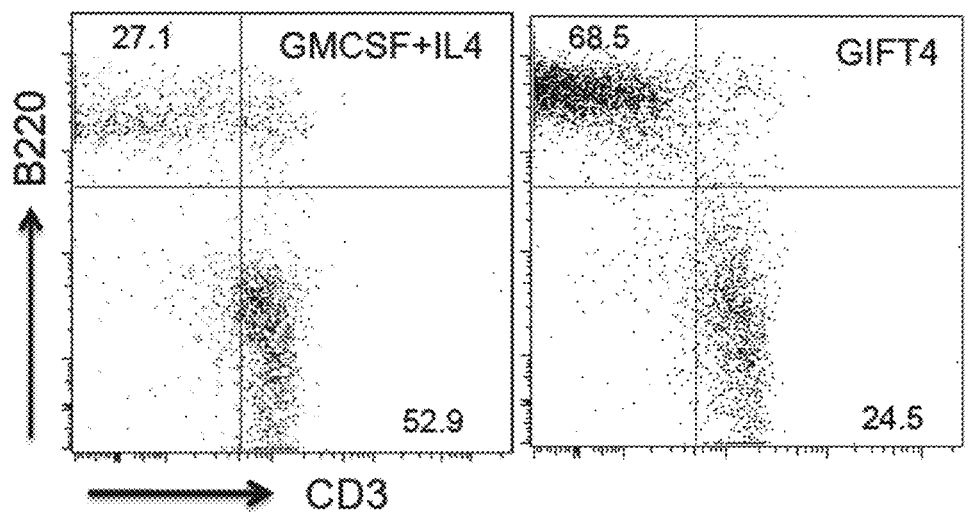
FIG. 8B shows data when cells were collected and subjected to FACS with anti-mouse B220 and anti-CD3 antibodies, typical antibodies for murine B cells and T cells.

B cell immunity includes cellular and humoral immune responses. To test whether GIFT4 could boost B cell antibody response, normal B6 mice were immunized with ovalbumin (OVA) in presence of GIFT4 protein or mixed GM-CSF and IL-4. Mice injected with control medium absent OVA served as the control (FIG. 6A). ELISpot analyses of OVA-specific IgG-secreting B cells from the harvested spleens demonstrated that OVA with GIFT4 treatment significantly enhanced antigen-specific antibody production in vivo, compared with OVA plus GM-CSF and IL-4 (FIG. 6B). There was undetectable OVA-specific IgG secreting B cells existed in the spleen when no antigen was administrated in the control mice. To examine the capability of GIFT4 protein as an adjuvant to boost anti-tumor specific antibodies, B6 or μMT B-cell deficient mice were immunized with B 16F0-GIFT4 melanoma cells. One month later, serum was collected from the mice. Flow cytometry analyses of B16F0 cells treated with the serum from the immunized mice or naïve B6 mice verified the presence of high title of anti-melanoma specific antibodies in immunized B6 mice (FIG. 6C-D). B-cell deficient mice μMT mice and naïve B6 mice have undetectable anti-B16F0 antibodies in the circulation. To test whether the anti-melanoma antibodies involved in GIFT4-triggered B cell-mediated anti-tumor immunity, B16F0-GIFT4 melanoma cells were subcutaneously implanted into B6, FcγR$^{-/-}$ or μMT mice. FcγR$^{-/-}$ mice lack functional IgG. Monitoring tumor growth demonstrated that there was massive tumor growth in FcγR$^{-/-}$ mice, as well as in μMT B-cell deficient mice, but not in the wild type mice (FIG. 6E). To examine whether the immunization of B16F0-GIFT4 cells could elicit protective immunity against melanoma, immunized or unimmunized mice were challenged with B16F0 tumor cells. Immunization of B16-GIFT4 cells completely prevented the mice from developing melanoma tumors (FIG. 7A). In contrast, mice without immunization developed large tumors (FIG. 7A). Adoptive transfer of immune cells is a promising approach for cancer cell immunotherapy. To further investigate whether GIFT4-activated B cells from immunized mice could pass the active anti-tumor immunity into B cell deficient mice, B16F0-GIFT4 cells were implanted into μMT mice. When the mice developed a visible size of melanoma tumors, splenic B cells purified from immunized mice were adoptively transferred into the mice. Measurement of the tumor size showed that adoptive transfer of B16F0-primed B cells from immunized mice significantly inhibited melanoma tumor growth in B-cell deficient μMT mice (FIG. 7B). Mice without B-cell adoptive transfer developed large size of melanoma tumors.

Figure 12A:
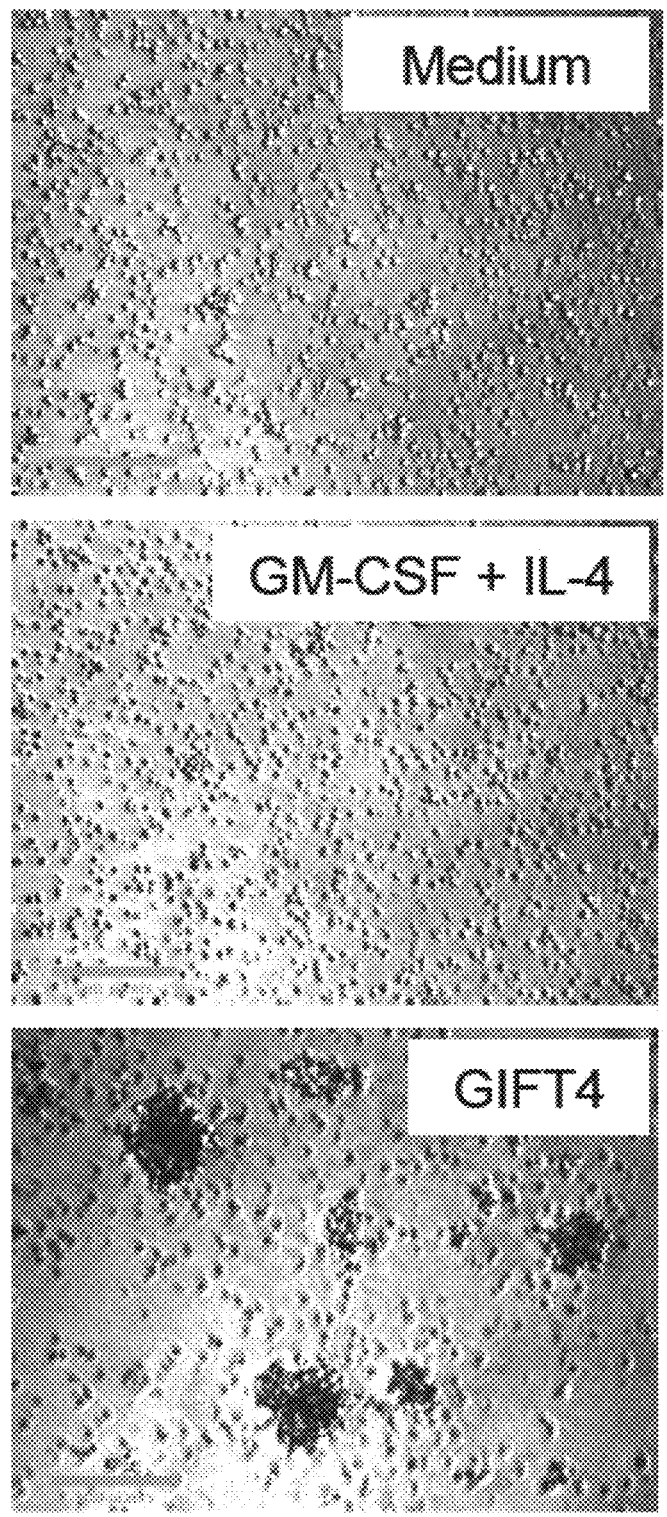
FIG. 12A shows data on the activation of CLL-B cells by human GIFT4 protein. Purified CLL B cells were stimulated with human GIFT4 protein or combined GM-CSF plus IL-4.
Figure 12B:
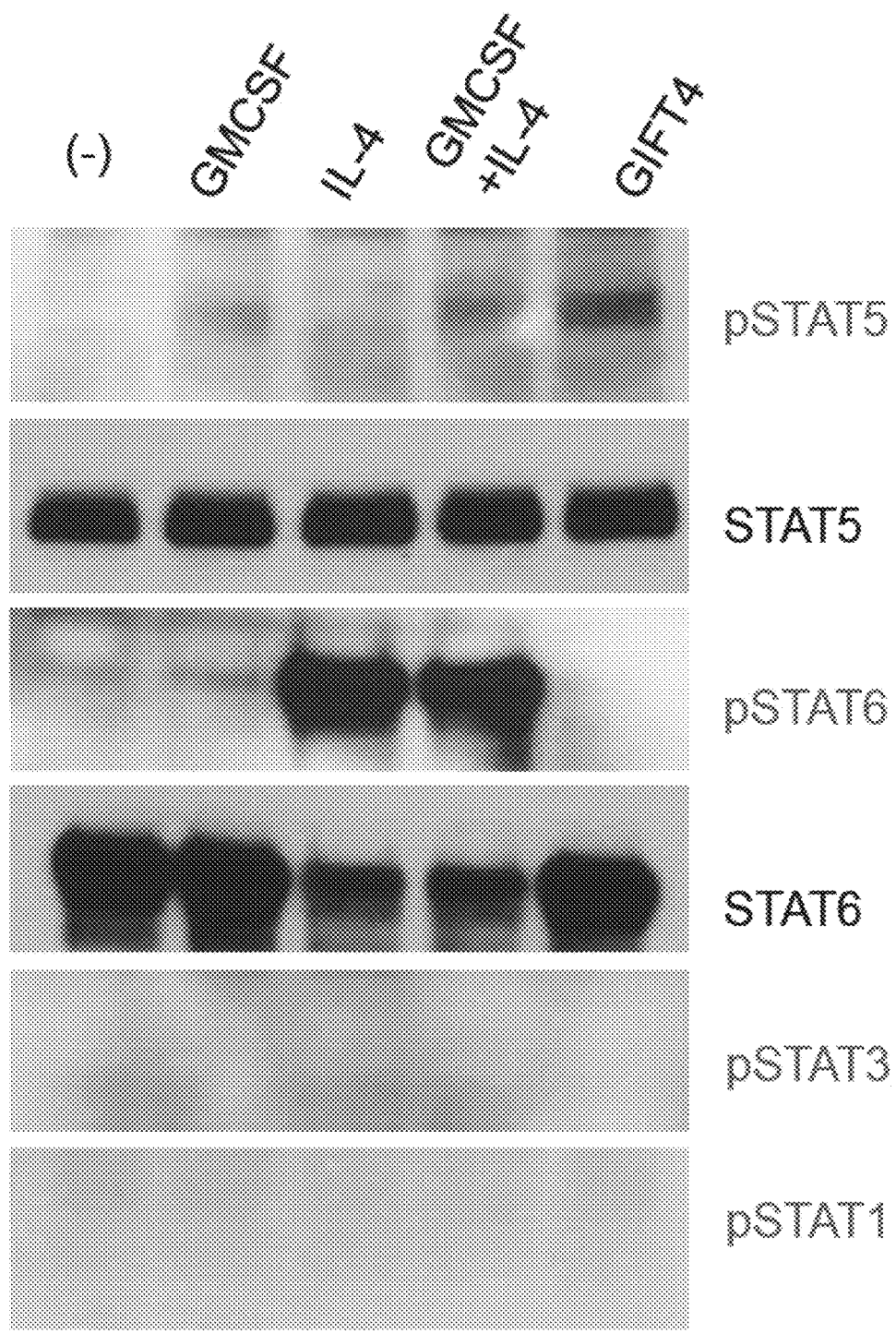
FIG. 12B shows data indicating GIFT4 triggers hyper-phosphorylation of STAT5 in CLL B cells, but not STAT1, 3 and 6.
Figure 13A:
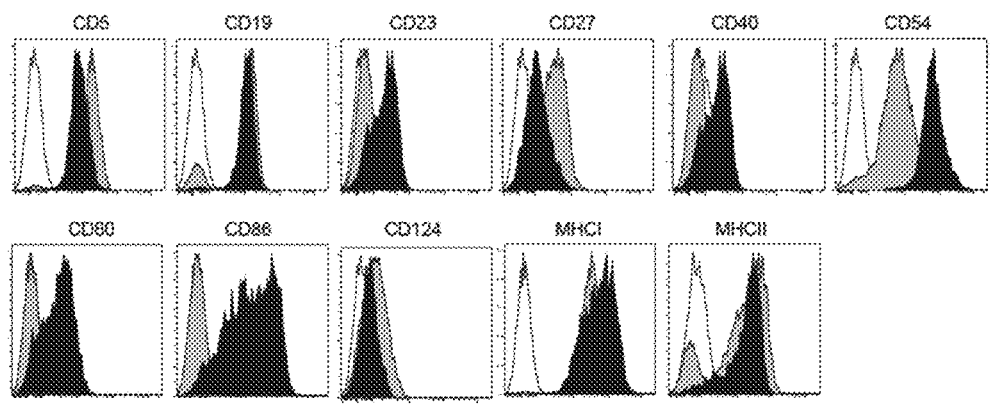
FIG. 13A shows data on GIFT4-converted CLL B cells have unique surface markers and secretome. GIFT4 reprograms leukemic B cells into antigen-presenting cells, which are CD5+, CD19+, CD23+, CD40+, CD54+, CD80+, CD86+, MHC I/II+, but CD124$^{low}$.
Figure 13B:
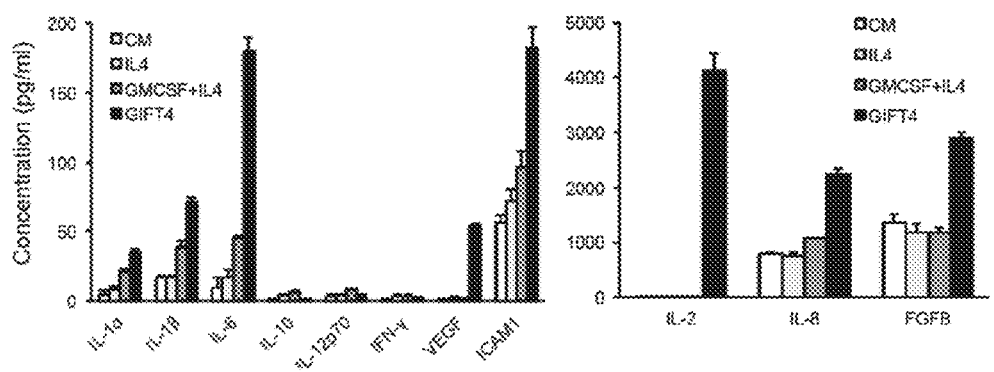
FIG. 13B shows data indicating GIFT4-treated CLL B cells secrete IL-1β, IL-6, ICAM1 and massive amounts of IL-2.
Figure 14A:
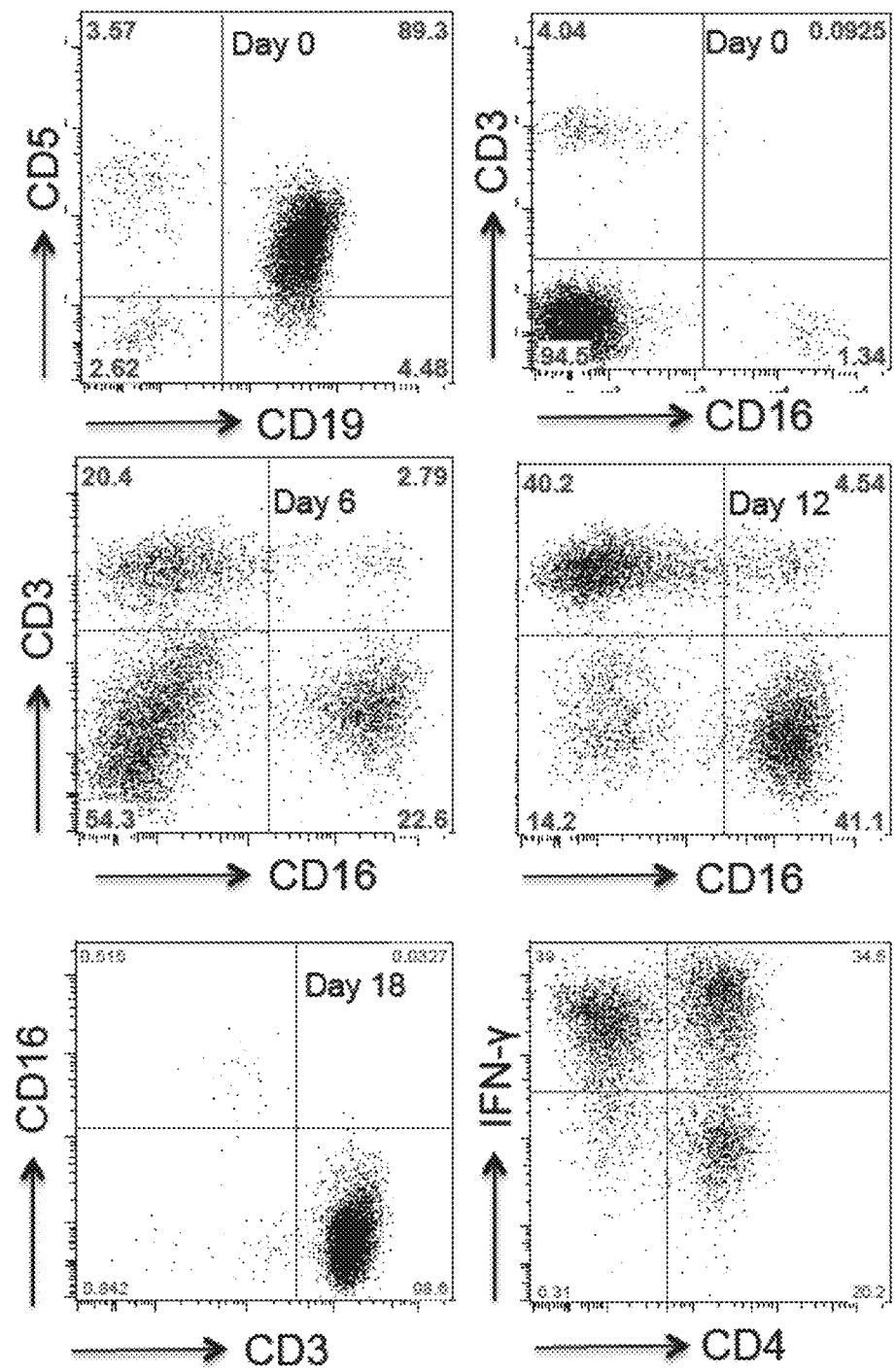
FIG. 14A shows data indicating GIFT4-reprogramed CLL B cells prime autologous NK and T cell immune response. CD5+CD19+ B cells are the major component of CLL cells, CD3+ T cells and CD16+ NK cells are the minor populations (upper panels). GIFT4 treatment robustly propelled the expansion of NK and T cells, as well as CD3+CD16+ NKT cells (middle panels), which produce massive IFN-γ (low panels).
Figure 14B:
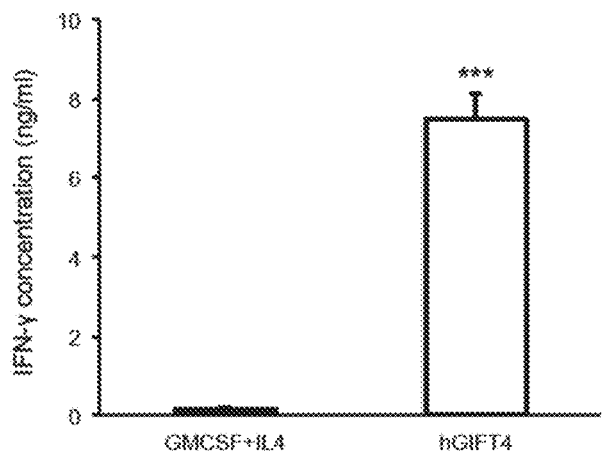
FIG. 14B shows data for IFN-γ.
Figure 14C:
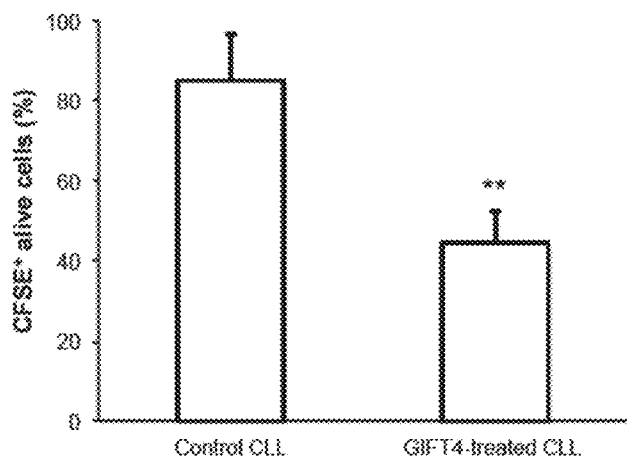
FIG. 14C shows data when co-culture of GIFT4-treated CLL cells with primary autologous CLL cells from patients led to the killing of primary pCLL cells in vitro.
Figure 15A:
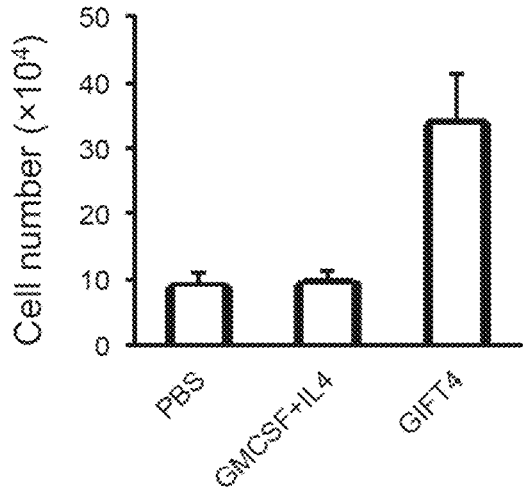
FIG. 15A shows data indicating GIFT4 treatment increases bone marrow stem cells (BMSC) in B6 mice (Lin−SCA-1+CD117+). GIFT4 (20 ng/day) or control cytokines were injected into B6 Mice for 6 Days. Bone marrow cells were isolated and subject to FACS analysis with lineage markers and stem cell markers. The number of BMSC per femur was calculated. Experiments were repeated three, 5 mice each group.
Figure 15B:
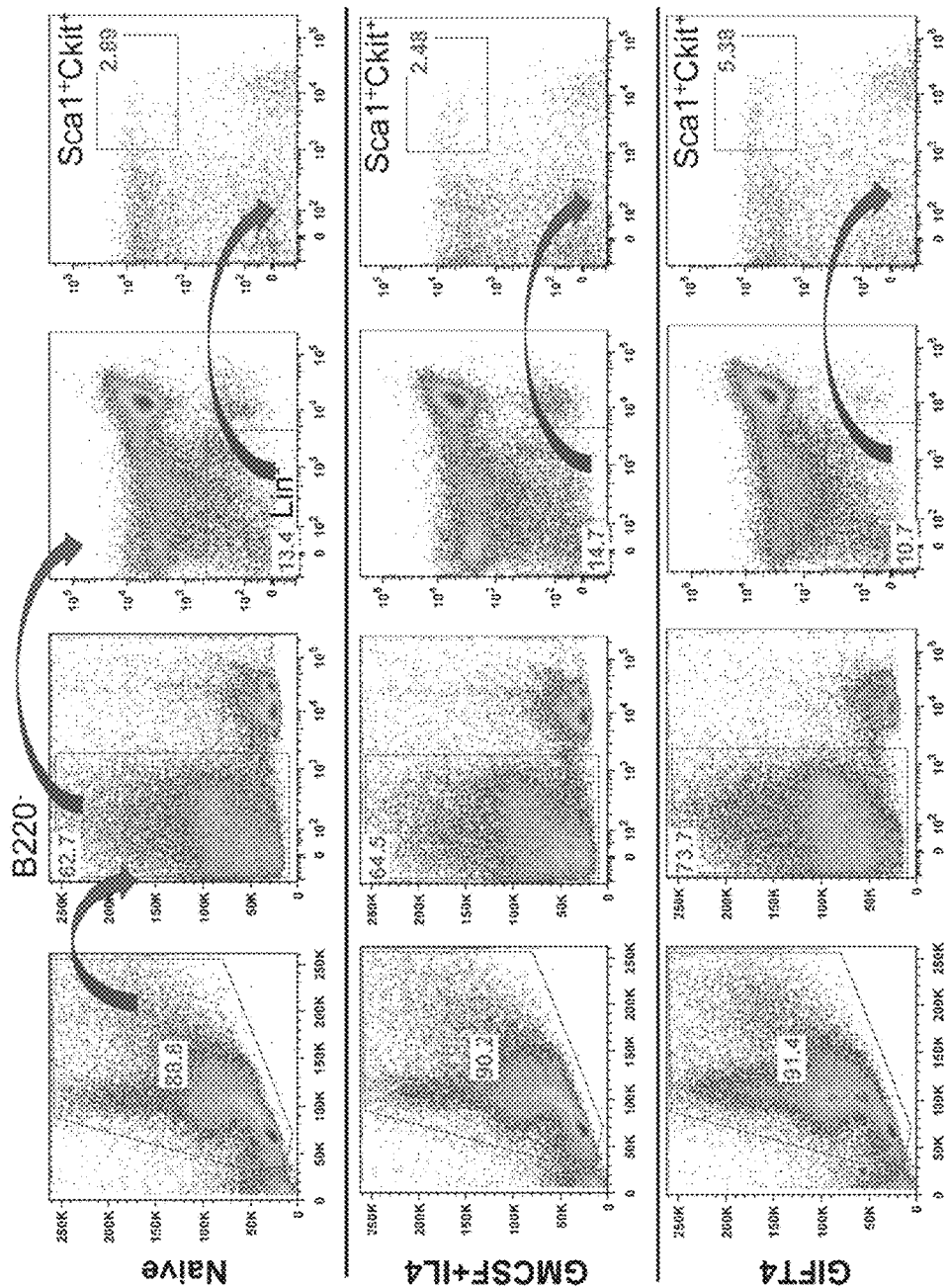
FIG. 15B shows data on the surface markers that are Lin⁻Sca-1⁺Ckit⁺.
Figure 16:
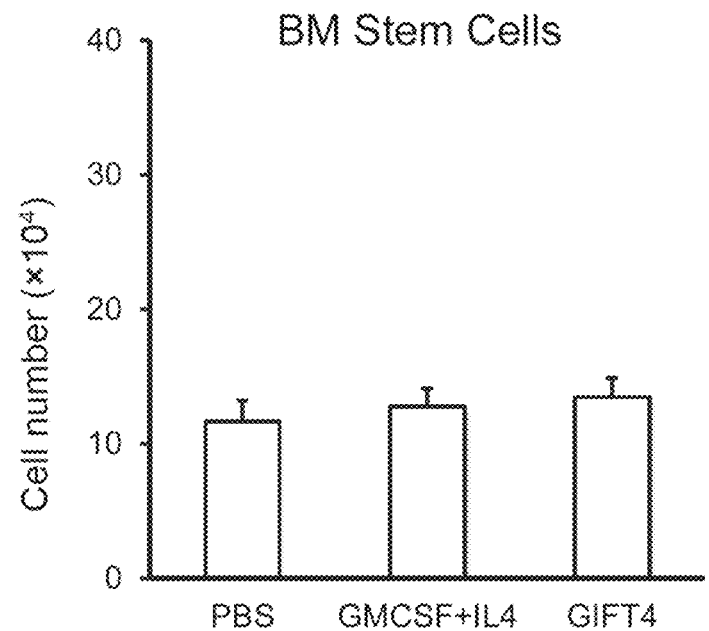
FIG. 16 shows data indicating B-cell deficiency abrogates the increase of BMSC in μMT mice. GIFT4 (20 ng/day) or control cytokines was injected into μMT B cell-deficient mice for 6 Days. Bone marrow cells were isolated and subject to FACS analysis with lineage markers and stem cell markers (See FIG. 15). The number of BMSC per femur was calculated. Experiments were repeated twice, 5 mice each group.
Figure 17:
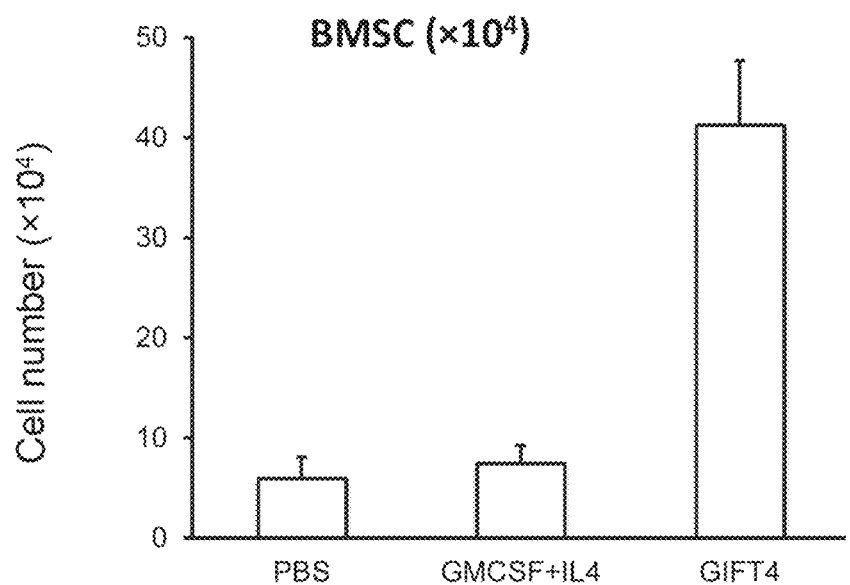
FIG. 17 shows data indicating adoptive transfer of B cells promotes BMSC expansion in μMT mice after GIFT4 treatment. Adoptive transfer of B cells (2×10⁷ cells/mouse) into μMT B cell-deficient mice combined with GIFT4 treatment for 6 days. Bone marrow cells were isolated and subject to FACS analysis with lineage markers and stem cell markers (See FIG. 15). The number of BMSC per femur was calculated. Experiments were repeated twice, 5 mice each group.
Figure 18:
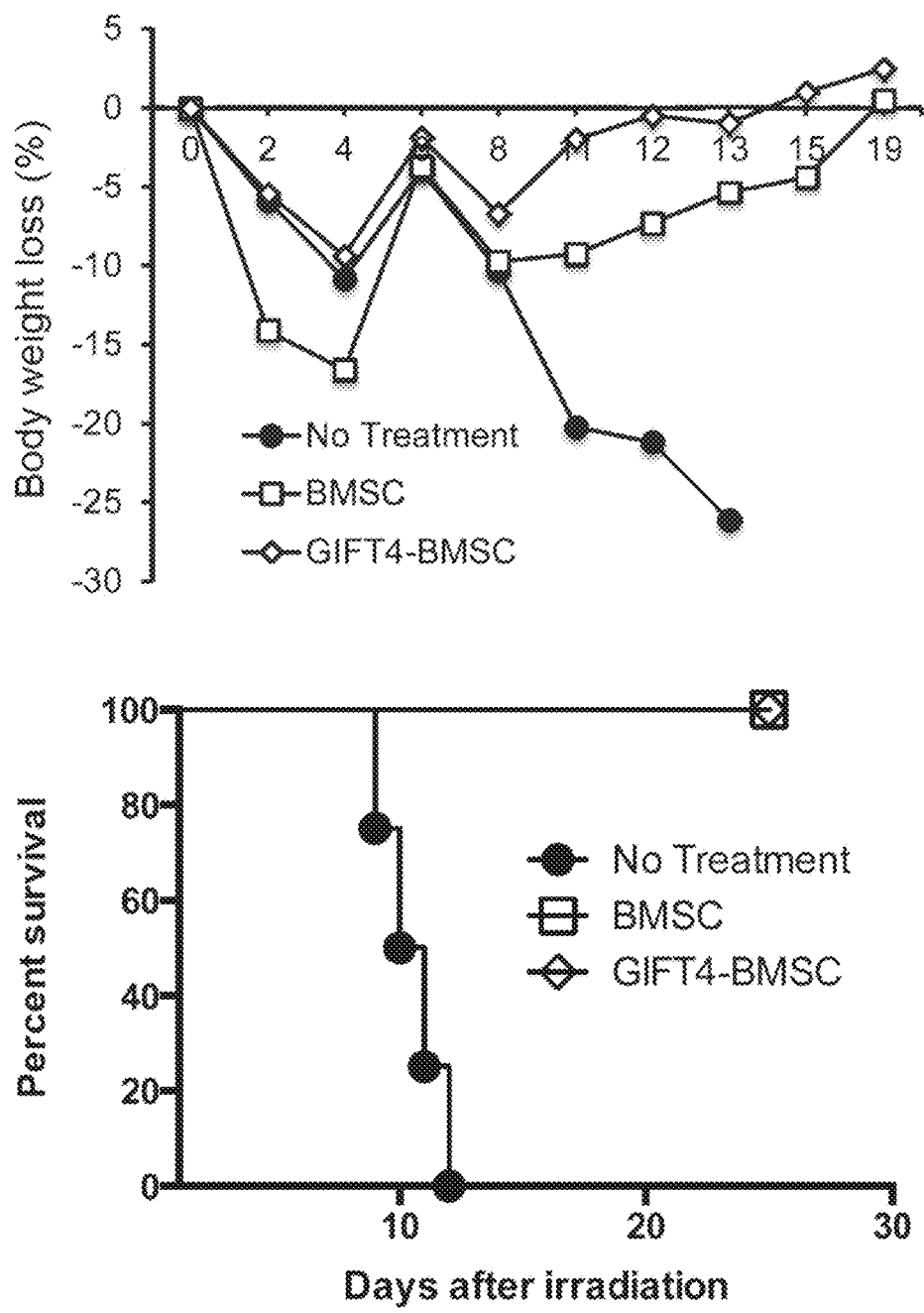
FIG. 18 shows data indicating GIFT4 programmed BMSC have similar functions with the BMSC from naïve mice. B6 mice were irradiated at 11 Gy (5.5+5.5 Gy, 3 hr interval), then injected i.v. with BMSC purified from mGIFT4-treated or naïve mice. Mice weight loss and survival were monitored. Experiments were repeated twice, 5 mice each group.
Figure 19:
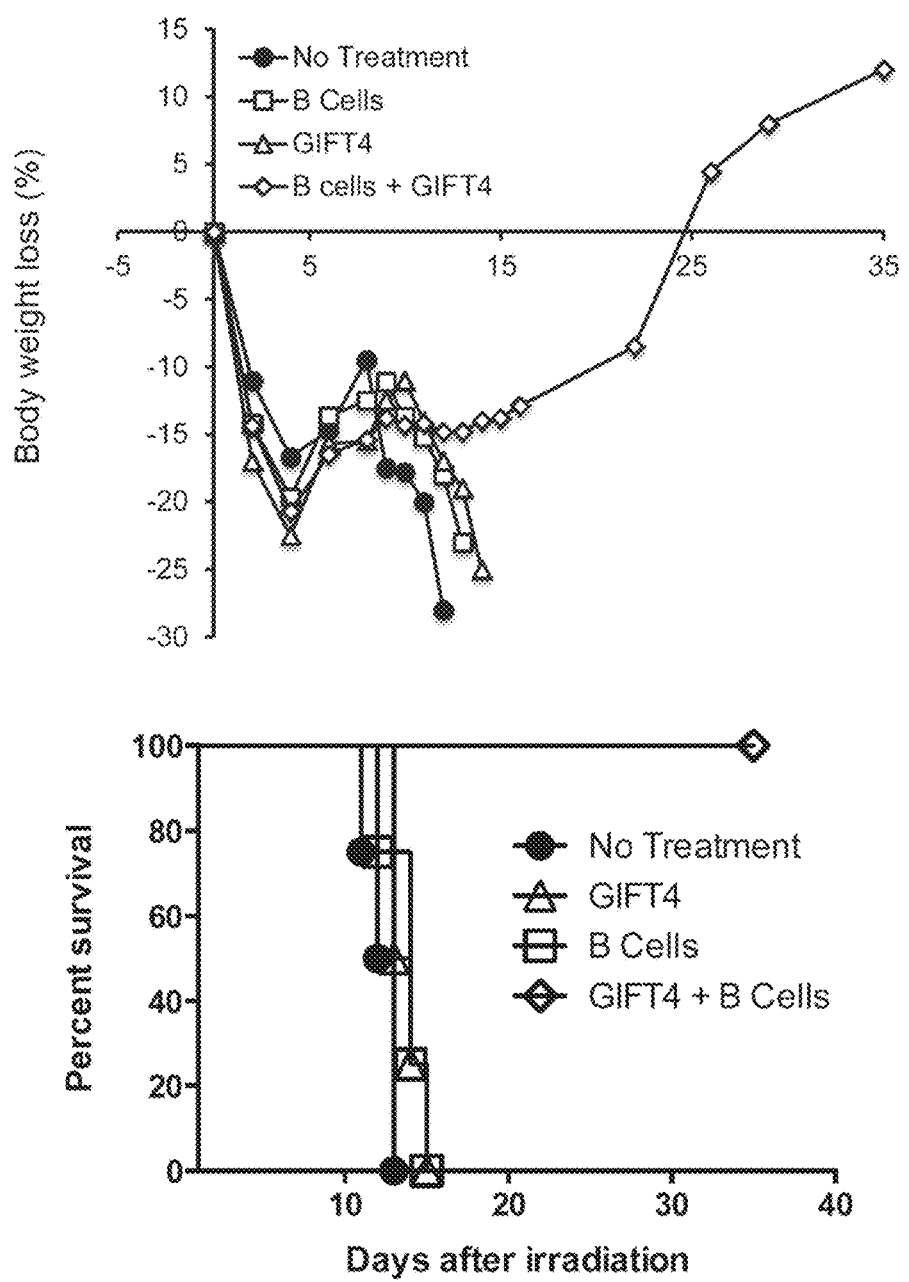
FIG. 19 shows data indicating delivery of GIFT4 plus B cells ameliorates irradiation-caused bone marrow failure. B6 mice were irradiated at 11 Gy (5.5+5.5 Gy, 3 hr interval), then injected i.v. with mGIFT4 (20 ng/mouse/day for 6 days), or plus B cells (2×106 cells/mouse). Mice without treatment served as controls. Mice weight loss and survival were monitored. Experiments were repeated twice, 5 mice each group.

Human GM-CSF and IL-4 Derived Fusion Cytokine Reprograms Leukemic B-Cells to Anti-CLL Effectors A human GM-CSF and IL-4 derived fusokine GIFT4 was generated to test its immune function on chronic lymphoid leukemia B-cells (CLL-B cells). (FIG. 11) Human GIFT4 protein reprograms leukemic B cells into anti-CLL effectors and helpers. (FIG. 10) GIFT4 activated CLL B cells via exclusive hyper-phosphorylation of STATS. Unlike the induced expansion of normal human B cells, GIFT4 did not trigger CLL B-cell proliferation. (FIG. 12) GIFT4-converted CLL B-cells up-regulated the expression of co-stimulatory molecules CD40, CD80 and CD86, behaved like antigen-presenting cells, and secreted IL-1β, IL-6, ICAM1 and massive IL-2. (FIG. 13) GIFT4-CLL B cells further propelled the expansion of IFN-γ-producing autologous cytotoxic NK and T cells. Co-culture GIFT4-treated CLL cells significantly increased the killing of primary autologous CLL cells ex vivo. (FIG. 14) Together, these data demonstrate that GIFT4 has potent anti-CLL immune function by reprograming leukemic B cells into anti-CLL helper cells. Fusokine GIFT4 protein and GIFT4-converted CLL-B cells could serve as novel immunotherapeutic for CLL treatment.

Cell Culture

GIFT4-secreting 293T cells or B16F0 melanoma cell line, or non-transfected cells were cultured in DMEM medium (Wisent Technologies, Rocklin, Calif.) supplemented with 10% FBS (Wisent Technologies) and 50 U/ml of Pen/Strep antibiotics (Wisent Technologies). Culture supernatant was collected and concentrated with sterile centrifugal filter units (Millipore Corporation, Billerica, Mass.) for ELISA assay and Western blot. The concentrated culture supernatant of 293T-GIFT4 cells was further used for in vitro and in vivo experiments. Splenocytes from C57BL/6J mice or B cells ($10^5$ cells/well) purified from splenocytes by negative selection with B-cell enrichment kit (StemCell, Montreal, Canada) were cultured in complete RPMI 1640 medium for 6 days in presence of 2 ng/ml of GIFT4 protein or recombinant GM-CSF and IL-4 control proteins (R&D system, Minneapolis, USA). Alternatively, B cells were labeled with CFSE dye (Invitrogen, Eugene, Oreg.) and cultured in complete RPMI 1640 medium for cell proliferation assay following the instruction from the company.

ELISA and Western Blot

Quantification of GIFT4 protein expressed by transfused 293T or B16F0 melanoma tumor cells was performed with ELISA kits for murine GM-SCF or IL-4 (eBiosciences, San Diego, Calif.) following the instruction from the company. IFN-γ production by T lymphocytes in vitro was determined with IFN-γ ELISA kit from eBiosciences. Intact murine GIFT4 proteins were analyzed by Western blot with anti-mouse MG-SCF or anti-IL-4 specific antibodies (R&D systems). STAT phosphorylation activated by GIFT4 stimulation in B cells was profiled by Western blot with anti-pSTAT1, anti-pSTAT3, anti-pSTAT5, anti-pSTAT6, or anti-STAT antibodies (Cell Signaling, Boston, Mass.).

MTT Assay

For determining the bioactivity of IL-4 or GM-CSF fusion compartments of GIFT4 protein, IL-4-responsive CT.h4S cells (Provided by the laboratory of Dr. William Paul in National Institutes of Health, USA) and GM-CSF-responsive JASWII cells were plated at a density of 5,000 cells per well in a 96-well plate, and cultured in complete RPMI 1640 medium supplemented with 2 ng/ml of recombinant IL-4 cytokines or 10 ng/ml of recombinant GM-CSF (PeproTech, Rocky Hill, N.J.) respectively, or with GIFT4 protein (2 ng/ml for CT.h4S cells and 10 ng/ml for JASWII cells). After 72-hour culture, 20 μL of 3-(4,5-dimethylhiazol-2-yl)-2,5-diphenyltetrazolium bromide (MTT) (Sigma, Saint Louis, Mo.) solution was added for 4 hours of incubation at 37° C. Cell pellet was dissolved in 200 μL of absolute DMSO (Quality Biological Inc., Solon, Ohio), and read at an absorbance of 570 nm on a microplate spectrophotometer (BioTek Instruments Inc., Winooski, Vt.).

Cell Flow Cytometry

GIFT4-treated splenocytes in vitro were stained with APC-conjugated anti-mouse B220 and PE-conjugated anti-mouse CD3 antibodies. B-cell and T-cell profiles were analyzed by cell flow cytometry (FACS) on a BD FAC-SCanto II flow cytometer. Surface markers of GIFT4-treated B cells purified from splenocytes were profiled by flow cytometry with a panel of B cell surface markers (anti-B220, CD19, CD22, CD23, CD25, CD27, CD40, CD69, CD80, CD86, MHCI, MHCII, IgM, IgG) (BD, San Diego, Calif.). For intracellular GM-CSF staining, B cells were fixed and permeabilized with BD Cytofix/Cytoperm™ solution followed by GM-CSF antibody staining. Alternatively, murine GIFT4 protein (20 ng) was intravenously injected into C57BL/6J mice at day 0, 2 and 4. Recombinant murine GM-CSF and IL-4 (20 ng) served as protein control. Splenocytes were isolated from spleens of treated mice on day 6. Total B cells and T cells were profiled by cell flow cytometry with anti-B220 and anti-CD3 antibodies (BD), and the cell number per spleen was calculated. The production of specific antibodies against B16F0 melanoma cells in vivo was examined by FACS by incubation of serum from immunized or control mice with the melanoma cells, following with the staining of APC-conjugated donkey anti-mouse secondary antibodies (BD). FACS data were analyzed with FlowJo 9.1 software.

B Cell ELISpot

C57BL/6J mice were administrated by intraperitoneal injection with OVA protein (10 μg/mouse/time) supplemented with GIFT4 protein (20 ng/mouse/time) or combined recombinant GM-CSF and IL-4 (20 ng/mouse/time) on day 0 and 7. Mice without cytokine treatment served as blank control (n=5 in each group). On day 14, spleens were harvested, and B cells were purified from splenocytes by negative selection with B-cell enrichment kit (StemCell). The number of OVA-specific IgG-secreting cells per 50,000 B cells was analyzed by B-cell ELISpot kit (Mabtech, Cincinnati, Ohio) following the instruction provided by the manufacturer.

Luminex Assay

The culture supernatants of GIFT4-treated B cells were collected on day 5, and subject to luminex assay with murine 26-plex cytokine polystyrene bead kit (Affymetrix, Santa Clara, Calif.) performed in Human Immunology Monitoring Center of Stanford University, according to the manufacturer's instruction. Samples were read on a Luminex 200 instrument with a lower bound of 100 beads per sample per cytokine.

Murine Melanoma Model

B 16F0 or GIFT4-producing B 16F0 melanoma cells ($10^6$/mouse) were subcutaneously implanted into syngeneic C57BL/6J mice or Rag1$^{-/-}$, CD4$^{-/-}$, CD8$^{-/-}$, µMT (B-cell deficient) or FcγR$^{-/-}$ (IgG function-deficient) mice. Alternatively, GIFT4-secreting B 16F0 cells ($10^6$ cells/mouse) were subcutaneously immunized into C57BL/6J mice. After 30 days, wild type B16F0 melanoma cells ($10^6$/mouse) were implanted into the immunized mice. Unimmunized mice served as controls. Additionally, 10 millions of splenocytes or 5 millions of purified B cells isolated from immunized mice or control mice were adoptively transferred by intravenous injection into C57BL/6J mice with pre-established B16F0 melanoma. For testing the anti-tumor function of GIFT4 protein, C57BL/6J mice with pre-established B 16F0 tumors were administrated with three doses of 100 ng/day/mouse of murine GIFT4 with 2 days interval. In addition, purified splenic B cells ($10\times10^6$ cells/mouse) from immunized mice were adoptively transferred into B16F0 tumor pre-established µMT mice; mice without cell adoptive transfer served as control. Tumor growth was measured with a digital caliper. Mice used are female (6-8 weeks old) purchased from Jackson Laboratory (Bar Harbor, Me.).

The invention claimed is:

1. A method of treating cancer comprising administering a conjugate comprising the amino acid sequence of SEQ ID NO: 8 to a subject in need thereof, wherein the cancer is a hematological malignancy.

2. The method of claim 1, wherein the hematological malignancy is selected from leukemia, lymphoma, acute lymphoblastic leukemia (ALL), acute myelogenous leukemia (AML), chronic lymphocytic leukemia (CLL), small lymphocytic lymphoma (SLL), chronic myelogenous leukemia, acute monocytic leukemia (AMOL), Hodgkin's lymphomas, and non-Hodgkin's lymphomas such as Burkitt lymphoma, B-cell lymphoma and multiple myeloma.

3. A method of treating melanoma comprising administering a conjugate comprising the amino acid sequence of SEQ ID NO: 8 to a subject in need thereof.

* * * * *